United States Patent
Lund et al.

(10) Patent No.: US 9,701,703 B2
(45) Date of Patent: Jul. 11, 2017

(54) TRANSITION METAL COMPLEXES, THEIR PREPARATION AND USE

(71) Applicants: LANXESS Deutschland GmbH, Cologne (DE); THE GOVERNING COUNCIL OF THE UNIVERSITY OF TORONTO, Toronto (CA)

(72) Inventors: Clinton Lund, London (CA); Douglas Wade Stephan, Toronto (CA); Adam McKinty, Red Deer (CA); Christopher Ong, Orange, TX (US); Michael Boone, Toronto (CA)

(73) Assignee: ARLANXEO Deutschland GMBH, Dormagen (DE)

(*) Notice: Subject to any disclaimer, the term of this patent is extended or adjusted under 35 U.S.C. 154(b) by 0 days.

(21) Appl. No.: 14/893,673

(22) PCT Filed: May 23, 2014

(86) PCT No.: PCT/EP2014/060695
§ 371 (c)(1),
(2) Date: Nov. 24, 2015

(87) PCT Pub. No.: WO2014/187973
PCT Pub. Date: Nov. 27, 2014

(65) Prior Publication Data
US 2016/0108073 A1    Apr. 21, 2016

Related U.S. Application Data

(60) Provisional application No. 61/827,129, filed on May 24, 2013.

(30) Foreign Application Priority Data

Jul. 4, 2013   (EP) .................................... 13175093

(51) Int. Cl.
| | |
|---|---|
| *C07F 15/00* | (2006.01) |
| *B01J 31/00* | (2006.01) |
| *B01J 31/22* | (2006.01) |
| *C08F 136/20* | (2006.01) |
| *C08J 3/00* | (2006.01) |

(52) U.S. Cl.
CPC ........... *C07F 15/0046* (2013.01); *B01J 31/00* (2013.01); *B01J 31/2265* (2013.01); *B01J 31/2278* (2013.01); *C08F 136/20* (2013.01); *C08J 3/00* (2013.01); *B01J 2231/324* (2013.01); *B01J 2231/543* (2013.01); *B01J 2231/641* (2013.01); *B01J 2531/821* (2013.01); *C08J 2309/02* (2013.01)

(58) Field of Classification Search
CPC .. C07F 15/0046; B01J 31/403; B01J 2231/54; C08F 4/62141; C08F 4/7067
See application file for complete search history.

(56) References Cited

U.S. PATENT DOCUMENTS

| | | |
|---|---|---|
| 5,969,170 A | 10/1999 | Grubbs et al. |
| 2014/0051817 A1 | 2/2014 | Grubbs et al. |

OTHER PUBLICATIONS

Khan, R.K.M.; Torker, S.; Hoyveda, A.H. J. Am. Chem. Soc. 2013, 135, 10258-10261.*
Wang, T.; Pranckevicius, C.; Lund, C.L.; Sgro, M.J.; Stpehan, D.W. Organometallics 2013, 32, 2168-2177.*
Dahcheh, F.; Stephan, D.W. Organometallics 2013, 32, 5253-5255.*
Halbach et al. J. Org. Chem. 2005, 70, 4687-4694.*
Occhipinti, G. "Ruthenium Alkylidene Complexes of Chelating Amine Ligands", Organometallics, 2007, 26(24), Department of Chemistry, University of Bergen, Allegaten 41, N-5007 Bergen Norway, pp. 5803-5814.
Landgrafe, C., "Structure and Reactions of the Thioether Half-Sandwich Ruthenium(ii) Complexes [Ru(MeCN) 3 (9aneS3)][CF3SO3]2 and [Ru(MeCn)2(PPh3)([9]aneS3)][CF3SO3]2 ([9]aneS3 = 1,4,7-trithlacyclononane)", Journal of the Chemical Society, Dalton Transactions, an Interntional Journal of Inorganic Chemistry, 1994, The Royal Society of Chemistry, pp. 1885-1893.
Bengi, O. "Journal of Molecular Catalysts A: Chemical", 2013, Available Online, Elsevier, Hacettepe University, Department of Chemistry, Beytepe, Ankara, Turkey, pp. 53-62.
Wasilke, J., "Ruthenium Carbene Complexes Featuring a Tridentate Pincer-type Ligand", Organometallics 2005, 24, pp. 4289-4297.
Xianming, H. "Condensation of 2, 2'—Thiodiethanethiol with Benzaldehyde and Other Carbonyl Compounds (or Equivalents Thereof)", J. Chem. Soc., Perkin Trans. 1, 1004, 707-715.

* cited by examiner

*Primary Examiner* — Rip A Lee

(57) ABSTRACT

Novel transition metal complexes are provided which represent viable catalysts for a broad variety of reactions such as hydrogenation reactions and metathesis reactions. Novel preparation processes are made available via unprecedented routes inter alia not involving structures according to Grubbs I or Grubbs II catalysts.

17 Claims, 4 Drawing Sheets

Figure 1: Graph relating to Table 1, Ring Closing Metathesis of Diethyldiallylmalonate
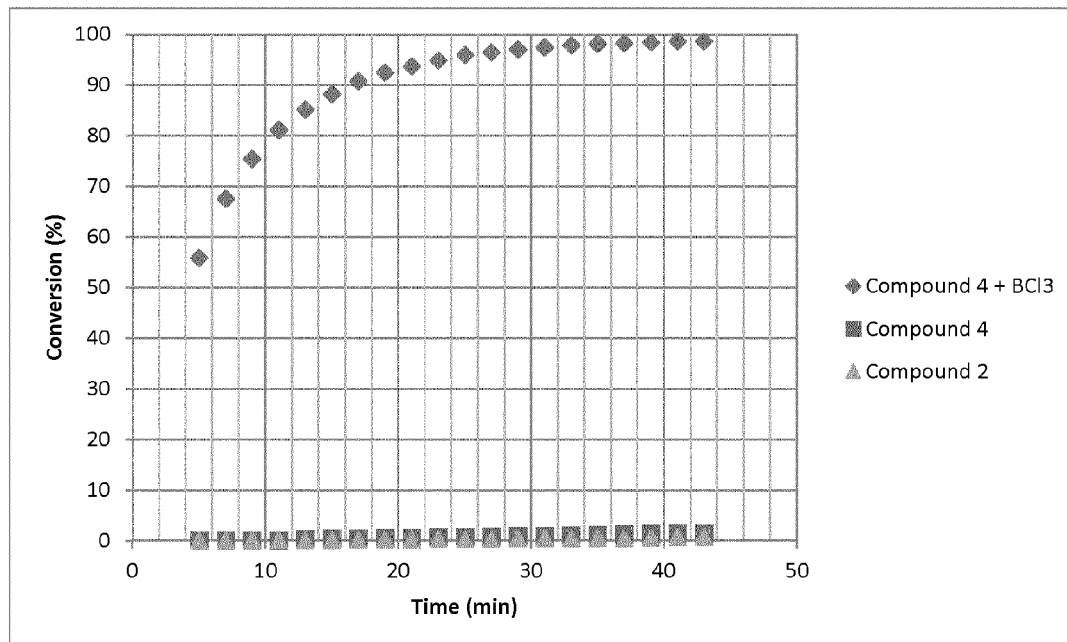
Figure 2: Graph relating to Table 2, ROMP of 1,5-cyclooctadiene
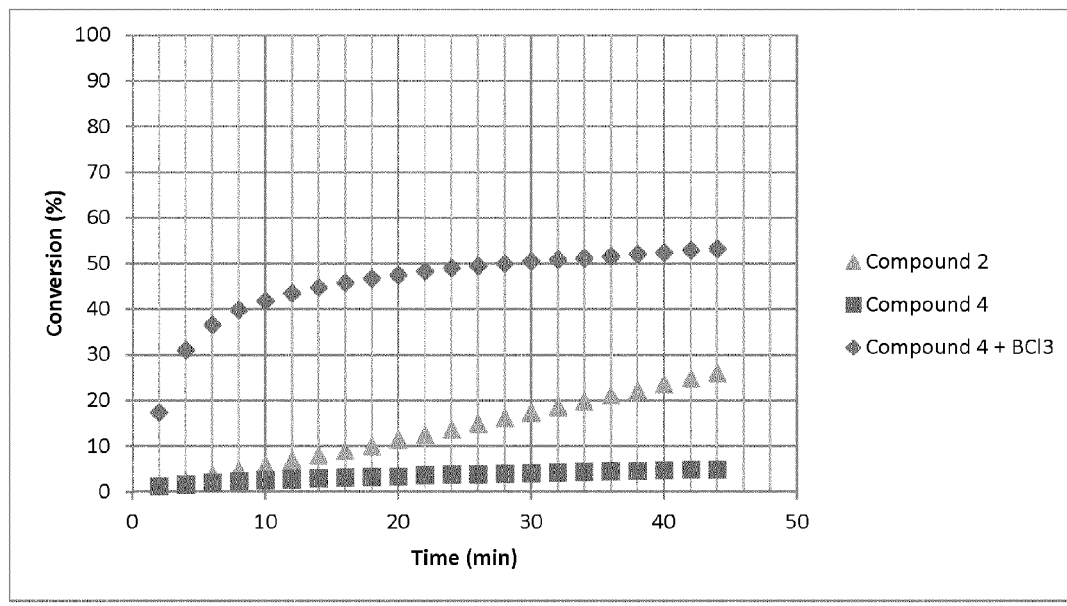

Figure 3: Graph relating to Table 3, Cross metathesis of 5-hexenyl acetate and methyl methacrylate
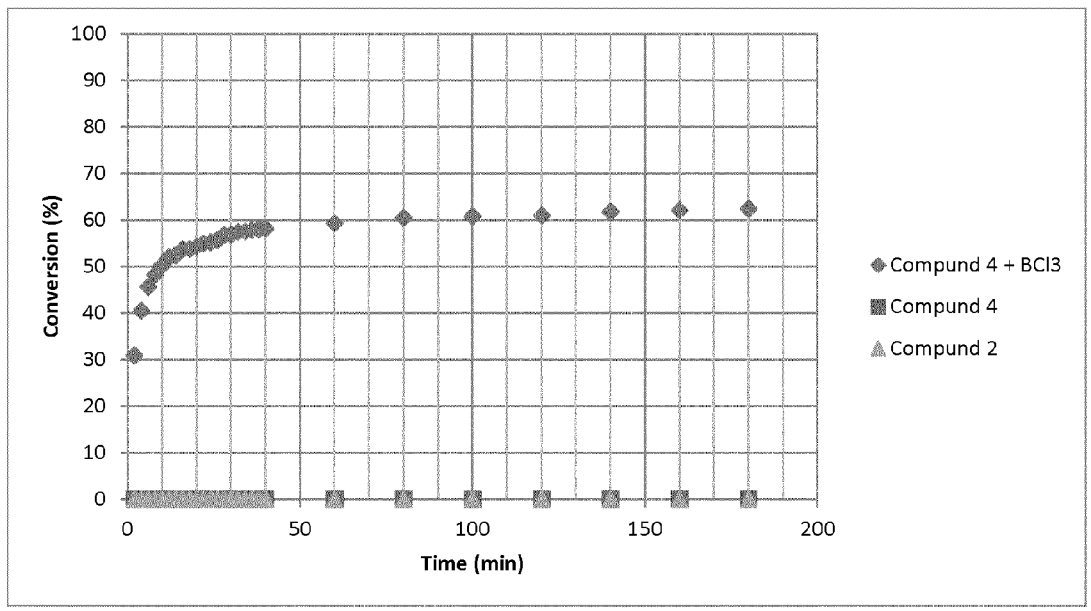
Figure 4: Graph relating to Table 4, Ring Closing Metathesis of Diethyl Diallylmalonate
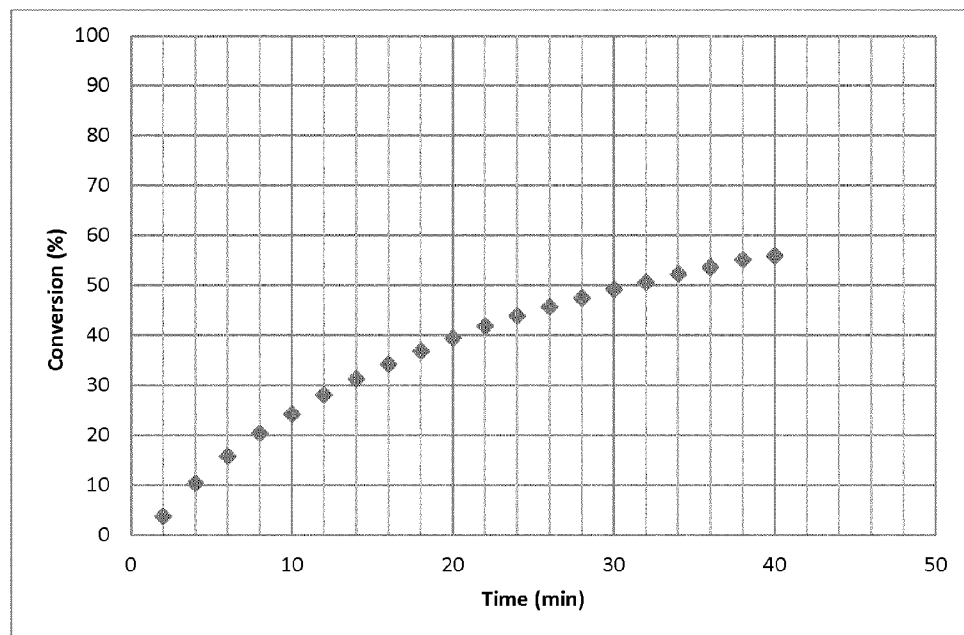

Figure 5: Graph relating to Table 5, Ring Opening Polymerization of 1,5-cyclooctadiene
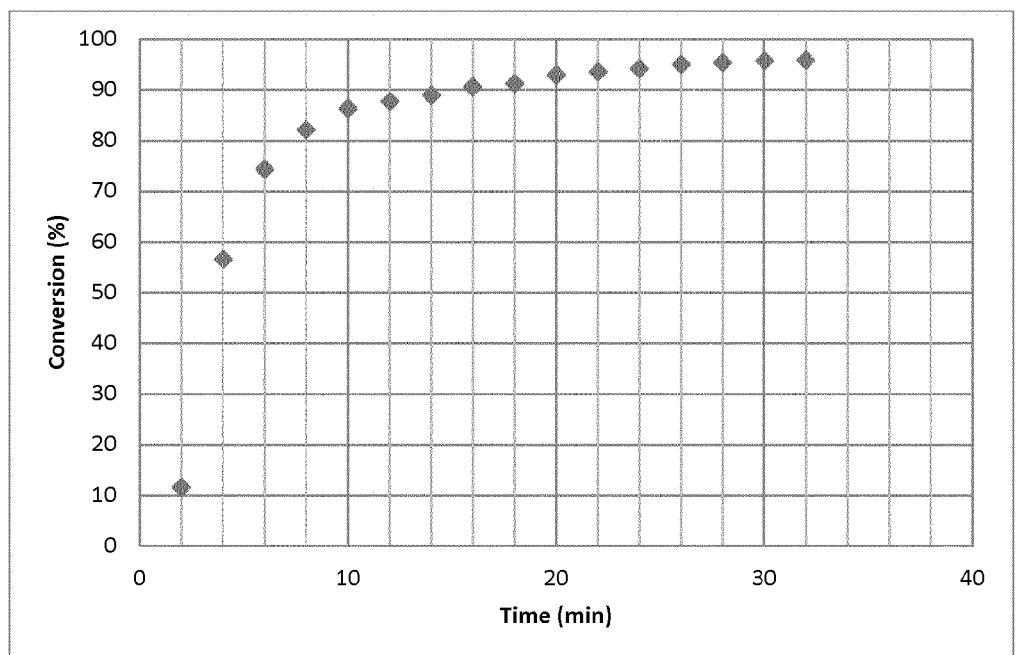
Figure 6: Graph relating to Table 6; cross metathesis of 5-hexenyl acetate and methyl methacrylate
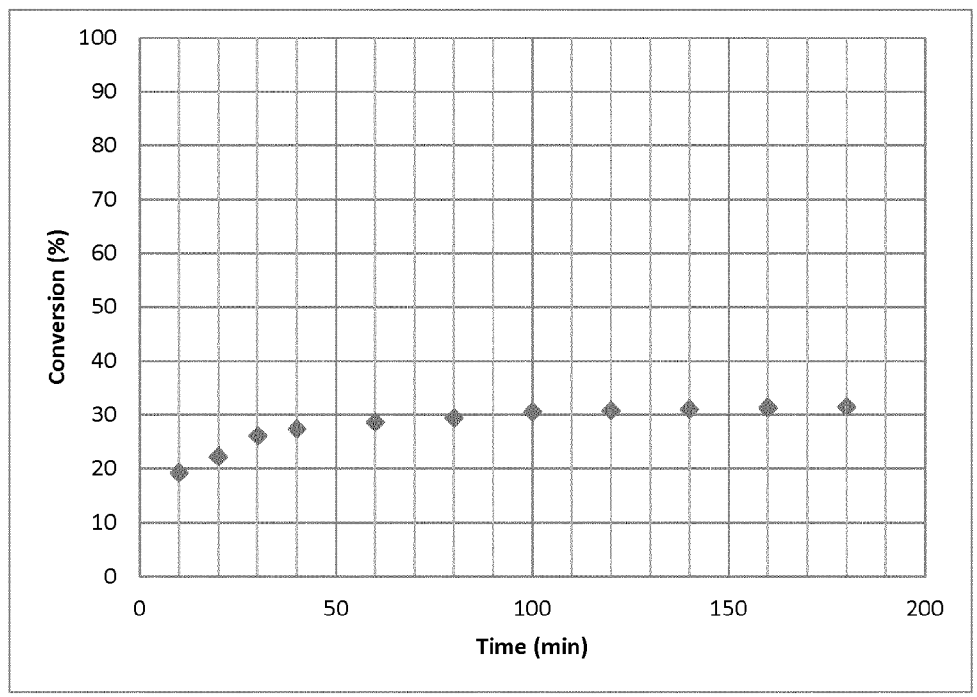

Figure 7: Graph relating to Table 7, Ring Closing Metathesis of Diethyl Diallylmalonate
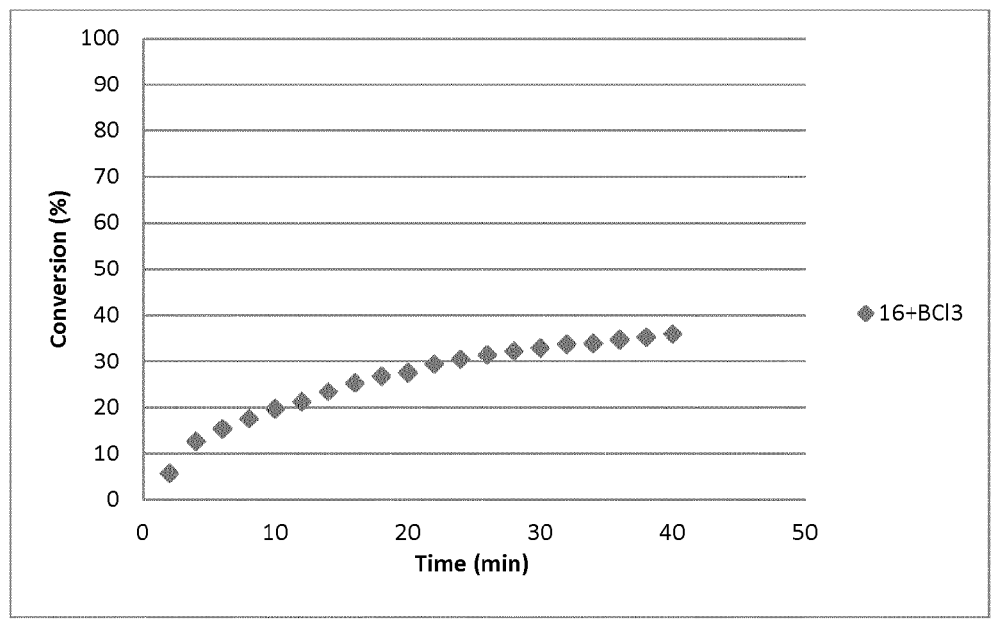

TRANSITION METAL COMPLEXES, THEIR PREPARATION AND USE

FIELD OF THE INVENTION

The present invention relates to novel transition metal complexes as well as novel transition metal complex catalysts, their preparation and their use, in particular for metathesis or hydrogenation reactions.

BACKGROUND OF THE INVENTION

Metathesis reactions are used widely in chemical syntheses, e.g. in the form of ring-closing metatheses (RCM), cross metatheses (CM), ring-opening metatheses (ROM), ring-opening metathesis polymerizations (ROMP), cyclic diene metathesis polymerizations (ADMET), self-metathesis, reaction of alkenes with alkynes (enyne reactions), polymerization of alkynes and olefinization of carbonyls. Metathesis reactions are employed, for example, for the synthesis of olefins, for ring-opening polymerization of norbornene derivatives, for the depolymerisation of unsaturated polymers and for the synthesis of telechelic polymers.

A broad variety of metathesis catalysts are known, inter alia, from WO-A-96/04289 and WO-A-97/06185. They often have the following general structure:

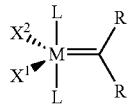

where M is osmium or ruthenium, the radicals R are identical or different organic radicals having a great structural variety, $X^1$ and $X^2$ are anionic ligands and the ligands L are uncharged electron-donors. In the literature, the term "anionic ligands" in the context of such metathesis catalysts always refers to ligands which, when being viewed separately from the metal centre, are negatively charged for a closed electron shell.

In the meantime it has been shown that certain transition metal complexes also show catalytic activity in hydrogenation reactions of various substrates.

Well-known metathesis catalysts are for example the so-called Grubbs catalysts like Grubbs I and Grubbs II catalysts.

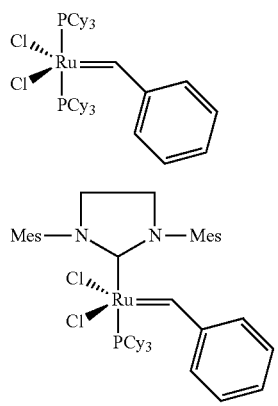

A lot of different catalysts have been developed and mostly the synthesis of such catalysts involves as one precursor the above mentioned Grubbs I or II catalysts.

In various publications ester hydrogenation catalysts are disclosed which all possess tridentate amino-phosphine ligands. Their preparation, however, is often extremely costly. Angew. Chem. Int. Ed. 2013, 52, 1-6 discloses the hydrogenation of low molecular weight carboxylic acid esters using different complex catalysts containing tridentate "SNS"-ligands as those shown in the following:

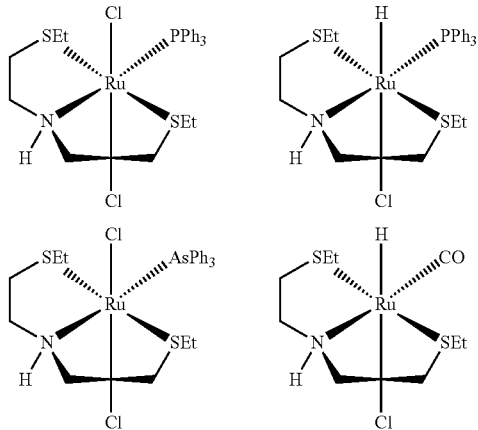

In Organometallics 2007, 26, 5803-5814 ruthenium alkylidene complexes of chelating amine ligands are disclosed. In particular two bidentate amino-benzyloxy ligands and two tridentate amino-bis(benzyloxy) ligands were prepared as well as ruthenium complexes containing such ligands as shown in the following scheme:

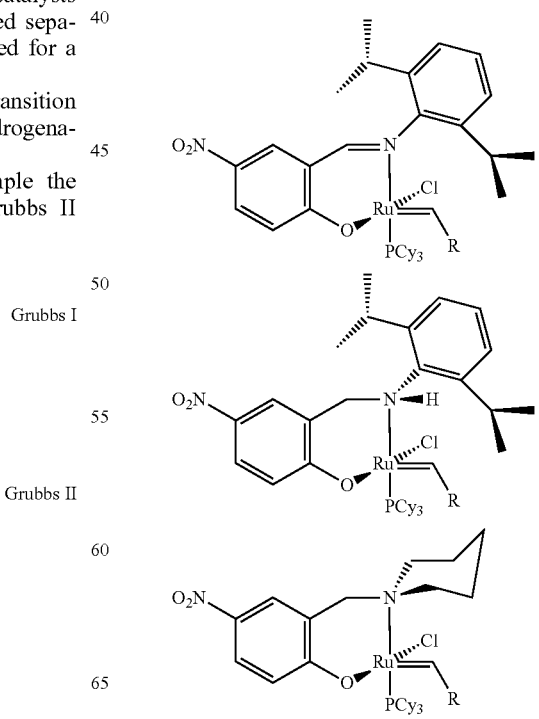

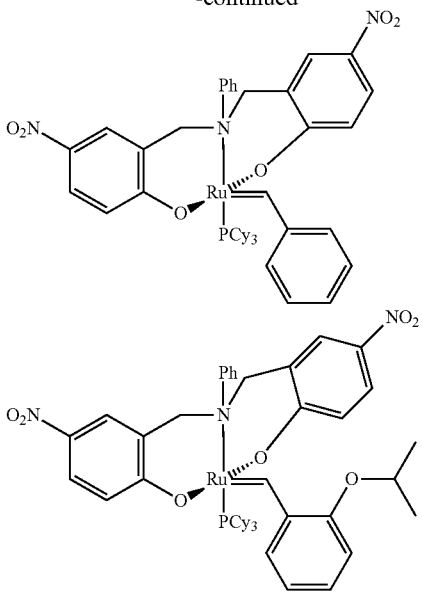

In Organometallics 2007, 26, 5803-5814 it is reported that the two catalysts bearing the tridentate [ONO] ligand display low thermal stability and low catalytic activity in RCM of diethylallylmalonate, i.e. a reasonably high conversion can be achieved only at very long reaction times (see Table 3). On the other hand Table 3 of the reference shows that metathesis activity of such catalysts increases upon addition of a Bronsted acid like HCl or $H_2SO_4$, however at the expense of an increased decomposition rate of the catalyst showing that the catalysts are less robust than desired.

In Organometallics 2005, 24, 4289-4297 Ruthenium based carbene complexes are disclosed which contain a bulky tridentate ligand, as e.g. the N,N'-bis(2,6-diisopropylphenyl)-2,6-pyridinedicarboxamide pincer ligand as [ONO] ligand. Such complexes are shown in the following scheme

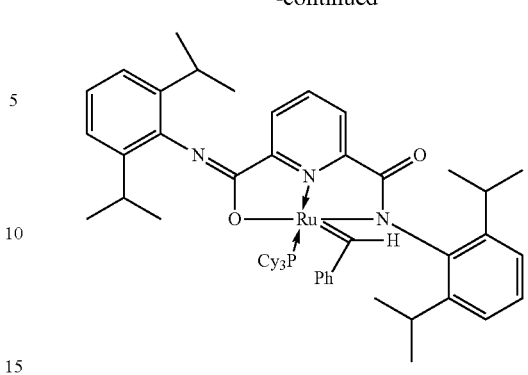

(4a)

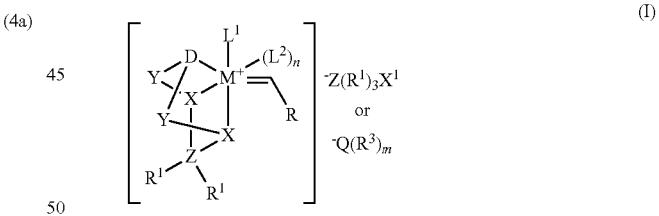

(4b)

(5)

In the ring closing metathesis of 1,7 octadiene to cyclohexene the triphenylphosphine stabilized [ONO] catalyst (4a) only showed low conversions. After 3 hours at 80° C. 76% product was observed as well as 24% isomers. Only a prolonged reaction time of up to 27 hours yielded conversion up to 98%. The presence of proton sources, i.e. Bronsted acids did not shown any influence on the catalyst activity while activation with Lewis acids even reduced the product yield drastically along with increased amounts of isomers.

Therefore, it was the object of the present invention to provide an active and robust, novel catalyst for a broad variety of reactions including metathesis and hydrogenation reactions. In particular the catalysts should not undergo a substantial decomposition under the reaction conditions and also provide acceptable conversions in reasonable reaction times compared to the slow reactions known from prior art for catalysts containing tridentate ligands.

SUMMARY OF THE INVENTION

Surprisingly novel transition metal complexes having general formula (I) could be provided $$\left[ \begin{array}{c} \text{structure} \end{array} \right] \quad \begin{array}{c} \text{-Z}(R^1)_3 X^1 \\ \text{or} \\ \text{-Q}(R^3)_m \end{array} \quad \text{(I)}$$

wherein
M means Ru, Os or Fe;
X means O or S;
D means S, O, $PR^2$, or $NR^2$ with $R^2$ meaning straight chain or branched $C_1$-$C_{14}$ alkyl, preferably straight chain or branched $C_1$-$C_6$ alkyl, $C_3$-$C_8$ cycloalkyl, preferably $C_3$-$C_6$ cycloalkyl, $C_6$-$C_{24}$ aryl, preferably phenyl;
Y means a divalent moiety, preferably unsubstituted or substituted $C_2$-$C_6$ alkylene, preferably 1,2-ethylene, 1,3-propylene, or 1,4-butylene, or a unsubstituted or substituted $C_6$-$C_{10}$ arylene group, preferably 1,2-phenylene or 2,3-napthylene;
R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;

$L^1$ means a ligand, preferably $P(R^2)_3$ wherein $R^2$ means unsubstituted or substituted, straight chain or branched $C_1$-$C_{14}$ alkyl, unsubstituted or substituted $C_6$-$C_{24}$ aryl, or unsubstituted or substituted $C_3$-$C_{20}$ cycloalkyl or an N-heterocyclic carbene ligand;

Z means B, Al, Ga, or In, preferably B;

$R^1$ are identical or different and represent F, Cl, Br, I, preferably Cl, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl;

$X^1$ means F, Cl, Br, or I.

$L^2$ is a two electron donor ligand, preferably $CH_3CN$, pyridine or tetrahydrofurane; and n is either 0 or 1, Q is either P, B, Al, As, Ga or Sb, preferably P or B, $R^3$ are identical or different and represent F, Cl, Br, I, preferably F, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl or ($C_6F_5$), and m is 4, 5 or 6, preferably 4 or 6.

Such transition metal complexes are feasible and viable catalysts for catalyzing different types of reactions, in particular metathesis reactions and hydrogenation reactions.

The invention further relates to a process for preparing the complexes according to general formula (I) comprising (1) reacting the complex of general formula (II)

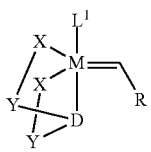

(II)

wherein

M means Ru, Os or Fe;

X means O or S;

D means S, O, $PR^2$, or $NR^2$ with $R^2$ meaning straight chain or branched $C_1$-$C_{14}$ alkyl, preferably straight chain or branched $C_1$-$C_6$ alkyl, $C_3$-$C_8$ cycloalkyl, preferably $C_5$-$C_6$ cycloalkyl, $C_6$-$C_{24}$ aryl, preferably phenyl;

Y means a divalent moiety, preferably unsubstituted or substituted $C_2$-$C_6$ alkylene, preferably 1,2-ethylene, 1,3-propylene, or 1,4-butylene, or a unsubstituted or substituted $C_6$-$C_{10}$ arylene group, preferably 1,2-phenylene or 2,3-napthylene;

R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;

$L^1$ means a ligand, preferably $P(R^2)_3$ wherein $R^2$ means unsubstituted or substituted, straight chain or branched $C_1$-$C_{14}$ alkyl, unsubstituted or substituted $C_6$-$C_{24}$ aryl, or unsubstituted or substituted $C_3$-$C_{20}$ cycloalkyl or an N-heterocyclic carbene ligand;

with a compound of general formula (III)

$ZX^1(R^1)_2$ (III)

wherein

Z means B, Al, Ga or In, preferably B;

$X^1$ means F, Cl, Br, or I; preferably Cl; and $R^1$ are identical or different and represent F, Cl, Br, I, preferably Cl, unsubstituted or substituted, straight chain or branched $C_1$-$C_{14}$—, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl;

resulting in a complex according to general formula (IV)

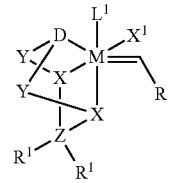

(IV)

wherein M, X, D, Y, R, $X^1$, and $R^1$ have the same meanings as outlined above for general formulae (II) and (III), and reacting the compound of general formula (IV) with a compound of general formula (Va)

$Z(R^1)_3$ (Va)

wherein

Z means B, Al, Ga or In; preferably B, and $R^1$ are identical or different and represent F, Cl, Br, I, preferably Cl, unsubstituted or substituted, straight chain or branched $C_1$-$C_{14}$—, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl;

or with a compound of general formula (Vb)

$GQ(R^3)_m$ (Vb)

wherein

G is K, Na, Li, Cs, Ag or Cu, preferably K,

Q is either P, B, Al, As, Ga or Sb, preferably P or B, $R^3$ are identical or different and represent F, Cl, Br, I, preferably F, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl or ($C_6F_5$), and m is 4, 5 or 6, preferably 4 or 6.

to obtain the complex catalyst according to general formula (I) with n being 0 and (2) optionally adding the ligand $L^2$ to obtain the complex catalyst according to general formula (I) with n being 1, wherein such ligand $L^2$ may be added simultaneously to the compound of general formula (Va) or (Vb) in step 2 or thereafter.

The invention further relates to novel transition metal complexes according to general formula (IV)

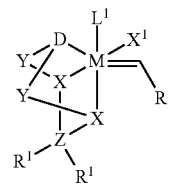

(IV)

wherein

M means Ru, Os or Fe;

X means O or S;

D means S, O, PR², or NR² with R² meaning straight chain or branched $C_1$-$C_{14}$ alkyl, preferably straight chain or branched $C_1$-$C_6$ alkyl, $C_3$-$C_8$ cycloalkyl, preferably $C_5$-$C_6$ cycloalkyl, $C_6$-$C_{24}$ aryl, preferably phenyl;

Y means a divalent moiety, preferably unsubstituted or substituted $C_2$-$C_6$ alkylene, preferably 1,2-ethylene, 1,3-propylene, or 1,4-butylene, or a unsubstituted or substituted $C_6$-$C_{10}$ arylene group, preferably 1,2-phenylene or 2,3-napthylene;

R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;

$L^1$ means a ligand, preferably $P(R^2)_3$ wherein $R^2$ means unsubstituted or substituted, straight chain or branched $C_1$-$C_{14}$ alkyl, unsubstituted or substituted $C_6$-$C_{24}$ aryl, or unsubstituted or substituted $C_3$-$C_{20}$ cycloalkyl or an N-heterocyclic carbene ligand;

Z means B, Al, Ga, or In, preferably B;

$R^1$ are identical or different and represent F, Cl, Br, I, preferably Cl, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl; and $X^1$ means F, Cl, Br, or I.

Such transition metal complexes according to general formula (IV) on the one hand are important intermediates in order to produce the inventive transition metal complexes according to general formula (I) and on the other hand are also viable catalysts for certain reactions, in particular hydrogenation reactions.

The invention further relates to novel transition metal complexes according to general formula (VI)

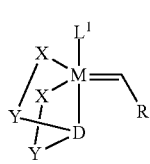

(VI)

wherein
M means Ru, Os or Fe;
X means O or S;
D means S, O, or PR² with R² meaning straight chain or branched $C_1$-$C_{14}$ alkyl, preferably straight chain or branched $C_1$-$C_6$ alkyl, $C_3$-$C_8$ cycloalkyl, preferably $C_5$-$C_6$ cycloalkyl, $C_6$-$C_{24}$ aryl, preferably phenyl;

Y means a divalent moiety, preferably unsubstituted or substituted $C_2$-$C_6$ alkylene, preferably 1,2-ethylene, 1,3-propylene, or 1,4-butylene, or a unsubstituted or substituted $C_6$-$C_{10}$ arylene group, preferably 1,2-phenylene or 2,3-napthylene;

R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;

$L^1$ means a ligand, preferably $P(R^2)_3$ wherein $R^2$ means unsubstituted or substituted, straight chain or branched $C_1$-$C_{14}$ alkyl, unsubstituted or substituted $C_6$-$C_{24}$ aryl, or unsubstituted or substituted $C_3$-$C_{20}$ cycloalkyl or an N-heterocyclic carbene ligand;

Such transition metal complexes according to general formula (VI) are important intermediates in order to produce the inventive transition metal complexes according to general formulae (I) and (IV).

The invention further relates to a novel process for preparing the transition metal complexes according to general formula (II) comprising reacting a compound of general formula (VII)

(VII)

wherein
X means O or S;
D means S, O, PR², or NR² with R² meaning straight chain or branched $C_1$-$C_{14}$ alkyl, preferably straight chain or branched $C_1$-$C_6$ alkyl, $C_3$-$C_8$ cycloalkyl, preferably $C_5$-$C_6$ cycloalkyl, $C_6$-$C_{24}$ aryl, preferably phenyl;

Y means a divalent moiety, preferably unsubstituted or substituted $C_2$-$C_6$ alkylene, preferably 1,2-ethylene, 1,3-propylene, or 1,4-butylene, or a unsubstituted or substituted $C_6$-$C_{10}$ arylene group, preferably 1,2-phenylene or 2,3-napthylene;

R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;

either with a M-based complex containing at least one $L^1$ ligand, preferably with a complex of general formula (VIII)

$M(L^1)_3(H)_2$ (VIII)

wherein
M is Ru, Os or Fe; and
$L^1$ means a ligand, preferably $P(R^2)_3$ wherein $R^2$ means substituted or unsubstituted, straight chain or branched $C_1$-$C_{14}$ alkyl, substituted or unsubstituted $C_6$-$C_{24}$ aryl, or substituted or unsubstituted $C_3$-$C_{20}$ cycloalkyl or an N-heterocyclic carbene ligand;

or with a $M^0$ complex, preferably with a $M^0$ complex of general formula (IX)

$M(L^3)_t$ (IX)

wherein
t is 2, 3, 4, 5, or 6 and
$L^3$ are identical or different and represent coordinated, straight chain or cyclic olefins and arenes, preferably cyclooctadiene and cyclooctatriene and with a ligand $L^1$ having the same meanings as given for general formula (VIII).

The invention further relates to a novel process for preparing transition metal complexes according to general formula (II) comprising reacting a compound of general formula (X)

(X)

wherein
M, R, $L^1$ shall have the same meanings as outlined for general formula (II) and $X^2$ are identical or different and represent an anionic ligand, preferably halide, more preferably F, Cl, Br or I, most preferably Cl;

with a compound of general formula (XI)

$$D[(Y\text{—}X)^-K^+]_2 \qquad (XI)$$

wherein

D, X, Y shall have the same meanings as outlined for general formula (II) and $K^+$ shall mean any mono charged cation or any equivalent therof, preferably an alkali metal cation, more preferably $Li^-$, $Na^+$ or $K^+$, or an earth alkali metal cation, more preferably $½Ca^{2+}$ or $½Mg^{2+}$ Furtheron the present invention relates to the use of the complexes according to general formula (I) as catalysts, preferably for converting C=C double bond containing substrates in metathesis reactions, more preferably ring-closing metatheses (RCM), cross-metatheses (CM) or a ring-opening metatheses (ROMP), or for hydrogenating C=C double bond containing substrates.

Furtheron the present invention relates to the use of the complexes according to general formula (IV) as catalysts, preferably for converting C=C double bond containing substrates in metathesis reactions, more preferably ring-closing metatheses (RCM), cross-metatheses (CM) or a ring-opening metatheses (ROMP), or for hydrogenating C=C double bond containing substrates.

In particular the present invention relates to a process for preparing compounds by subjecting a starting compound to a metathesis reaction or a hydrogenation reaction in the presence of a complex according to general formula (I) or (IV).

In particular the present invention relates to a process for preparing a nitrile rubber with a weight average molecular weight $M_w'$ by subjecting a starting nitrile rubber having a weight average molecular weight $M_w$ to a cross-metathesis reaction in the presence complex according to general formula (I), wherein the weight average molecular weight of the starting nitrile rubber $M_w$ is higher than the weight average molecular weight $M_w$ of the nitrile rubber prepared.

In particular the present invention relates to a process for preparing a nitrile rubber with a weight average molecular weight $M_w'$ by subjecting a starting nitrile rubber having a weight average molecular weight $M_w$ to a cross-metathesis reaction in the presence complex according to general formula (IV), wherein the weight average molecular weight of the starting nitrile rubber $M_w$ is higher than the weight average molecular weight $M_w$ of the nitrile rubber prepared.

In a further particular embodiment the present invention relates to a process for preparing partially or fully hydrogenated nitrile rubbers by hydrogenating a starting nitrile rubber in the presence of a complex having general formula (I).

In a further particular embodiment the present invention relates to a process for preparing partially or fully hydrogenated nitrile rubbers by hydrogenating a starting nitrile rubber in the presence of a complex having general formula (IV).

DRAWINGS

FIG. 1 contains the graph relating to Table 1 showing the conversion of the Ring Closing Metathesis of Diethyldiallylmalonate depending on the reaction time.

FIG. 2 contains the graph relating to Table 2 showing the conversion of Ring Opening Polymerization of 1,5-cyclooctadiene depending on the reaction time.

FIG. 3 contains the graph relating to Table 3 showing the conversion of the Cross Metathesis of 5-hexenyl acetate and methyl methacrylate depending on the reaction time.

FIG. 4 contains the graph relating to Table 4 showing the conversion of the Ring Closing Metathesis of Diethyldiallylmalonate depending on the reaction time.

FIG. 5 contains the graph relating to Table 5 showing the conversion of the Ring Opening Polymerization of 1,5-cyclooctadiene depending on the reaction time.

FIG. 6 contains the graph relating to Table 6 showing the conversion of the Cross Metathesis of 5-hexenyl acetate and methyl methacrylate depending on the reaction time.

FIG. 7 contains the graph relating to Table 7 showing the conversion of the Ring Closing Metathesis of diethyl diallyl malonate depending on the reaction time.

DETAILED DESCRIPTION OF THE INVENTION

The novel complexes according to general formula (I) are thermally robust and represent excellent catalysts which are suited for catalyzing on the one hand metathesis reactions of a broad variety of unsaturated substrates and on the other hand also hydrogenation reactions of a broad variety of unsaturated substrates of either low molecular weight or higher and high molecular weight like oligomers and polymers. Most importantly these novel complex catalysts according to general formula (I) are accessible via a cheap and safe route showing high yields. Favourably the preferred synthesis route does not necessarily involve the use of Grubbs-type structures, like Grubbs I catalyst.

The same applies to the novel complexes according to general formula (IV). Besides from being important intermediates for preparing the complexes according to general formula (I) as shown above they also represent thermally robust, active catalysts which are suited for catalyzing hydrogenation reactions of a broad variety of unsaturated substrates of either low molecular weight or higher and high molecular weight like oligomers and polymers. Like the complexes of general formula (I) they can be prepared with high conversions via different routes, preferably via converting compounds of general formula (VII) thereby avoiding the use of Grubbs-type structures, like Grubbs I catalyst.

The term "substituted" used for the purposes of the present patent application means that a hydrogen atom on an indicated radical or atom has been replaced by one of the groups indicated in each case, with the proviso that the valency of the atom indicated is not exceeded and the substitution leads to a stable compound.

For the purposes of the present patent application and invention, all the definitions of radicals, parameters or explanations given above or below in general terms or in preferred ranges can be combined with one another in any way, i.e. including combinations of the respective ranges and preferred ranges.

Surprisingly novel transition metal complexes having general formula (I) could be provided

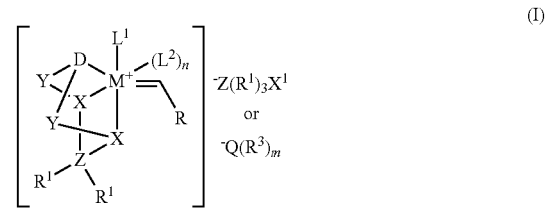

wherein

M means Ru, Os or Fe;

X means O or S;

D means S, O, $PR^2$, or $NR^2$ with $R^2$ meaning straight chain or branched $C_1$-$C_{14}$ alkyl, preferably straight chain or branched $C_1$-$C_6$ alkyl, $C_3$-$C_8$ cycloalkyl, preferably $C_3$-$C_6$ cycloalkyl, $C_6$-$C_{24}$ aryl, preferably phenyl;

Y means a divalent moiety, preferably unsubstituted or substituted $C_2$-$C_6$ alkylene, preferably 1,2-ethylene, 1,3-propylene, or 1,4-butylene, or a unsubstituted or substituted $C_6$-$C_{10}$ arylene group, preferably 1,2-phenylene or 2,3-napthylene;

R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;

$L^1$ means a ligand, preferably $P(R^2)_3$ wherein $R^2$ means unsubstituted or substituted, straight chain or branched $C_1$-$C_{14}$ alkyl, unsubstituted or substituted $C_6$-$C_{24}$ aryl, or unsubstituted or substituted $C_3$-$C_{20}$ cycloalkyl or an N-heterocyclic carbene ligand;

Z means B, Al, Ga, or In, preferably B;

$R^1$ are identical or different and represent F, Cl, Br, I, preferably Cl, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl;

$X^1$ means F, Cl, Br, or I.

$L^2$ is a two electron donor ligand, preferably $CH_3CN$, pyridine or tetrahydrofurane;

n is either 0 or 1;

Q is either P, B, Al, As, Ga or Sb, preferably P or B, $R^3$ are identical or different and represent F, Cl, Br, I, preferably F, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl or ($C_6F_5$), and m is 4, 5 or 6, preferably 4 or 6.

The general, preferred, more preferred, even more preferred and most preferred embodiments for the meanings of M, X, D, Y, R, $L^1$ in general formula (I), as provided above and in the following, shall apply not only to general formula (I) but also to all other general formulae (II) et seq. given in the present application to the extent the respective group or moiety occurs in such general formula. For the sake of a concise specification the manyfold repetition of such preferred, more preferred, even more preferred and most preferred embodiments for the meanings of M, X, D, Y, R, and $L^1$ in each general formula shall be avoided.

M represents Ru, Os or Fe, preferably Ru.

X means O or S.

D means S, O, $PR^2$, or $NR^2$ with $R^2$ meaning straight chain or branched $C_1$-$C_{14}$ alkyl, preferably straight chain or branched $C_1$-$C_6$ alkyl, $C_3$-$C_8$ cycloalkyl, preferably $C_5$-$C_6$ cycloalkyl, $C_6$-$C_{24}$ aryl, preferably phenyl.

Y means a divalent moiety, preferably unsubstituted or substituted $C_2$-$C_6$ alkylene, more preferably 1,2-ethylene, 1,3-propylene, or 1,4-butylene, most preferably 1,2-ethylene, or a unsubstituted or substituted $C_6$-$C_{10}$ arylene group, preferably 1,2-phenylene or 2,3-napthylene. Y can be substituted by one or more substituents, preferably selected from the group consisting of $SiZ_2CH_2$ or $SiZ_2CH_2CH_2$ with Z being $C_1$-$C_6$ alkyl or $C_1$-$C_6$ alkoxy.

R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;

Z means B, Al, Ga, or In, preferably B.

$R^1$ are identical or different and represent F, Cl, Br, I, preferably Cl, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl;

$X^1$ means F, Cl, Br, or I.

$L^2$ is a two electron donor ligand, preferably $CH_3CN$, pyridine or tetrahydrofurane; and n is either 0 or 1;

Q is either P, B, Al, As, Ga or Sb, preferably P or B, $R^3$ are identical or different and represent F, Cl, Br, I, preferably F, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl or ($C_6F_5$), and m is 4, 5 or 6, preferably 4 or 6.

$L^1$ means a ligand, preferably either $P(R^2)_3$ wherein $R^2$ are identical or different and represent straight chain or branched $C_1$-$C_{14}$ alkyl, preferably $C_1$-$C_8$ alkyl, $C_6$-$C_{24}$ aryl, $C_3$-$C_{20}$ cycloalkyl, each of which may be substituted or unsubstituted, or an N-heterocyclic carbene ligand.

If $L^1$ represents a ligand $P(R^2)_3$, $R^2$ are identical or different and preferably mean straight chain or branched $C_1$-$C_8$ alkyl, more preferably methyl, ethyl, n-propyl, iso-propyl, n-butyl, i-butyl, tert-butyl, or neopentyl, $C_6$-$C_{14}$ aryl, more preferably phenyl or naphthyl, or $C_3$-$C_{10}$ cycloalkyl, more preferably cyclopentyl or cyclohexyl wherein each of the aforementioned groups may be substituted by one or more substitutents more preferably selected from the group consisting of halogen, even more preferably F, Cl, Br or I, $SO_3Na$, $C_1$-$C_8$-alkyl, optionally substituted by one or more F, Cl, Br or I, $C_6$-$C_{14}$ aryl, more preferably phenyl or naphthyl, and $C_1$-$C_5$-alkoxy.

Most preferably $P(R^2)_3$ represents $PPh_3$, P(p-Tol)$_3$, P(o-Tol)$_3$, $PPh(CH_3)_2$, $P(CF_3)_3$, $P(p-FC_6H_4)_3$, $P(p-CF_3C_6H_4)_3$, $P(C_6H_4$—$SO_3Na)_3$, $P(CH_2C_6H_4$—$SO_3Na)_3$, $P(isopropyl)_3$, $P(CHCH_3(CH_2CH_3))_3$, $P(cyclopentyl)_3$, $P(cyclohexyl)_3$, $P(neopentyl)_3$ or $P(neophyl)_3$.

If $L^1$ represents a N-heterocyclic carbene ligand this is typically an imidazoline or imidazolidine ligand having a structure corresponding to the general formulae (IM-a), or (IM-b),

(IM-a)

(IM-b)

wherein $R^4$, $R^5$, $R^6$, $R^7$ are identical or different and are each hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-alkoxycarbonyl, $C_1$-$C_{20}$-alkylthio, $C_6$-$C_{20}$-arylthio, $C_1$-$C_{20}$-alkylsulphonyl, $C_1$-$C_{20}$-alkylsulphonate, $C_6$-$C_{20}$-arylsulphonate or $C_1$-$C_{20}$-alkylsulphinyl or in the alternative $R^6$ and $R^7$ have the above mentioned meanings and at the same time $R^4$ and $R^5$ jointly form a $C_6$-$C_{10}$ cyclic structure together with the two adjacent carbon atoms in the imidazoline or imidazolidine ring.

One or more of the substituents $R^4$, $R^5$, $R^6$, $R^7$ can, if appropriate, independently of one another, be substituted by one or more substituents, preferably straight-chain or branched $C_1$-$C_{10}$-alkyl, $C_3$-$C_8$-cycloalkyl, $C_1$-$C_{10}$-alkoxy or $C_6$-$C_{24}$-aryl, where these abovementioned substituents may in turn be substituted by one or more functional groups, preferably functional groups selected from the group consisting of halogen, in particular chlorine or bromine, $C_1$-$C_5$-alkyl, $C_1$-$C_5$-alkoxy and phenyl.

Merely for the sake of clarity, it may be added that the structures of the imidazoline or imidazolidine ligands depicted in the general formulae (IM-a) and (IM-b) in the present application are equivalent to the structures (IM-a'), and (IM-b') which are frequently also found in the literature for this type of ligands and emphasize the carbene character of the imidazoline or imidazolidine ligand. This applies analogously to the associated preferred structures (VIII-a)-(VIII-o) depicted below.

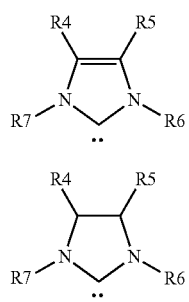

(IM-a')

(IM-b')

In a preferred embodiment of the catalysts of the general formula (I), $R^4$ and $R^5$ are each, independently of one another, hydrogen, $C_6$-$C_{24}$-aryl, particularly preferably phenyl, straight-chain or branched $C_1$-$C_{10}$-alkyl, particularly preferably propyl or butyl, or together with the carbon atoms to which they are bound form a $C_6$-$C_{10}$ cycloalkyl or $C_6$-$C_{10}$ aryl substituent, preferably a phenyl ring in structure (IM-a) (structure (IM-a') respectively) where all the above mentioned substituents may in turn be substituted by one or more further substituents selected from the group consisting of straight-chain or branched $C_1$-$C_{10}$-alkyl, $C_1$-$C_{10}$-alkoxy, $C_6$-$C_{24}$-aryl and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen.

In preferred embodiment of the catalysts of the general formula (I), the substituents $R^6$ and $R^7$ are identical or different and are each straight-chain or branched $C_1$-$C_{10}$-alkyl, particularly preferred i-propyl or neopentyl, $C_3$-$C_{10}$-cycloalkyl, particularly preferred adamantyl, $C_6$-$C_{24}$-aryl, particularly preferred phenyl, $C_1$-$C_{10}$-alkylsulphonate, particularly preferred methanesulphonate, $C_6$-$C_{10}$-arylsulphonate, particularly preferred p-toluenesulphonate.

The abovementioned substituents as meanings of $R^6$ and $R^7$ may be substituted by one or more further substituents selected from the group consisting of straight-chain or branched $C_1$-$C_5$-alkyl, in particular methyl, $C_1$-$C_5$-alkoxy, optionally substituted aryl and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen.

In particular, the substituents $R^6$ and $R^7$ can be identical or different and are each i-propyl, neopentyl, adamantyl, mesityl or 2,6-diisopropylphenyl.

Particularly preferred imidazoline or imidazolidine ligands have the following structures (VIII-a) to (VIII-o), where Ph is in each case a phenyl substituent, Bu is a butyl substituent, Mes is in each case a 2,4,6-trimethylphenyl substituent and $(iPr)_2Ph$ is in all cases 2,6-diisopropylphenyl.

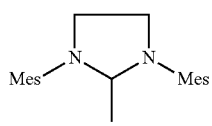
(VIII-a)

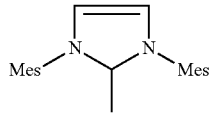
(VIII-b)

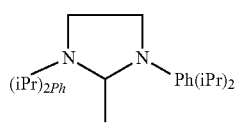
(VIII-c)

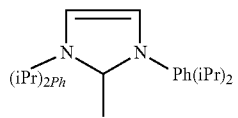
(VIII-d)

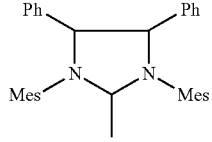
(VIII-e)

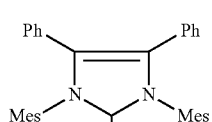
(VIII-f)

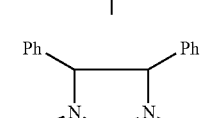
(VIII-g)

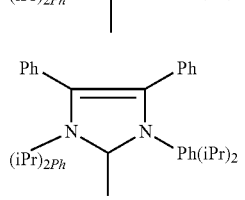
(VIII-h)

-continued

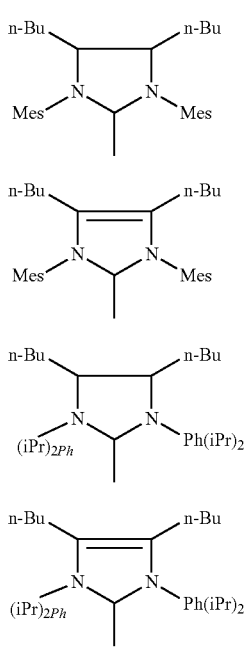

(VIII-k)

(VIII-m)

(VIII-n)

(VIII-o)

Preferred Definitions of General Formula (I):

In a preferred embodiment complexes of general formula (I) are provided in which M means Ru X means O or S;

D means S, O, $PR^2$, or $NR^2$ with $R^2$ meaning straight chain or branched $C_1$-$C_6$ alkyl, preferably $C_5$-$C_6$ cycloalkyl, $C_6$-$C_{14}$ aryl, preferably phenyl.

Y means a divalent moiety, preferably unsubstituted or substituted $C_2$-$C_6$ alkylene, more preferably 1,2-ethylene, 1,3-propylene, or 1,4-butylene, most preferably 1,2-ethylene, or a unsubstituted or substituted $C_6$-$C_{10}$ arylene group, preferably 1,2-phenylene or 2,3-napthylene;

R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;

$L^1$ means either $P(R^2)_3$ wherein $R^2$ are identical or different and preferably mean straight chain or branched $C_1$-$C_8$ alkyl, more preferably methyl, ethyl, n-propyl, isopropyl, n-butyl, i-butyl, tert-butyl, or neopentyl, $C_6$-$C_{14}$ aryl, more preferably phenyl or naphthyl, or $C_3$-$C_{10}$ cycloalkyl, more preferably cyclopentyl or cyclohexyl wherein each of the aforementioned groups may be substituted by one or more substitutents more preferably selected from the group consisting of halogen, even more preferably F, Cl, Br or I, $SO_3Na$, $C_1$-$C_8$-alkyl, the latter either unsubstituted or substituted by one or more F, Cl, Br or I, $C_6$-$C_{14}$ aryl, more preferably phenyl or naphthyl, and $C_1$-$C_3$-alkoxy.

an N-heterocyclic carbene ligand of general formulae (IM-a) or (IM-b)

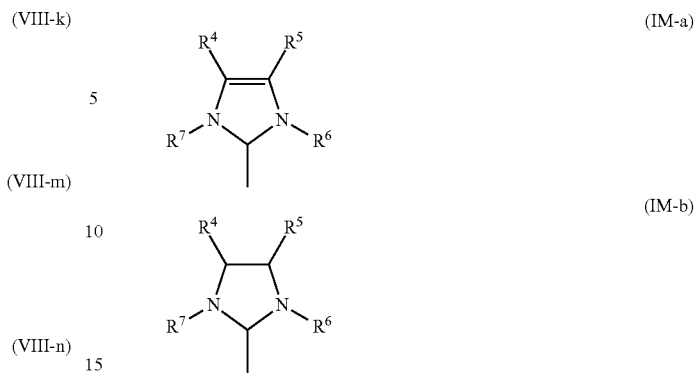

(IM-a)

(IM-b)

wherein $R^4$, $R^5$, $R^6$, $R^7$ are identical or different and are each hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_1$-$C_{20}$-carboxylate, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-alkoxycarbonyl, $C_1$-$C_{20}$-alkylthio, $C_6$-$C_{20}$-arylthio, $C_1$-$C_{20}$-alkylsulphonyl, $C_1$-$C_{20}$-alkylsulphonate, $C_6$-$C_{20}$-arylsulphonate or $C_1$-$C_{20}$-alkylsulphinyl;

or in the alternative $R^6$ and $R^7$ have the above mentioned meanings and at the same time $R^4$ and $R^5$ jointly form a $C_6$-$C_{10}$ cyclic structure together with the two adjacent carbon atoms in the imidazoline or imidazolidine ring;

Z means B, Al, Ga, or In, preferably B;

$R^1$ are identical or different and represent F, Cl, Br, I, preferably Cl, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl;

$X^1$ means F, Cl, Br, or I.

$L^2$ is a two electron donor ligand, preferably $CH_3CN$, pyridine or tetrahydrofurane;

n is either 0 or 1,

Q is either P, B, Al, As, Ga or Sb, preferably P or B, $R^3$ are identical or different and represent F, Cl, Br, I, preferably F, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl or ($C_6F_5$), and m is 4, 5 or 6, preferably 4 or 6.

In an even more preferred embodiment complexes of general formula (I) are provided in which M means Ru X means O or S;

D means S, O, $PR^2$, or $NR^2$ with $R^2$ meaning straight chain or branched $C_1$-$C_6$ alkyl, most preferably $C_5$-$C_6$ cycloalkyl, $C_6$-$C_{14}$ aryl, most preferably phenyl.

Y means 1,2-ethylene or 1,2-phenyl;

R means phenyl with none, 1, 2, 3, 4, or 5 substituents selected from the group consisting of F, Cl, Br, and I $L^1$ is selected from the group consisting of $PPh_3$, $P(p$-$Tol)_3$, $P(o$-$Tol)_3$, $PPh(CH_3)_2$, $P(CF_3)_3$, $P(p$-$FC_6H_4)_3$, $P(p$-$CF_3C_6H_4)_3$, $P(C_6H_4$—$SO_3Na)_3$, $P(CH_2C_6H_4$—$SO_3Na)_3$, $P(isopropyl)_3$, $P(CHCH_3(CH_2CH_3))_3$, $P(cyclopentyl)_3$, $P(cyclohexyl)_3$, $P(neopentyl)_3$, $P(neophyl)_3$, and an N-heterocyclic carbene ligand of general formulae (IM-a) or (IM-b), wherein $R^6$ and $R^7$ are identical or different and represent i-propyl, neopentyl, adamantyl, mesityl or 2,6- diisopropylphenyl, and $R^4$ and $R^5$ are identical or different and represent hydrogen, $C_6$-$C_{24}$-aryl, particularly preferably phenyl, straight-chain or branched $C_1$-$C_{10}$-alkyl, particularly preferably propyl or butyl, or together with the carbon atoms to which they are bound form a $C_6$-$C_{10}$ cycloalkyl or $C_6$-$C_{10}$ aryl substituent, preferably a phenyl ring;

Z means B, Al, Ga, or In;

$R^1$ are identical or different and represent F, Cl, Br, I, and are most preferably identical and Cl;

$X^1$ means F, Cl, Br, or I, most preferably Cl;

$L^2$ represents $CH_3CN$, pyridine or tetrahydrofurane;

n is either 0 or 1,

Q is either P, B, Al, As, Ga or Sb, preferably P or B, $R^3$ are identical or different and represent F, Cl, Br, I, preferably F, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl or ($C_6F_5$), and m is 4, 5 or 6, preferably 4 or 6.

In a most preferred embodiment complexes of general formula (I) are provided in which M means Ru X means O or S;

D means S, O, $PR^2$, or $NR^2$ with $R^2$ meaning straight chain or branched $C_1$-$C_6$ alkyl, most preferably $C_5$-$C_6$ cycloalkyl, $C_6$-$C_{14}$ aryl, most preferably phenyl.

Y means 1,2-ethylene or 1,2-phenyl;

R means phenyl with none or 5 substituents selected from the group consisting of F, Cl, Br, and I;

$L^1$ is selected from the group consisting of $PPh_3$, $P(p\text{-Tol})_3$, $P(o\text{-Tol})_3$, $PPh(CH_3)_2$, $P(CF_3)_3$, $P(p\text{-}FC_6H_4)_3$, $P(p\text{-}CF_3C_6H_4)_3$, $P(C_6H_4\text{—}SO_3Na)_3$, $P(CH_2C_6H_4\text{—}SO_3Na)_3$, $P(\text{isopropyl})_3$, $P(CHCH_3(CH_2CH_3))_3$, $P(\text{cyclopentyl})_3$, $P(\text{cyclohexyl})_3$, $P(\text{neopentyl})_3$, $P(\text{neophyl})_3$, and an N-heterocyclic carbene ligand of the structures (VIII-a) to (VIII-o);

Z means B;

$R^1$ are identical and represent Cl;

$X^1$ means Cl;

$L^2$ represents $CH_3CN$, pyridine or tetrahydrofurane;

n is either 0 or 1,

Q is either P, B, Al, As, Ga or Sb, preferably P or B, $R^3$ are identical or different and represent F, Cl, Br, I, preferably F, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl or ($C_6F_5$), and m is 4, 5 or 6, preferably 4 or 6.

The invention further relates to a process for preparing the complexes according to general formula (I) comprising (1) reacting the complex of general formula (II)

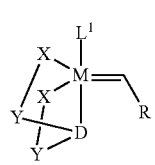

(II)

wherein

M means Ru, Os or Fe;

X means O or S;

D means S, O, $PR^2$, or $NR^2$ with $R^2$ meaning straight chain or branched $C_1$-$C_{14}$ alkyl, preferably straight chain or branched $C_1$-$C_6$ alkyl, $C_3$-$C_8$ cycloalkyl, preferably $C_5$-$C_6$ cycloalkyl, $C_6$-$C_{24}$ aryl, preferably phenyl;

Y means a divalent moiety, preferably unsubstituted or substituted $C_2$-$C_6$ alkylene, preferably 1,2-ethylene, 1,3-propylene, or 1,4-butylene, or a unsubstituted or substituted $C_6$-$C_{10}$ arylene group, preferably 1,2-phenylene or 2,3-napthylene;

R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;

$L^1$ means a ligand, preferably $P(R^2)_3$ wherein $R^2$ means unsubstituted or substituted, straight chain or branched $C_1$-$C_{14}$ alkyl, unsubstituted or substituted $C_6$-$C_{24}$ aryl, or unsubstituted or substituted $C_3$-$C_{20}$ cycloalkyl or an N-heterocyclic carbene ligand;

with a compound of general formula (III)

wherein

Z means B, Al, Ga or In, preferably B;

$X^1$ means F, Cl, Br, or I; preferably Cl; and $R^1$ are identical or different and represent F, Cl, Br, I, preferably Cl, unsubstituted or substituted, straight chain or branched $C_1$-$C_{14}$—, preferably $C_1$-$C_6$ alkyl, $C_3$-$C_8$ cycloalkyl, preferably $C_3$-$C_6$ cycloalkyl, unsubstituted or substituted $C_6$-$C_{24}$ aryl, preferably phenyl;

resulting in a complex according to general formula (IV)

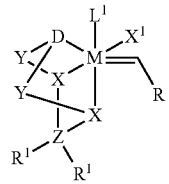

(IV)

wherein M, X, D, Y, R, $X^1$, and $R^1$ have the same meanings as outlined above for general formulae (II) and (III), and reacting the compound of general formula (IV) with a compound of general formula (Va)

wherein

Z means B, Al, Ga or In; preferably B, and $R^1$ are identical or different and represent F, Cl, Br, I, preferably Cl, unsubstituted or substituted, straight chain or branched $C_1$-$C_{14}$—, preferably $C_1$-$C_6$ alkyl, $C_3$-$C_8$ cycloalkyl, preferably $C_3$-$C_6$ cycloalkyl, unsubstituted or substituted $C_6$-$C_{24}$ aryl, preferably phenyl;

or reacting the compound of general formula (IV) with a compound of general formula (Vb)

wherein

G is K, Na, Li, Cs, Ag or Cu, preferably K,

Q is either P, B, Al, As, Ga or Sb, preferably P or B, $R^3$ are identical or different and represent F, Cl, Br, I, preferably F, unsubstituted or substituted, straight chain or branched $C_1$-$C_{14}$ alkyl, preferably $C_1$-$C_6$ alkyl, $C_3$-$C_8$ cycloalkyl, preferably $C_5$-$C_6$ cycloalkyl, unsubstituted or substituted $C_6$-$C_{24}$ aryl, preferably phenyl or ($C_6F_5$), and m is 4, 5 or 6, preferably 4 or 6.

to obtain the complex catalyst according to general formula (I) with n being 0 and (2) optionally adding the ligand $L^2$ to obtain the complex catalyst according to general formula (I) with n being 1, wherein such ligand $L^2$ may be added simultaneously to the compound of general formula (Va) or (Vb) in step 2 or thereafter.

The above described synthesis of the complexes of general formula (I) is summarized in the following scheme:

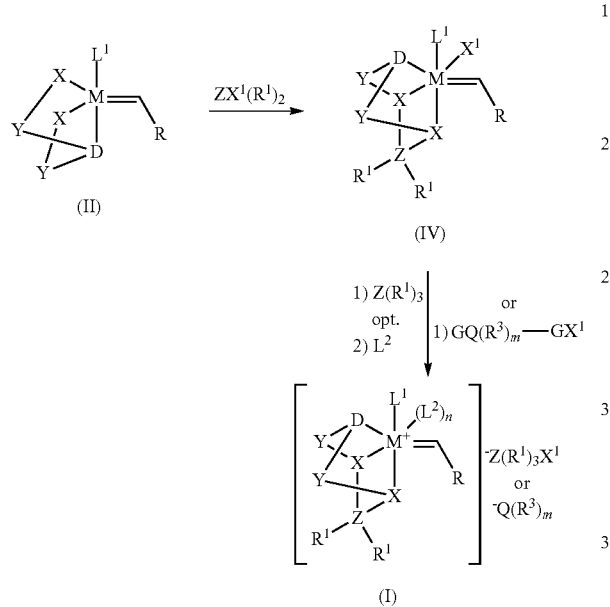

wherein M, X, D, Y, R, $L^1$, Z, $R^1$, $L^2$, Q, $R^3$, m and n have the same general, preferred, more preferred and most preferred meanings as outlined above.

In the first step of such activation reaction the Lewis acid $ZX^1(R^1)_2$ containing a halogen transfers the halide to the metal and bridges between the two X ligands. Secondly, the halogen which was transferred to the metal is abstracted by the second Lewis acid, $Z(R^1)_3$ to generate a cationic metal-alkylidene complex which is active for olefin metathesis.

Reaction Conditions for Synthesis of Complexes of General Formula (I):

Such synthesis of the complexes of general formula (I) starting from complexes of general formula (II) is typically carried out in an organic solvent, preferably, dichloromethane and at temperatures in the range of 5 to 50° C., preferably of from 10 to 40° C. Step 1 and step 2 are typically carried out in the same solvent. The compounds of general (III) and (Va) may be identical or different, preferably they are identical. In step (1) the complex of general formula (II) and the Lewis acid (III), $ZX^1(R^1)_2$, are preferably used in an equimolar ratio. In step (2) the complex of general formula (IV) and the Lewis acid (Va), $Z(R^1)_3$, or (Vb) $GQ(R^3)_m$ are used in a molar ratio of 1:(1-2), preferably 1:1. In case the Lewis acid (III), $Z(R^1)_3$, is the same as Lewis acid (Va), $ZX^1(R^1)_2$, this reaction can also be performed in one step only, with the molar ratio of the complex of general formula (II) to the $ZX^1(R^1)_2$ is 1: (2-3), preferably 1: (2). The complexes of formula (I) obtained after such process can be used in situ as catalysts, i.e. without isolating them. In the alternative a ligand $L^2$ can be added and the resulting complex with n being 1 can then be isolated.

Typical embodiments of the process for preparing complexes of general formula (I) are:

Embodiment 1

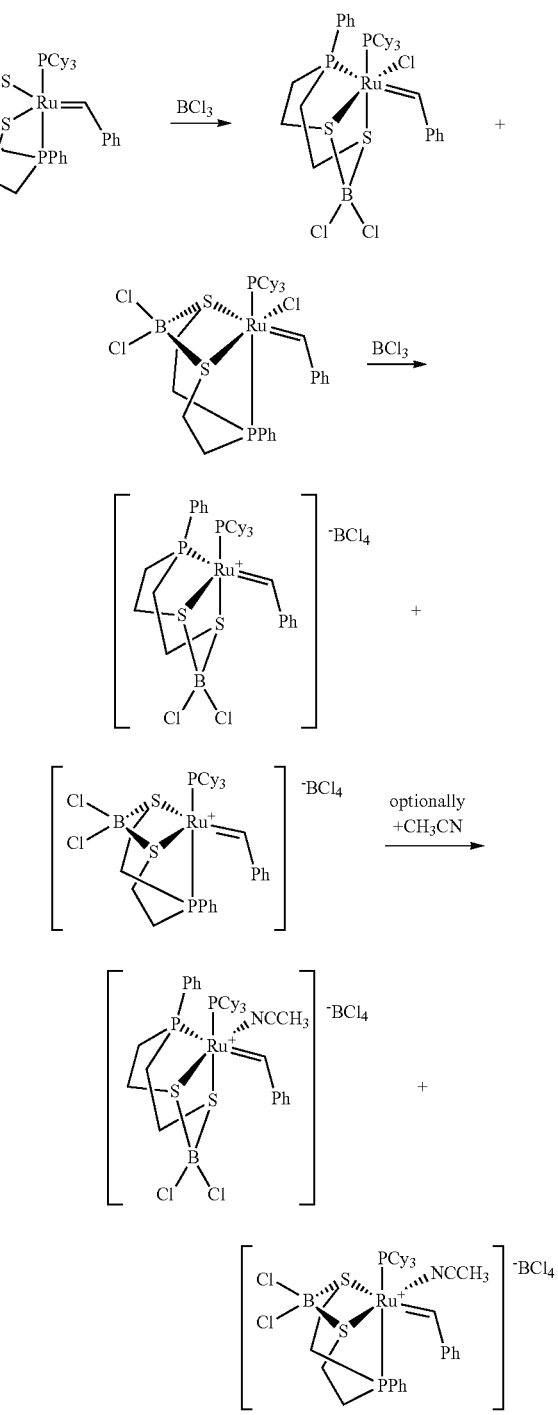

Embodiment 2
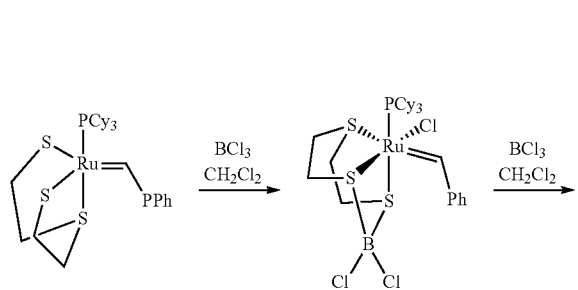
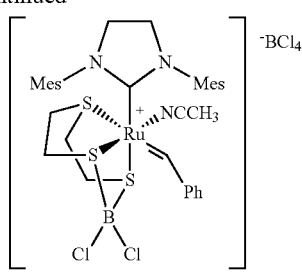
Embodiment 4
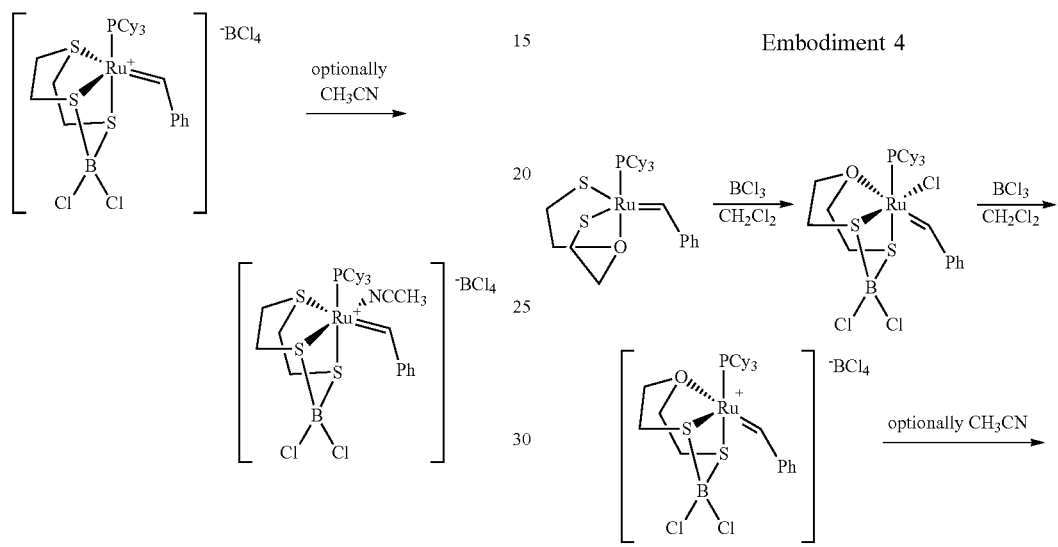
Embodiment 3
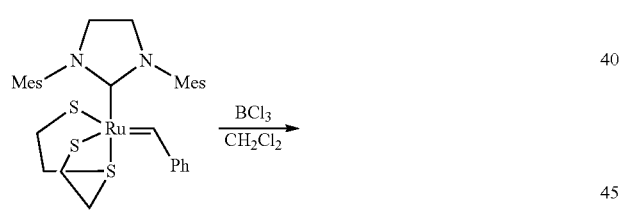
Embodiment 5
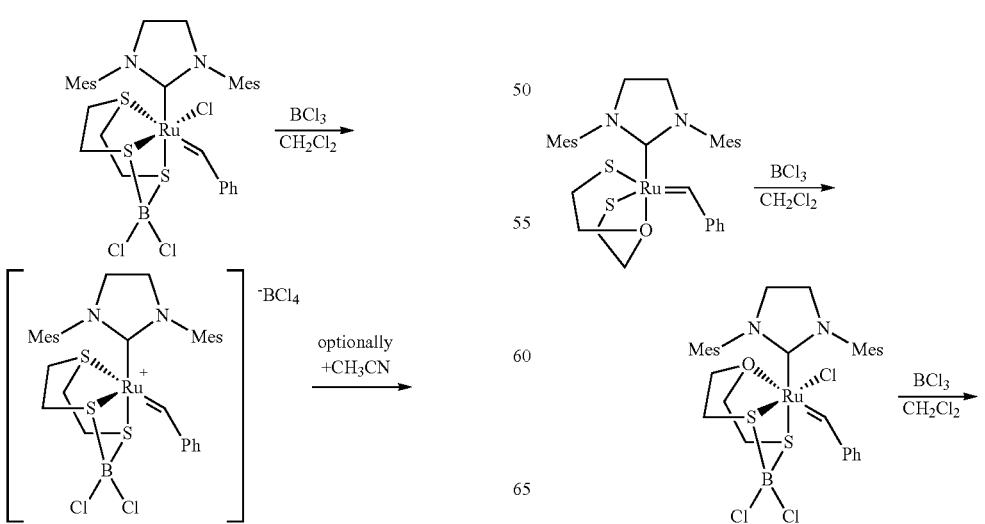

23
-continued
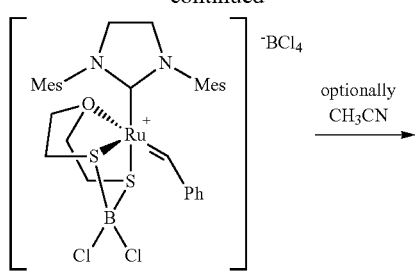
24
Embodiment 7
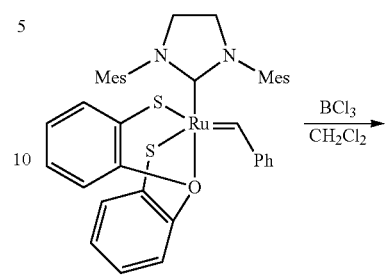
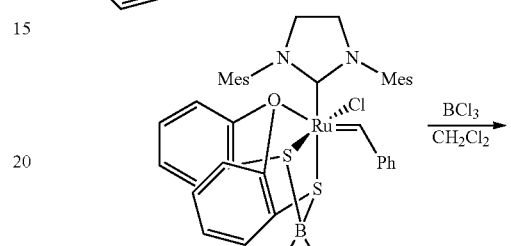
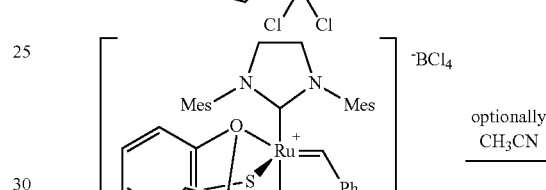
Embodiment 6
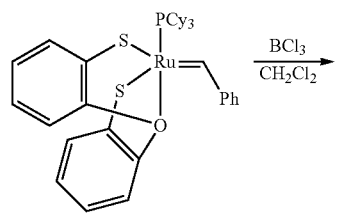
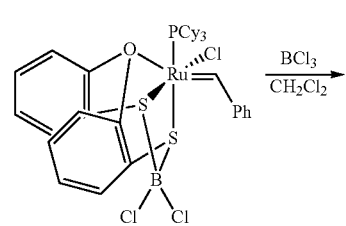
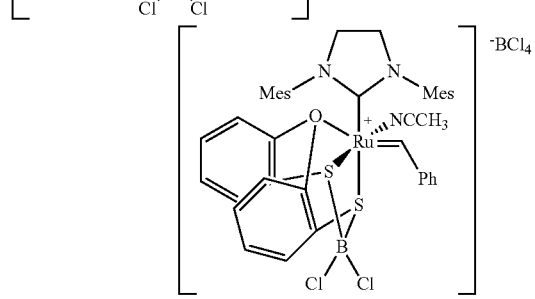
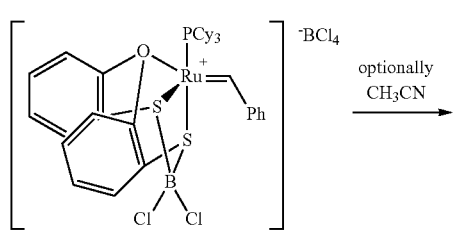
Embodiment 8
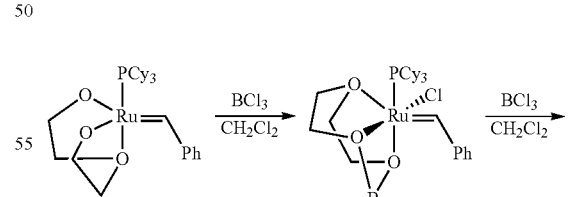
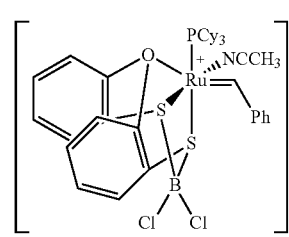
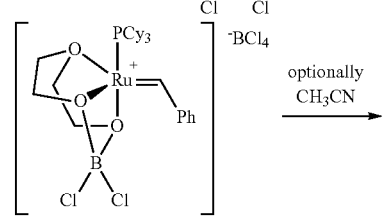

-continued

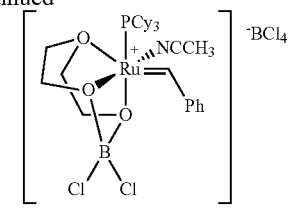

Embodiment 9

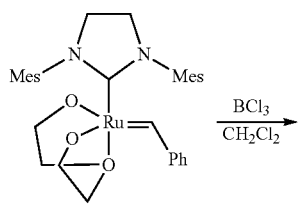

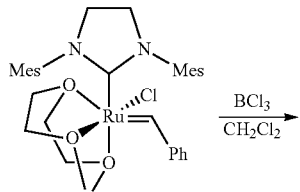

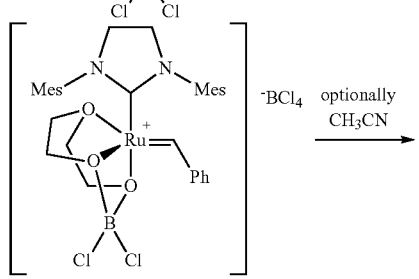

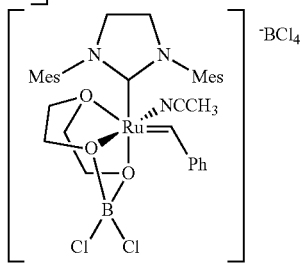

Embodiment 10

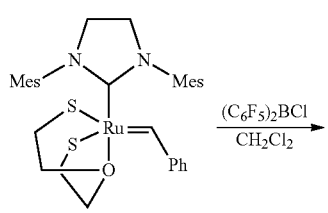

-continued

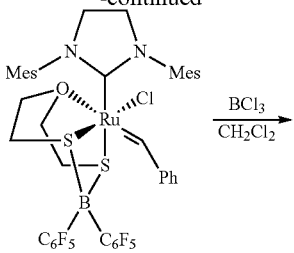

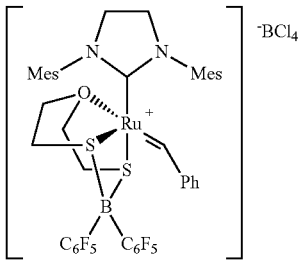

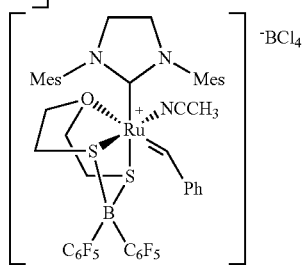

The invention further relates to novel transition metal complexes according to general formula (VI)

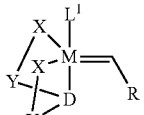

(VI)

wherein
M means Ru, Os or Fe;
X means O or S;
D means S, O, or $PR^2$ with $R^2$ meaning straight chain or branched $C_1$-$C_{14}$ alkyl, preferably straight chain or branched $C_1$-$C_6$ alkyl, $C_3$-$C_8$ cycloalkyl, preferably $C_3$-$C_6$ cycloalkyl, $C_6$-$C_{24}$ aryl, preferably phenyl;
Y means a divalent moiety, preferably unsubstituted or substituted $C_2$-$C_6$ alkylene, preferably 1,2-ethylene, 1,3-propylene, or 1,4-butylene, or a unsubstituted or substituted $C_6$-$C_{10}$ arylene group, preferably 1,2-phenylene or 2,3-napthylene;
R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;
$L^1$ means a ligand, preferably $P(R^2)_3$ wherein $R^2$ means unsubstituted or substituted, straight chain or branched $C_1$-$C_{14}$ alkyl, unsubstituted or substituted $C_6$-$C_{24}$ aryl, or unsubstituted or substituted $C_3$-$C_{20}$ cycloalkyl or an N-heterocyclic carbene ligand;
The invention further relates to two different processes for preparing the transition metal complexes according to general formula (II) which are hereinafter also referred to as Route A and Route B.

Route A:

Route A represents a novel process for preparing the transition metal complexes according to general formula (II) comprising reacting a compound of general formula (VII)

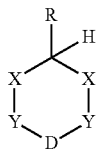

(VII)

wherein

X means O or S;

D means S, O, $PR^2$, or $NR^2$ with $R^2$ meaning straight chain or branched $C_1$-$C_{14}$ alkyl, preferably straight chain or branched $C_1$-$C_6$ alkyl, $C_3$-$C_8$ cycloalkyl, preferably $C_5$-$C_6$ cycloalkyl, $C_6$-$C_{24}$ aryl, preferably phenyl;

Y means a divalent moiety, preferably unsubstituted or substituted $C_2$-$C_6$ alkylene, preferably 1,2-ethylene, 1,3-propylene, or 1,4-butylene, or a unsubstituted or substituted $C_6$-$C_{10}$ arylene group, preferably 1,2-phenylene or 2,3-napthylene;

R means unsubstituted or substituted $C_6$-$C_{14}$, preferably $C_6$-$C_{10}$ aryl, more preferably phenyl with none, 1, 2, 3, 4, or 5 substituents selected from the group consisting of F, Cl, Br, and I;

either with a M-based complex containing at least one $L^1$ ligand, preferably a complex of general formula (VIII)

$M(L^1)_3(H)_2$            (VIII)

wherein

M is Ru, Os or Fe; and $L^1$ means a ligand, preferably $P(R^2)_3$ wherein $R^2$ means substituted or unsubstituted, straight chain or branched $C_1$-$C_{14}$ alkyl, substituted or unsubstituted $C_6$-$C_{24}$ aryl, or substituted or unsubstituted $C_3$-$C_{20}$ cycloalkyl or an N-heterocyclic carbene ligand;

or with a $M^0$ complex, preferably a $M^0$ complex of general formula (IX)

$M(L^3)_t$            (IX)

wherein t is 2, 3, 4, 5, or 6 and $L^3$ are identical or different and represent coordinated, straight chain or cyclic olefins and arenes, preferably cyclooctadiene and cyclooctatriene and a ligand $L^1$ having the same meanings as given for general formula (VIII).

Optionally a further ligand $L^1$ being different from $L^1$ in the M-based complex, preferably the complex of formula (VIII), can be added and thereby introduced into the compound of general formula (II).

Route A for preparing the transition metal complexes according to general formula (II) is an unprecedented route which is shown in total in the following scheme:

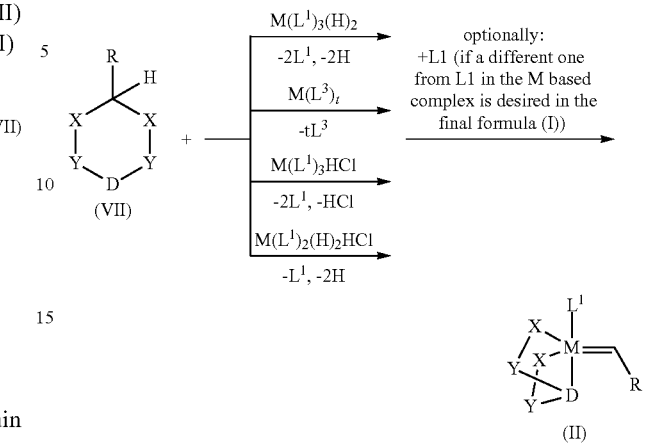

wherein D, Y, X, R, $L^1$ have the meanings outlined above with regard to general formula (II).

As $M^0$ source of the general formula $M(L^1)_3(H)_2$ or $M(L^3)_t$ compounds like $Ru(PPh_3)_3(H)_2$, $Ru(cod)(cot)$, and $Ru(H_2)_2(H)_2(PCy_3)_2$ can be used.

Alternatively, $Ru(PPh_3)_3HCl$ or $Ru(PCy_3)_2(H_2)HCl$ can be used as a M-based complex containing at least one $L^1$ ligand.

The compounds of general formula (VII) are accessible via methods sufficiently disclosed in the prior art or known to the person skilled in the art as e.g. J. Chem. Soc., Perkin Trans. 1, 1004, 707-715 with regard to thioacetals.

Reaction Conditions for complexes with general formula (II) via Route A:

The synthesis of the complexes of general formula (II) via Route A is typically carried out in an organic solvent, preferably in benzene, and at temperatures in the range of 20 to 80° C. Reaction times may typically be chosen in the range of from 2 to 24 hours. The reactions are typically carried out under oxygen and water free conditions. If a different $L^1$ is desired, it can be added any time during the reaction.

Route B:

Route B represents an alternative process for preparing the transition metal complexes according to general formula (II) comprising reacting a compound of general formula (IX)

wherein

M, R, $L^1$ shall have the same meanings as outlined for general formula (II) and $X^2$ are identical or different and represent an anionic ligand, preferably halide, more preferably F, Cl, Br or I, most preferably Cl;

with a compound of general formula (XI)

$D[(Y{-}X)^-K^+]_2$            (XI)

wherein

D, X, Y shall have the same meanings as outlined for general formula (II) and $K^+$ shall mean any mono charged cation or any equivalent thereof, preferably an alkali metal cation, more preferably $Li^+$, $Na^+$ or $K^+$, or an earth alkali metal cation, more preferably $\frac{1}{2}Ca^{2+}$ or $\frac{1}{2}Mg^{2+}$.

This Route B for preparing novel transition metal complexes according to general formula (II) is shown in total in the following scheme:

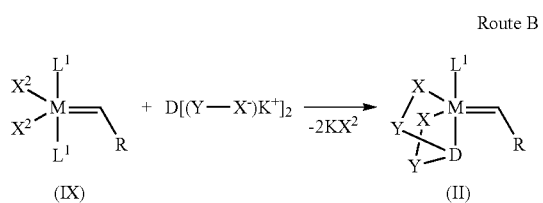

Furtheron the present invention relates to the use of the complexes according to general formula (I) as catalysts, preferably for converting C=C double bond containing substrates in metathesis reactions, more preferably ring-closing metatheses (RCM), cross-metatheses (CM) or a ring-opening metatheses (ROMP), or for hydrogenating C=C double bond containing substrates.

Additionally the invention relates to the use of the complexes according to general formula (IV) as catalysts, preferably for converting C=C double bond containing substrates in metathesis reactions, more preferably ring-closing metatheses (RCM), cross-metatheses (CM) or a ring-opening metatheses (ROMP), or for hydrogenating C=C double bond containing substrates.

In particular the present invention relates to a process for preparing compounds by subjecting a starting compound to a metathesis reaction or a hydrogenation reaction in the presence of a complex according to general formula (I) or (IV).

In a further particular embodiment the present invention relates to a process for preparing partially or fully hydrogenated nitrile rubbers by hydrogenating a starting nitrile rubber in the presence of a complex having general formula (I) or general formula (IV).

Hydrogenation:

Substrates to be Hydrogenated:

The process of the present invention is broadly applicable to the hydrogenation of a variety of substrates, including terminal olefins, internal olefins, cyclic olefins, conjugated olefins, and any further olefins having at least one carbon-carbon double bond and additionally at least one further polar unsaturated double or triple bond. The process is also applicable to the hydrogenation of polymers having carbon-carbon double bonds. Such polymers may represent homo-, co- or terpolymers.

As a terminal olefin or alkene, it is possible to hydrogenate a hydrocarbon compound with a terminal unsaturated carbon-carbon double bond having the general formula $C_nH_{2n}$. The terminal olefin can be a straight-chain or a branched hydrocarbon compound of any length, preferably 1-hexene.

As an internal olefin or alkene, it is possible to hydrogenate a hydrocarbon compound with an internal unsaturated carbon-carbon double bond having the general formula $C_nH_{2n}$. The internal olefin can be a straight-chain or a branched hydrocarbon of any length, preferably 2-hexene.

As a cyclic olefin or cycloalkene, it is possible to hydrogenate a hydrocarbon compound with a cyclic unsaturated carbon-carbon double bond having the general formula $C_nH_{2n-2}$. The cyclic olefin can be a ring of any size, preferably cyclohexene.

As a conjugated olefin or dialkene, it is possible to hydrogenate a hydrocarbon compound with conjugated carbon-carbon unsaturated double bonds. The conjugation can be a straight-chain or a branched hydrocarbon of any length, preferably styrene.

As an olefin, it is also possible to selectively hydrogenate a hydrocarbon compound with at least one unsaturated carbon-carbon double bond and least one other unsaturated polar double or triple bond. Such unsaturated polar bonds are surprisingly left unaltered. The carbon-carbon double bond in such olefins can be of any nature including terminal, internal, cyclic and conjugated ones. The additional unsaturated polar bond can be of any nature with preference given to carbon-nitrogen, carbon-phosphorus, carbon-oxygen, and carbon-sulfur unsaturated polar bonds.

Polymers having carbon-carbon double bonds may also be subjected to the inventive process. Such polymers preferably comprise repeating units based on at least one conjugated diene monomer.

The conjugated diene can be of any nature. In one embodiment $(C_4-C_6)$ conjugated dienes are used. Preference is given to 1,3-butadiene, isoprene, 1-methylbutadiene, 2,3-dimethylbutadiene, piperylene, chloroprene, or mixtures thereof. More preference is given to 1,3-butadiene, isoprene or mixtures thereof. Particular preference is given to 1,3-butadiene.

In a further embodiment polymers having carbon-carbon double bonds may be subjected to the inventive process which comprise repeating units of not only at least one conjugated diene as monomer (a) but additionally at least one further copolymerizable monomer (b). Examples of suitable monomers (b) are olefins, such as ethylene or propylene.

Further examples of suitable monomers (b) are vinylaromatic monomers, such as styrene, alpha-methyl styrene, o-chlorostyrene or vinyltoluenes, vinylesters of aliphatic or branched $C_1$-$C_{18}$ monocarboxylic acids, such as vinyl acetate, vinyl propionate, vinyl butyrate, vinyl valerate, vinyl hexanoate, vinyl 2-ethylhexanoate, vinyl decanoate, vinyl laurate and vinyl stearate.

A preferred polymer to be used in the present invention is a copolymer of 1,3-butadiene and styrene or alpha-methylstyrene. Said copolymers may have a random or block type structure.

Further examples of suitable monomers (b) are esters of ethylenically unsaturated monocarboxylic acids or mono- or diesters of dicarboxylic acids with generally $C_1$-$C_{12}$ alkanols, e.g. esters of acrylic acid, methacrylic acid, maleic acid, fumaric acid and itaconic acid with e.g. methanol, ethanol, n-propanol, isopropanol, 1-butanol, 2-butanol, isobutanol, tert-butanol, n-hexanol, 2-ethylhexanol, or $C_5$-$C_{10}$-cycloalkanols, such as cyclopentanol or cyclohexanol, and of these preferably the esters of acrylic and/or methacrylic acid, examples being methyl methacrylate, n-butyl methacrylate, tert-butyl methacrylate, n-butyl acrylate, tert-butyl acrylate, and 2-ethylhexyl acrylate.

The inventive process may be further used to hydrogenate so-called nitrile rubbers. Nitrile rubbers ("NBR") represent copolymers or terpolymers containing repeating units of at least one conjugated diene, at least one α,β-unsaturated nitrile monomer and, if appropriate, one or more further copolymerizable monomers.

The conjugated diene in such nitrile rubbers can be of any nature. Preference is given to using $(C_4-C_6)$-conjugated dienes. Particular preference is given to 1,3-butadiene, isoprene, 2,3-dimethylbutadiene, piperylene or mixtures thereof. In particular, use is preferably made of 1,3-butadiene or isoprene or mixtures thereof. Very particular preference is given to 1,3-butadiene.

As α,β-unsaturated nitrile monomer, it is possible to use any known α,β-unsaturated nitrile, with preference being given to ($C_3$-$C_5$)-α,β-unsaturated nitriles such as acrylonitrile, methacrylonitrile, ethacrylonitrile or mixtures thereof. Particularly preference is given to acrylonitrile.

A particularly preferred nitrile rubber to be subjected to hydrogenation according to the invention is thus a copolymer of acrylonitrile and 1,3-butadiene.

In addition to the conjugated diene and the α,β-unsaturated nitrile, it is possible to use one or more further copolymerizable monomers known to those skilled in the art, e.g. termonomers containing carboxyl groups, like α,β-unsaturated monocarboxylic acids, their esters or amides, α,β-unsaturated dicarboxylic acids, their monoesters or diesters, or their corresponding anhydrides or amides.

As α,β-unsaturated monocarboxylic acids it is possible to use acrylic acid and methacrylic acid.

It is also possible to employ esters of the α,β-unsaturated monocarboxylic acids, preferably their alkyl esters and alkoxyalkyl esters. Preference is given to the alkyl esters, especially $C_1$-$C_{18}$ alkyl esters, of the α,β-unsaturated monocarboxylic acids, Particular preference is given to alkyl esters, especially $C_1$-$C_{18}$ alkyl esters, of acrylic acid or of methacrylic acid, more particularly methyl acrylate, ethyl acrylate, propyl acrylate, n-butyl acrylate, tert-butyl acrylate, 2-ethylhexyl acrylate, n-dodecyl acrylate, methyl methacrylate, ethyl methacrylates, butyl methacrylate and 2-ethylhexyl methacrylate. Also preferred are alkoxyalkyl esters of the α,β-unsaturated monocarboxylic acids, more preferably alkoxyalkyl esters of acrylic acid or of methacrylic acid, more particular $C_2$-$C_{12}$ alkoxyalkyl esters of acrylic acid or of methacrylic acid, very preferably methoxymethyl acrylate, methoxyethyl(meth)acrylate, ethoxyethyl(meth)acrylate and methoxyethyl(meth)acrylate. Use may also be made of mixtures of alkyl esters, such as those mentioned above, for example, with alkoxyalkyl esters, in the form of those mentioned above, for example. Use may also be made of cyanoalkyl acrylate and cyanoalkyl methacrylates in which the C atom number of the cyanoalkyl group is 2-12, preferably α-cyanoethyl acrylate, β-cyanoethyl acrylate and cyanobutyl methacrylate. Use may also be made of hydroxyalkyl acrylates and hydroxyalkyl methacrylate in which the C atom number of the hydroxyalkyl groups is 1-12, preferably 2-hydroxyethyl acrylate, 2-hydroxyethyl methacrylate and 3-hydroxypropyl acrylate; use may also be made of fluorine-substituted benzyl-group-containing acrylates or methacrylates, preferably fluorobenzyl acrylate, and fluorobenzyl methacrylate. Use may also be made of acrylates and methacrylates containing fluoroalkyl groups, preferably trifluoroethyl acrylate and tetrafluoropropyl methacrylate. Use may also be made of α,β-unsaturated carboxylic esters containing amino groups, such as dimethylaminomethyl acrylate and diethylaminoethyl acrylate.

As copolymerizable monomers it is possible, furthermore, to use α,β-unsaturated dicarboxylic acids, preferably maleic acid, fumaric acid, crotonic acid, itaconic acid, citraconic acid and mesaconic acid. Use may be made, furthermore, of α,β-unsaturated dicarboxylic anhydrides, preferably maleic anhydride, itaconic anhydride, citraconic anhydride and mesaconic anhydride.

It is possible, furthermore, to use monoesters or diesters of α,β-unsaturated dicarboxylic acids.

These α,β-unsaturated dicarboxylic monoesters or diesters may be, for example, alkyl esters, preferably $C_1$-$C_{10}$ alkyl, more particularly ethyl, n-propyl, isopropyl, n-butyl, tert-butyl, n-pentyl or n-hexyl esters, alkoxyalkyl esters, preferably $C_2$-$C_{12}$ alkoxyalkyl, more preferably $C_3$-$C_8$-alkoxyalkyl, hydroxyalkyl, preferably $C_1$-$C_{12}$ hydroxyalkyl, more preferably $C_2$-$C_8$ hydroxyalkyl, cycloalkyl esters, preferably $C_5$-$C_{12}$ cycloalkyl, more preferably $C_6$-$C_{12}$ cycloalkyl, alkylcycloalkyl esters, preferably $C_6$-$C_{12}$ alkylcycloalkyl, more preferably $C_7$-$C_{10}$ alkylcycloalkyl, aryl esters, preferably $C_6$-$C_{14}$ aryl esters, these esters being monoesters or diesters, and it also being possible, in the case of the diesters, for the esters to be mixed esters.

Particularly preferred alkyl esters of α,β-unsaturated monocarboxylic acids are methyl(meth)acrylate, ethyl(meth)acrylate, propyl(meth)acrylate, n-butyl(meth)acrylate, t-butyl(meth)acrylate, hexyl(meth)acrylate, 2-ethylhexyl(meth)acrylate, octyl(meth)acrylate, 2-propylheptyl acrylate and lauryl(meth)acrylate. More particularly, n-butyl acrylate is used.

Particularly preferred alkoxyalkyl esters of the α,β-unsaturated monocarboxylic acids are methoxyethyl(meth)acrylate, ethoxyethyl(meth)acrylate and methoxyethyl(meth)acrylate. More particularly, methoxyethyl acrylate is used.

Particularly preferred hydroxyalkyl esters of the α,β-unsaturated monocarboxylic acids are hydroxyethyl(meth)acrylate, hydroxypropyl(meth)acrylate and hydroxybutyl(meth)acrylate.

Other esters of the α,β-unsaturated monocarboxylic acids that are used are additionally, for example, polyethylene glycol(meth)acrylate, polypropylene glycol(meth)acrylate, glycidyl(meth)acrylate, epoxy(meth)acrylate, N-(2-hydroxyethyl)acrylamides, N-(2-hydroxymethyl)acrylamides and urethane(meth)acrylate.

Examples of α,β-unsaturated dicarboxylic monoesters encompass maleic acid monoalkyl esters, preferably monomethyl maleate, monoethyl maleate, monopropyl maleate and mono-n-butyl maleate;

maleic acid monocycloalkyl esters, preferably monocyclopentyl maleate, monocyclohexyl maleate and monocycloheptyl maleate;

maleic acid monoalkyl cycloalkyl esters, preferably monomethyl cyclopentyl maleate and monoethyl cyclohexyl maleate;

maleic acid monoaryl esters, preferably monophenyl maleate;

maleic acid monobenzyl esters, preferably monobenzyl maleate;

fumaric acid monoalkyl esters, preferably monomethyl fumarate, monoethyl fumarate, monopropyl fumarate and mono-n-butyl fumarate;

fumaric acid monocycloalkyl esters, preferably monocyclopentyl fumarate, monocyclohexyl fumarate and monocycloheptyl fumarate;

fumaric acid monoalkyl cycloalkyl esters, preferably monomethyl cyclopentyl fumarate and monoethyl cyclohexyl fumarate;

fumaric acid monoaryl esters, preferably monophenyl fumarate;

fumaric acid monobenzyl esters, preferably monobenzyl fumarate;

citraconic acid monoalkyl esters, preferably monomethyl citraconate, monoethyl citraconate, monopropyl citraconate and mono-n-butyl citraconate;

citraconic acid monocycloalkyl esters, preferably monocyclopentyl citraconate, monocyclohexyl citraconate and monocycloheptyl citraconate;

citraconic acid monoalkyl cycloalkyl esters, preferably monomethyl cyclopentyl citraconate and monoethyl cyclohexyl citraconate;

citraconic acid monoaryl esters, preferably monophenyl citraconate;

citraconic acid monobenzyl esters, preferably monobenzyl citraconate;

itaconic acid monoalkyl esters, preferably monomethyl itaconate, monoethyl itaconate, monopropyl itaconate and mono-n-butyl itaconate;

itaconic acid monocycloalkyl esters, preferably monocyclopentyl itaconate, monocyclohexyl itaconate and monocycloheptyl itaconate;

itaconic acid monoalkyl cycloalkyl esters, preferably monomethyl cyclopentyl itaconate and monoethyl cyclohexyl itaconate;

itaconic acid monoaryl esters, preferably monophenyl itaconate;

itaconic acid monobenzyl esters, preferably monobenzyl itaconate.

Mesaconic acid monoalkyl esters, preferably mesaconic acid monoethyl esters;

As $\alpha,\beta$-unsaturated dicarboxylic diesters it is possible to use the analogous diesters based on the abovementioned monoester groups, and the ester groups may also be chemically different groups.

Preferably the substrate to be hydrogenated is a nitrile rubber comprising repeating units of at least one conjugated diene, at least one $\alpha,\beta$-unsaturated nitrile and, if appropriate, one or more further copolymerizable monomers, preferably a nitrile rubber comprising repeating units of at least one conjugated diene selected from the group consisting of 1,3-butadiene, isoprene, 2,3-dimethylbutadiene, piperylene and mixtures thereof, at least one $\alpha,\beta$-unsaturated nitrile selected from the group consisting of acrylonitrile, methacrylonitrile, ethacrylonitrile and mixtures thereof, and optionally of one or more further copolymerizable monomers selected from the group consisting of $\alpha,\beta$-unsaturated monocarboxylic, dicarboxylic acids, their esters or amides.

The proportions of conjugated diene and $\alpha,\beta$-unsaturated nitrile monomer in the NBR polymers to be used can vary within wide ranges. The proportion of the conjugated diene or the sum of conjugated dienes is usually in the range from 40 to 90% by weight, preferably in the range from 50 to 85% by weight, based on the total polymer. The proportion of the $\alpha,\beta$-unsaturated nitrile or the sum of the $\alpha,\beta$-unsaturated nitriles is usually from 10 to 60% by weight, preferably from 15 to 50% by weight, based on the total polymer. The proportions of the monomers in each case add up to 100% by weight. The additional monomers can be present in amounts of from 0 to 40% by weight, preferably from 0.1 to 40% by weight, particularly preferably from 1 to 30% by weight, based on the total polymer. In this case, corresponding proportions of the conjugated diene or dienes and/or the $\alpha,\beta$-unsaturated nitrile or nitriles are replaced by the proportions of the additional monomers, with the proportions of all monomers in each case adding up to 100% by weight.

The preparation of such nitrile rubbers by polymerization of the abovementioned monomers is adequately known to those skilled in the art and is comprehensively described in the literature.

Nitrile rubbers which can be used for the purposes of the invention are commercially available, e.g. as products marketed under the trademarks Perbunan® and Krynac® by Lanxess Deutschland GmbH. The nitrile rubbers which can be used for the hydrogenation have a Mooney viscosity (ML 1+4 at 100° C.) in the range from 30 to 70, preferably from 30 to 50. This corresponds to a weight average molecular weight $M_w$ in the range 150,000-500,000, preferably in the range 180,000-400,000. The nitrile rubbers used typically have a polydispersity $PDI=M_w/M_n$ ($M_n$ is the number average molecular weight and $M_n$ is the number average molecular weight) in the range of 2.0-6.0 and preferably in the range 2.0-4.0.

Hydrogenated nitrile rubbers obtained pursuant to this invention can have a Mooney viscosity (ML 1+4 at 100° C.) in the range of greater than 0 up to 150, typically the Mooney viscosity lies in the range of from 5 to 150, preferably of from 10 to 120, more preferably of from 30 to 110, even more preferably of from 35 to 100, and particularly preferably of from 50 to 100 and most preferably of from 60 to 90. The determination of the Mooney viscosity is carried out in accordance with ASTM standard D 1646.

They typically have a polydispersity $PDI=M_w/M_n$ in the range of 1.5 to 6 and preferably in the range of 1.8 to 4.

Hydrogenation Conditions:

The hydrogenation is generally carried out at a temperature in the range from 0° C. to 200° C., preferably in the range from 15° C. to 150° C. This means that the process may be carried out at mild conditions. In case low molecular weight olefins like terminal olefins, internal olefins, cyclic olefins, conjugated olefins, or any other olefins having at least one carbon-carbon double bond and additionally at least one further polar unsaturated double bond are subjected to hydrogenation, the temperature typically lies in the range from 20 to 100° C. In case polymers with double bonds in the polymer backbone are used as substrates the hydrogenation temperature typically lies in a range from 40 to 200° C., preferably in the range from 70 to 150° C.

The hydrogenation process of the present invention is preferably carried out with hydrogen gas at a pressure from 0.1 to 20 MPa, preferably at a pressure from 1 to 16 MPa. In one embodiment of the present process said hydrogen gas is essentially pure.

Preferably the hydrogenation process is carried out at a temperature in the range from 0° C. to 200° C. with hydrogen gas at a pressure from 0.1 to 20 MPa, preferably at a temperature in the range from 15° C. to 150° C. with hydrogen gas at a pressure from 1 to 16 MPa.

The amount of catalyst according to general formula (I) can vary in a broad range. Typically the catalyst according to general formula (I) is used in a molar ratio from (0.01-0.20):1, preferably from (0.01-0.05):1 based on the substrate to be hydrogenated.

In the hydrogenation of rubber polymers the amount of catalyst according to formula (I) may also vary in a broad range. The amount of catalyst is then calculated on a weight base ratio in "phr" (parts per hundred rubber). Typically 0.005 phr to 2.5 phr catalyst are used based on the rubber. Preferably 0.01 phr to 2 phr and more preferably 0.025 phr to 2 phr catalyst are used based on the rubber.

The hydrogenation can be carried out in a suitable solvent which does not deactivate the catalyst used and also does not adversely affect the reaction in any other way. Preferred solvents include but are not restricted to methanol, chlorobenzene, bromobenzene, dichloromethane, benzene, toluene, methyl ethyl ketone, acetone, tetrahydrofuran, tetrahydropyran, dioxane and cyclohexane. The particularly preferred solvent is chlorobenzene. In some cases, when the substrate to be hydrogenated itself can function as solvent, e.g. in the case of 1-hexene, the addition of a further additional solvent can also be omitted.

According to the present invention the complex catalyst can be introduced into the polymer by any possible means, such as e.g. mechanical mixing, preferably by using a procedure which can result in a homogeneous distribution of the catalyst and polymer.

In one embodiment of the present invention the catalyst according to formula (I) is contacted with the substrate to be hydrogenated by adding the catalyst or catalyst solution to a substrate solution and mixing until an efficient distribution and dissolution of the catalyst has taken place.

The present process can be performed in the presence or absence of any further co-catalyst or other additives. It is not necessary to add such further co-catalyst or other additives. This applies in particular to co-catalysts which are typically used e.g. in combination with other hydrogenation catalysts known from prior art like the Wilkinson's catalyst. In one embodiment of the present invention the process is conducted in the presence or absence of co-catalysts having the formula $R^1{}_mZ$, wherein $R^1$ are identical or different and are each a $C_1$-$C_8$-alkyl group, a $C_4$-$C_8$-cycloalkyl group, a $C_6$-$C_{15}$-aryl group or a $C_7$-$C_{15}$-aralkyl group, Z is phosphorus, arsenic, sulphur or a sulphoxide group S=O, preferably phosphorus, and m is 2 or 3, preferably 3. In a further embodiment the present process is conducted in the presence or absence of triphenylphosphine.

The hydrogenation process of the present invention can be undertaken in a suitable reactor equipped with temperature regulating and agitating means. It is possible to perform the process either batch-wise or continuously.

During the course of the hydrogenation reaction of the present invention, the hydrogen is added to the reactor. The reaction time is typically from about one quarter of an hour to about 100 hours, depending on operational conditions. As the novel catalysts are robust, it is not necessary to use a special gas dryer to dry the hydrogen.

According to the present invention, when the hydrogenation reaction is complete, to the extent desired, the reaction vessel can be cooled (if applicable) and vented and the hydrogenated substrate can be isolated by conventional methods well known to any artisan.

Metathesis:

The present invention further provides a process of contacting at least one substrate containing C=C double bonds with a novel complex catalyst according to general formula (I) and performing a metathesis reaction. The metathesis reaction can be, for example, a ring-closing metatheses (RCM), a cross-metatheses (CM) or a ring-opening metatheses (ROMP). For this purpose, the substrate or substrates to be subjected to the metathesis is/are brought into contact and reacted with the complex catalyst according to formula (I).

In particular the present invention relates to a process for preparing a nitrile rubber with a weight average molecular weight $M_w'$ by subjecting a starting nitrile rubber having a weight average molecular weight $M_w$ to a cross-metathesis reaction in the presence complex according to general formula (I), wherein the weight average molecular weight of the starting nitrile rubber $M_w$ is higher than the weight average molecular weight $M_w$ of the nitrile rubber prepared.

In particular the present invention relates to a process for preparing a nitrile rubber with a weight average molecular weight $M_w'$ by subjecting a starting nitrile rubber having a weight average molecular weight $M_w$ to a cross-metathesis reaction in the presence complex according to general formula (IV), wherein the weight average molecular weight of the starting nitrile rubber $M_w$ is higher than the weight average molecular weight $M_w$ of the nitrile rubber prepared.

Compounds to be Subjected to Metathesis:

Any type of compounds containing at least one C=C double bond can be subjected to a metathesis reaction.

The inventive process can be preferably applied to nitrile rubbers for which the definition given above with regard to the hydrogenation reaction shall apply.

The complex catalyst according to general formula (I) is preferably used for the metathesis of nitrile rubber. The use according to the invention is then a process for reducing the molecular weight of nitrile rubber by bringing the nitrile rubber into contact with the catalyst system according to the invention. This reaction is a cross metathesis.

The amount of complex catalyst according to general formula (I) based on the nitrile rubber used depends on the nature and the catalytic activity of the specific complex catalyst. The amount of complex catalyst used is usually from 1 to 1000 ppm of noble metal, preferably from 2 to 500 ppm, in particular from 5 to 250 ppm, based on the nitrile rubber used.

The NBR metathesis can be carried out in the absence or in the presence of a coolefin. This is preferably a straight-chain or branched $C_2$-$C_{16}$-olefin. Suitable olefins are, for example, ethylene, propylene, isobutene, styrene, 1-hexene and 1-octene. Preference is given to using 1-hexene or 1-octene. If the coolefin is liquid (for example as in the case of 1-hexene), the amount of coolefin is preferably in the range 0.2-20% by weight based on the NBR used. If the coolefin is a gas, for example as in the case of ethylene, the amount of coolefin is preferably selected so that a pressure in the range $1\times10^5$ Pa-$1\times10^7$ Pa, preferably a pressure in the range from $5.2\times10^5$ Pa to $4\times10^6$ Pa, is established in the reaction vessel at room temperature.

The metathesis reaction can be carried out in a suitable solvent which does not deactivate the catalyst used and also does not adversely affect the reaction in any other way. Preferred solvents encompass, but are not restricted to, dichloromethane, benzene, toluene, methyl ethyl ketone, acetone, tetrahydrofuran, tetrahydropyran, dioxane, cyclohexane and chlorobenzene. The particularly preferred solvent is chlorobenzene. In some case, when the coolefin itself can act as solvent, e.g. in the case of 1-hexene, the addition of a further additional solvent can also be dispensed with.

The concentration of the nitrile rubber used in the reaction mixture of the metathesis is not critical, but it naturally has to be noted that the reaction should not be adversely affected by an excessively high viscosity of the reaction mixture and the mixing problems associated therewith. The concentration of the NBR in the reaction mixture is preferably in the range from 1 to 25% by weight, particularly preferably in the range from 5 to 20% by weight, based on the total reaction mixture.

The metathetic degradation is usually carried out at a temperature in the range from 10° C. to 150° C., preferably at a temperature in the range from 20 to 100° C.

The reaction time depends on a number of factors, for example on the type of NBR, on the type of catalyst, on the catalyst concentration employed and on the reaction temperature. The reaction is typically complete within five hours under normal conditions. The progress of the metathesis can be monitored by standard analytical methods, e.g. by GPC measurements or by determination of the viscosity.

EXAMPLES

Abbreviations used:

"Grubbs I catalyst" and "Grubbs II catalyst" shall mean

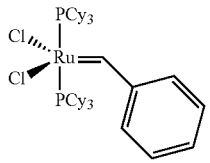
Grubbs I

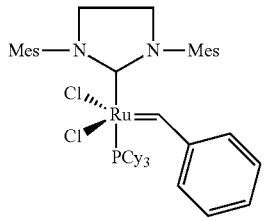
Grubbs II

All solvents have been purchased from Caledon Laboratory Chemicals.

I Synthesis of Compounds 1-26 in Accordance with Route B

I.1 Synthesis of Ru(PCy₃)(=CHPh)[O(CH₂CH₂S)₂] (1)

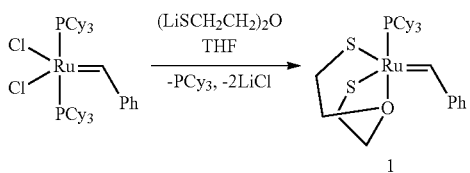

A THF solution (5 mL) of (LiSCH₂CH₂)₂O.2THF (0.020 g, 0.137 mmol) was added to a THF solution (5 mL) of Grubbs I catalyst (0.100 g, 0.126 mmol) and stirred overnight. All volatiles were removed from the dark brown solution. The dark brown solid was taken up in CH₂Cl₂ (5 mL) and filtered through a celite packed pipette. Upon concentration to dryness, the resulting dark brown solid was washed with hexane (2×20 mL) and dried to yield a dark red solid (0.075 g, 98%).

$^1$H NMR (CD$_2$Cl$_2$): 13.68 (d, $^3J_{PH}$=11.8 Hz, 1H, Ru=CH), 7.27 (m, 2H, Ph), 7.14 (m, 3H, Ph), 3.84 (m, 2H, CH$_2$), 3.21 (m, 2H, CH$_2$), 2.74 (m, 4H, 2×CH$_2$), 2.11, 1.98, 1.74, 1.61, 1.50, 1.19 (all m, P(C$_6$H$_{11}$)$_3$.

$^{13}$C{$^1$H} NMR (CD$_2$Cl$_2$): 207.95 (Ru=CH), 153.25 (ipso-C, Ph), 128.15 (2×CH, Ph), 125.58 (CH, Ph), 125.39 (2×CH, Ph), 77.96 (2×CH$_2$), 35.91 (d, $^1J_{PC}$=24.17 Hz, ipso-C of P(C$_6$H$_{11}$)$_3$), 32.42 (2×CH$_2$), 29.97 (m-C of P(C$_6$H$_{11}$)$_3$), 28.31 (d, $^2J_{PC}$=10.25 Hz, o-C of P(C$_6$H$_{11}$)$_3$), 26.93 (p-C of P(C$_6$H$_{11}$)$_3$).

$^{31}$P{$^1$H} NMR (CD$_2$Cl$_2$): 65.60.

I.2 Synthesis of Ru(Mes₂Im)(=CHPh)[O(CH₂CH₂S)₂] (2)

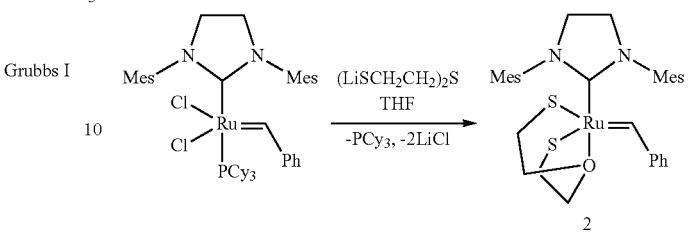

Grubbs II catalyst (0.326 g, 0.384 mmol) in CH₃CN (5 mL) was added to (LiSCH₂CH₂)₂O.2THF (0.144 g, 0.489 mmol) in MeCN (5 mL) and toluene (10 mL) and stirred for 16 h. All volatiles were removed from the dark brown solution. CH₂Cl₂ (5 mL) was added to give a dark brown solution which was filtered through celite. Upon concentration to dryness, the resulting dark brown solid was washed with hexane (2×20 mL) and dried to yield a black-red solid. X-Ray quality crystals were grown from a CH₂Cl₂/CH₃CN solution. (0.243 g, 99%).

$^1$H NMR (CD$_2$Cl$_2$): 14.85 (s, 1H, Ru=CH), 7.14 (t, 1H, p-H, Ph), 6.97-7.05 (m, 4H, Ph), 6.86 (s, 4H, 4×CH, Mes), 3.92 (s, 4H, 2×CH$_2$, Im), 3.65 (m, 2H, CH$_2$), 2.82 (m, 2H, CH$_2$), 2.45 (s, 12H, 4×CH$_3$, Mes), 2.32-2.41 (m, 4H, 2×CH$_2$), 2.23 (s, 6H, 2×CH$_3$, Mes).

$^{13}$C{$^1$H} NMR (CD$_2$Cl$_2$): 209.98 (Ru=CH), 153.68 (ipso-C, Ph), 137.89 (ipso-C, NCN), 137.38 (ipso-C, Mes), 137.31 (ipso-C, Mes), 127.27 (2×CH, Ph), 128.81 (4×CH, Mes), 125.02 (2×CH, Ph), 124.65 (CH, p-C, Ph), 77.56 (2×CH$_2$), 51.84 (2×CH$_2$, Im), 31.59 (2×CH$_2$), 20.59 (2×CH$_3$, Mes), 19.12 (4×CH$_3$, Mes).

I.3 Synthesis of Ru(PCy₃)(=CHPh)Cl[O(CH₂CH₂S)₂BCl₂] (3)

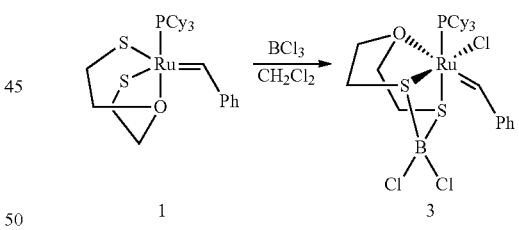

To a CH₂Cl₂ solution (1 mL) of 1 (0.020 g, 0.033 mmol) was added BCl₃ in hexanes (1 M, 33 µL, 0.033 mmol). The red solution immediately turned green. All volatiles were removed, and the resulting dark solid was washed with CH₃CN (2 mL) and dried to yield a green solid. (0.021 g, 89%). X-Ray quality crystals were grown from a CH₂Cl₂/CH₃CN solution.

$^1$H NMR (CD$_2$Cl$_2$): 18.93 (d, $^3J_{PH}$=11.7 Hz, 1H, Ru=CH), 8.87 (d, $^3J_{HH}$=8.27 Hz, 2H, o-H of C$_6$H$_5$), 7.74 (t, $^3J_{HH}$=7.98 Hz, 1H, p-H of C$_6$H$_5$), 7.51 (t, $^3J_{HH}$=8.17 Hz, 2H, m-H of C$_6$H$_5$), 5.05, 4.56, 4.19, 3.82, 3.13, 3.00, 2.89, 2.78 (all m, 1H, CH$_2$), 2.12, 1.88, 1.82-1.64, 1.52, and 1.21-1.13 (all m, P(C$_6$H$_{11}$)$_3$). $^{11}$B NMR (CD$_2$Cl$_2$): 11.08 (s).

$^{13}$C{$^1$H} NMR (CD$_2$Cl$_2$): 277.37 (Ru=CH), 153.05 (ipso-C, Ph), 132.67 (2×CH, Ph), 131.81 (CH, Ph), 128.36 (2×CH, Ph), 71.15, 68.58 (2×CH$_2$), 36.20 (d, $^1J_{PC}$=19.21

Hz, ipso-C of P(C$_6$H$_{11}$)$_3$), 33.24, 30.57 (2×CH$_2$), 29.54 (m-C of P(C$_6$H$_{11}$)$_3$), 27.93 (o-C of P(C$_6$H$_{11}$)$_3$), 26.43 (p-C of P(C$_6$H$_{11}$)$_3$).
$^{31}$P{$^1$H} NMR (CD$_2$Cl$_2$): 35.54.

I.4 Synthesis of Ru(Mes$_2$Im)(=CHPh)Cl[O(CH$_2$CH$_2$S)$_2$BCl$_2$] (4)

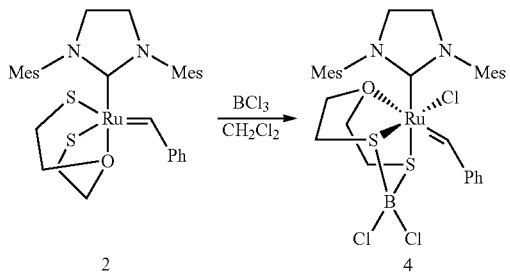

To a CH$_2$Cl$_2$ solution (1 mL) of 2 (0.020 g, 0.032 mmol) was added BCl$_3$ in hexanes (1 M, 32 μL, 0.032 mmol). The brown solution immediately turned dark green. All volatiles were removed, and the resulting dark solid was washed with CH$_3$CN (2 mL) and dried to yield a blue-green solid. (0.022 g, 92%). X-Ray quality crystals were grown from a CH$_2$Cl$_2$/CH$_3$CN solution.

$^1$H NMR (CD$_2$Cl$_2$): 17.68 (s, 1H, Ru=CH), 8.09 (br, 2H, o-H of C$_6$H$_5$) 7.56 (t, $^3J_{HH}$=7.54 Hz, 1H, p-H, Ph), 7.24 (t, $^3J_{HH}$=7.54 Hz, 2H, m-H of C$_6$H$_5$), 7.03 (s, 2H, 2×CH, Mes), 6.56 (s, 2H, 2×CH, Mes), 4.84 (m, 1H, CH$_2$), 3.84 (m, 2H, CH$_2$, Im), 3.74 (m, 1H, CH$_2$), 3.64 (m, 2H, CH$_2$, Im), 3.01, 2.80, 2.62 (all m, 1H, CH$_2$), 2.52 (s, 6H, 2×CH$_3$, Mes), 2.34 (m, 2H, CH$_2$), 2.25 (s, 6H, 2×CH$_3$, Mes), 2.20 (s, 6H, 2×CH$_3$, Mes), 2.17 (m, 1H, CH$_2$). $^{13}$C{$^1$H} NMR (CD$_2$Cl$_2$): 308.91 (Ru=CH), 214.62 (ipso-C, Ph), 152.04 (ipso-C, NCN), 138.54 (CMe, Mes), 137.59 (ipso-C, Mes), 137.39 (ipso-C, Mes), 132.65 (2×o-CH, Ph), 130.65 (p-CH, Ph), 129.64, 129.25 (4×CH, Mes), 126.96 (2×m-CH, Ph), 70.30, 68.12 (2×CH$_2$), 52.16, 53.83 (2×CH$_2$, Im), 30.56, 26.53 (2×CH$_2$), 20.70 (2×CH$_3$, Mes), 19.05 (2×CH$_3$, Mes), 18.73 (2×CH$_3$, Mes).
$^{11}$B NMR (CD$_2$Cl$_2$): 11.46.

I.5 Synthesis of [Ru(PCy$_3$)(=CHPh)[O(CH$_2$CH$_2$S)$_2$BCl$_2$]CH$_3$CN]BCl$_4$ (5)

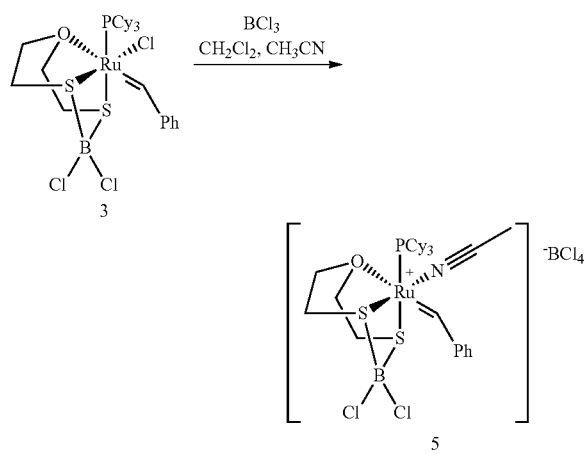

To a CH$_2$Cl$_2$ solution (1 mL) of 3 (0.050 g, 0.069 mmol) was added BCl$_3$ in hexanes (1 M, 69 μL, 0.069 mmol). The green solution immediately turned darker green. To this, CH$_3$CN (0.300 mL) was added and the solution turned dark red. All volatiles were removed and the dark red solid was dissolved in CH$_2$Cl$_2$ (1 mL) and filtered. Pentane (5 mL) was added and a dark red precipitate formed. The solid was collected, washed with pentane (2×2 mL) and dried in vacuo to yield a dark red solid. (0.053 g, 87%). X-Ray quality crystals were grown from a CH$_2$Cl$_2$ solution layered with pentane.

$^{11}$B NMR (CD$_2$Cl$_2$): 11.76 (BS$_2$Cl$_2$), 7.00 (BCl$_4$).
$^{31}$P{$^1$H} NMR (CD$_2$Cl$_2$): 36.14.

I.6 Synthesis of [Ru(Mes$_2$Im)(=CHPh)[O(CH$_2$CH$_2$S)$_2$BCl$_2$]CH$_3$CN]BCl$_4$ (6)

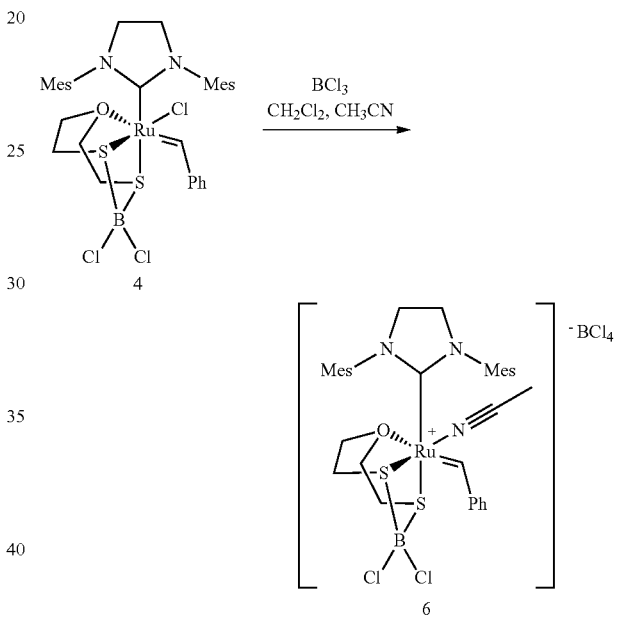

To a CH$_2$Cl$_2$ solution (1 mL) of 4 (0.030 g, 0.040 mmol) was added BCl$_3$ in hexanes (1 M, 40 μL, 0.040 mmol). The green-blue solution immediately turned darker green. To this, CH$_3$CN (0.100 mL) was added and the solution turned red. All volatiles were removed and the red solid was dissolved in CH$_2$Cl$_2$ (1 mL) and filtered. Pentane (5 mL) was added and a red precipitate formed. The solid was collected, washed with pentane (2×2 mL) and dried in vacuo to yield a red solid. (0.034 g, 94%). X-Ray quality crystals were grown from a CH$_2$Cl$_2$ solution layered with pentane.

$^1$H NMR (CD$_2$Cl$_2$): 17.26 (s, 1H, Ru=CH), 7.64 (m, 3H, o-H and p-H of C$_6$H$_5$) 7.38 (t, $^3J_{HH}$=7.99 Hz, 2H, m-H of C$_6$H$_5$), 7.00 (s, 2H, 2×CH, Mes), 6.77 (s, 2H, 2×CH, Mes), 4.02 (m, 1H, CH$_2$), 3.83 (br, 5H, 1H, CH$_2$ and 2×CH$_2$, Im), 3.46 (m, 2H, CH$_2$, Im), 3.21 (m, 1H, CH$_2$), 2.66 (m, 3H, 3×CH, CH$_2$), 2.53 (s, 6H, 2×CH$_3$, Mes), 2.47 (s, 3H, CH$_3$CN) 2.27 (s, 6H, 2×CH$_3$, Mes), 2.25 (s, 6H, 2×CH$_3$, Mes).
$^{13}$C{$^1$H} NMR (CD$_2$Cl$_2$): 208.50 (ipso-C, Ph), 151.65 (ipso-C, NCN), 140.05 (CMe, Mes), 137.53 (ipso-C, Mes), 136.85 (Mes), 136.43 (Mes), 134.08 (2×o-CH, Ph), 131.79 (p-CH, Ph) 130.33, 129.92 (4×CH, Mes), 129.06 (2×m-CH, Ph), 70.35, 69.45 (2×CH$_2$), 54.10, 53.14 (2×CH$_2$, Im), 34.52, 33.92 (2×CH$_2$), 22.76 (2×CH$_3$, Mes), 19.03 (2×CH$_3$, Mes), 18.79 (2×CH$_3$, Mes), 14.20 (CH$_3$, CH$_3$CN).
$^{11}$B NMR (CD$_2$Cl$_2$): 11.39 (BS$_2$Cl$_2$), 6.92 (BCl$_4$).

I.6.a Synthesis of [Ru(Mes$_2$Im)(=CHPh)[O(CH$_2$CH$_2$S)$_2$BCl$_2$]CH$_3$CN]Q(R$^3$)m (6.a)

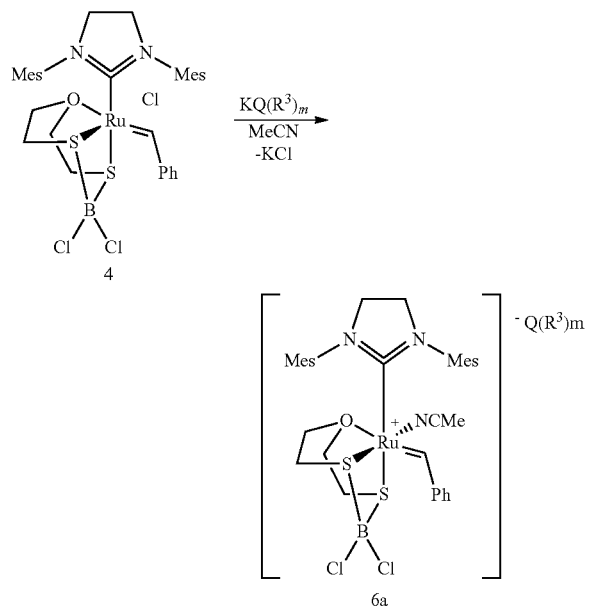

To a CH$_2$Cl$_2$ solution (3 mL) of 4 (0.300 g, 0.400 mmol) was added GQ(R$^3$)$_m$ (0.410 mmol) as defined below in CH$_2$Cl$_2$ (3 ml). To this excess CH$_3$CN was added and the reaction was stirred overnight. The next morning the green-blue solution turned to a dark red/purple color. The solution was filtered through Celite to remove any KCl salts and then all volatiles were removed in vacuo. Pentane (5 mL) was added to the residue and titrated to produce a red precipitate. The solid was collected, washed with pentane (2×2 mL) and dried in vacuo to yield a red solid.

GQ(R$^3$)$_m$=K[B(C$_6$F$_5$)$_4$]
$^1$H NMR (CD$_2$Cl$_2$): 17.26 (s, 1H, Ru=CH), 7.64 (m, 3H, o-H and p-H of C$_6$H$_5$) 7.38 (t, $^3$J$_{HH}$=7.99 Hz, 2H, m-H of C$_6$H$_5$), 7.00 (s, 2H, 2×CH, Mes), 6.77 (s, 2H, 2×CH, Mes), 4.02 (m, 1H, CH$_2$), 3.83 (br, 5H, 1H, CH$_2$ and 2×CH$_2$, Im), 3.46 (m, 2H, CH$_2$, Im), 3.21 (m, 1H, CH$_2$), 2.66 (m, 3H, 3×CH, CH$_2$), 2.53 (s, 6H, 2×CH$_3$, Mes), 2.47 (s, 3H, CH$_3$CN) 2.27 (s, 6H, 2×CH$_3$, Mes), 2.25 (s, 6H, 2×CH$_3$, Mes).
$^{11}$B NMR (CD$_2$Cl$_2$): 11.39 (BS$_2$Cl$_2$), −11.67 (B(C$_6$F$_5$)$_4$).
GQ(R$^3$)$_m$=K[BPh$_4$]
$^1$H NMR (CD$_2$Cl$_2$): 17.26 (s, 1H, Ru=CH), 7.64 (m, 3H, o-H and p-H of C$_6$H$_5$) 7.38 (t, $^3$J$_{HH}$=7.99 Hz, 2H, m-H of C$_6$H$_5$), 7.24 (m, 8H, BPh$_4$) 7.00 (s, 10H, 2×CH, Mes and BPh$_4$), 6.77 (s, 6H, 2×CH, Mes and BPh$_4$), 4.02 (m, 1H, CH$_2$), 3.83 (br, 5H, 1H, CH$_2$ and 2×CH$_2$, Im), 3.46 (m, 2H, CH$_2$, Im), 3.21 (m, 1H, CH$_2$), 2.66 (m, 3H, 3×CH, CH$_2$), 2.53 (s, 6H, 2×CH$_3$, Mes), 2.47 (s, 3H, CH$_3$CN) 2.27 (s, 6H, 2×CH$_3$, Mes), 2.25 (s, 6H, 2×CH$_3$, Mes).
$^{11}$B NMR (CD$_2$Cl$_2$): 11.39 (BS$_2$Cl$_2$), −6.57 (BPh$_4$).
GQ(R$^3$)$_m$=K[PF$_6$]
$^1$H NMR (CD$_2$Cl$_2$): 17.26 (s, 1H, Ru=CH), 7.64 (m, 3H, o-H and p-H of C$_6$H$_5$) 7.38 (t, $^3$J$_{HH}$=7.99 Hz, 2H, m-H of C$_6$H$_5$), 7.00 (s, 2H, 2×CH, Mes), 6.77 (s, 2H, 2×CH, Mes), 4.02 (m, 1H, CH$_2$), 3.83 (br, 5H, 1H, CH$_2$ and 2×CH$_2$, Im), 3.46 (m, 2H, CH$_2$, Im), 3.21 (m, 1H, CH$_2$), 2.66 (m, 3H, 3×CH, CH$_2$), 2.53 (s, 6H, 2×CH$_3$, Mes), 2.47 (s, 3H, CH$_3$CN) 2.27 (s, 6H, 2×CH$_3$, Mes), 2.25 (s, 6H, 2×CH$_3$, Mes).
$^{11}$B NMR (CD$_2$Cl$_2$): 11.39 (BS$_2$Cl$_2$)
$^{31}$P NMR (CD$_2$Cl$_2$): −144.48 (hept, $^1$J$_{PF}$=711 Hz, PF$_6$).
$^{19}$F NMR (CD$_2$Cl$_2$): −73.01 (hept, $^1$J$_{PF}$=711 Hz, PF$_6$).

I.7 Synthesis of Ru(PCy$_3$)(=CHPh)[S(CH$_2$CH$_2$S)$_2$] (7)

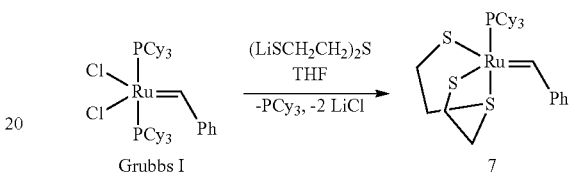

A THF solution (5 mL) of (LiSCH$_2$CH$_2$)$_2$S.2THF (0.020 g, 0.123 mmol) was added to a THF solution (5 mL) of Grubbs 1 (0.092 g, 0.112 mmol) and stirred overnight. All volatiles were removed from the dark brown solution. The dark brown solid was taken up in CH$_2$Cl$_2$ (5 mL) and filtered through a celite packed pipette. Upon concentration to dryness, the resulting dark brown solid was washed with hexane (2×20 mL) and dried to yield a dark red solid (0.068 g, 97%). X-ray quality crystals were grown from a CH$_2$Cl$_2$/CH$_3$CN solution.
$^1$H NMR (CD$_2$Cl$_2$): 13.48 (d, $^3$J$_{PH}$=19.3 Hz, 1H, Ru=CH), 7.12 (m, 3H, Ph), 6.93 (m, 2H, Ph), 3.41 (m, 2H, CH$_2$), 3.24 (m, 2H, CH$_2$), 2.45 (m, 2H, CH$_2$), 1.93 (m, 2H, CH$_2$), 2.28, 2.04, 1.73, 1.57, 1.19 (all m, P(C$_6$H$_{11}$)$_3$.
$^{13}$C{$^1$H} NMR (CD$_2$Cl$_2$): 235.16 (d, $^2$J$_{PC}$=14.78 Hz, Ru=CH), 157.02 (ipso-C, Ph), 127.51 (2×CH, Ph), 125.84 (2×CH, Ph), 125.40 (CH, Ph), 45.17 (2×CH$_2$), 36.28 (2×CH$_2$), 35.19 (d, $^1$J$_{PC}$=19.78 Hz, ipso-C of P(C$_6$H$_{11}$)$_3$), 29.98 (m-C of P(C$_6$H$_{11}$)$_3$), 28.37 (d, $^2$J$_{PC}$=10.25 Hz, o-C of P(C$_6$H$_{11}$)$_3$), 26.93 (p-C of P(C$_6$H$_{11}$)$_3$).
$^{31}$P{$^1$H} NMR (CD$_2$Cl$_2$): 41.71.

I.8 Synthesis of Ru(Mes$_2$Im)(=CHPh)[S(CH$_2$CH$_2$S)$_2$] (8)

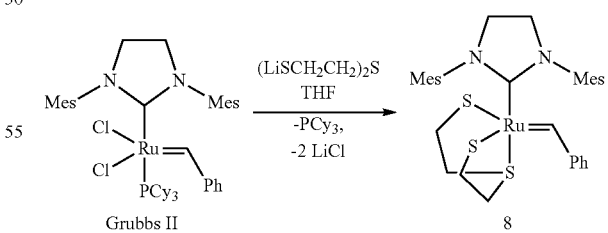

A THF solution (5 mL) of (LiSCH$_2$CH$_2$)$_2$S 2THF (0.020 g, 0.123 mmol) was added to a THF solution (5 mL) of Grubbs 2 (0.095 g, 0.112 mmol) and stirred overnight. All volatiles were removed from the dark brown solution. The dark brown solid was taken up in CH$_2$Cl$_2$ (5 mL) and filtered through a celite packed pipette. Upon concentration to dryness, the resulting dark brown solid was washed with hexane (2×20 mL) and dried to yield a dark red solid (0.071 g, 98%). X-ray quality crystals were grown from a CH$_2$Cl$_2$/CH$_3$CN solution.

$^1$H NMR (CD$_2$Cl$_2$): 14.41 (s, 1H, Ru=CH), 7.19 (t, 1H, p-H, Ph), 7.07 (t, 2H, m-H, Ph), 6.88 (d, 2H, o-H, Ph), 6.80 (s, 4H, 4×CH, Mes), 3.99 (s, 4H, 2×CH$_2$, Im), 3.22 (m, 2H, CH$_2$), 3.00 (m, 2H, CH$_2$), 2.52 (s, 12H, 4×CH$_3$, Mes), 2.24 (m, 2H, CH$_2$), 2.19 (s, 6H, 2×CH$_3$, Mes), 1.73 (m, 2H, CH$_2$).

$^{13}$C{$^1$H} NMR (CD$_2$Cl$_2$): 211.18 (Ru=CH), 138.08 (ipso-C, Ph), 137.79 (ipso-C, NCN), 137.73 (ipso-C, Mes), 129.18 (4×CH, Mes), 127.25.18 (2×CH, Ph), 127.11 (2×CH, Ph), 125.14 (CH, p-C, Ph), 52.43 (2×CH$_2$), 44.56 (2×CH$_2$, Im), 34.77 (2×CH$_2$), 20.98 (2×CH$_3$, Mes), 19.68 (4×CH$_3$, Mes).

I.9 Synthesis of Ru(PCy$_3$)(=CHPh)Cl[S(CH$_2$CH$_2$S)$_2$BCl$_2$] (9)

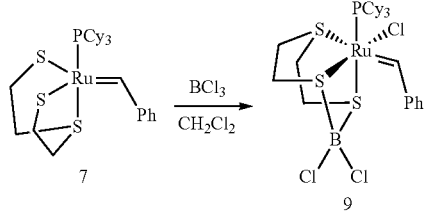

To a CH$_2$Cl$_2$ solution (1 mL) of Ru(PCy$_3$)(=CHPh)[S(CH$_2$CH$_2$S)$_2$] (7) (0.020 g, 0.032 mmol) was added BCl$_3$ in hexanes (1 M, 32 µL, 0.032 mmol). The red solution immediately turned green. All volatiles were removed, and the resulting dark solid was washed with CH$_3$CN (2 mL) and dried to yield a green solid. (0.022 g, 93%).

$^1$H NMR (CD$_2$Cl$_2$): 17.96 (d, $^3J_{PH}$=15.1 Hz, 1H, Ru=CH), 8.34 (d, $^3J_{HH}$=8.81 Hz, 2H, o-H of C$_6$H$_5$), 7.65 (t, $^3J_{HH}$=7.73 Hz, 1H, p-H of C$_6$H$_5$), 7.40 (t, $^3J_{HH}$=7.83 Hz, 2H, m-H of C$_6$H$_5$), 3.66, 3.13, 2.95 (all m, 1H, CH$_2$), 2.55 (m, 5H, 5×CH$_2$), 2.05, 1.88, 1.75-1.45, and 1.18 (all m, P(C$_6$H$_{11}$)$_3$).

$^{11}$B NMR (CD$_2$Cl$_2$): 9.94 (s).

$^{13}$C{$^1$H} NMR (CD$_2$Cl$_2$): 275.25 (Ru=CH), 154.83 (ipso-C, Ph), 132.15 (CH, Ph), 131.84 (2×CH, Ph), 128.77 (2×CH, Ph), 39.32, 38.98 (2×CH$_2$), 36.73 (d, $^1J_{PC}$=19.32 Hz, ipso-C of P(C$_6$H$_{11}$)$_3$), 30.24, 30.03 (2×CH$_2$), 27.79 (m-C of P(C$_6$H$_{11}$)$_3$), 27.55 (o-C of P(C$_6$H$_{11}$)$_3$), 26.56 (p-C of P(C$_6$H$_{11}$)$_3$). $^{31}$P{$^1$H} NMR (CD$_2$Cl$_2$): 34.92.

I.10 Synthesis of Ru(Mes$_2$Im)(=CHPh)Cl[S(CH$_2$CH$_2$S)$_2$BCl$_2$] (10)

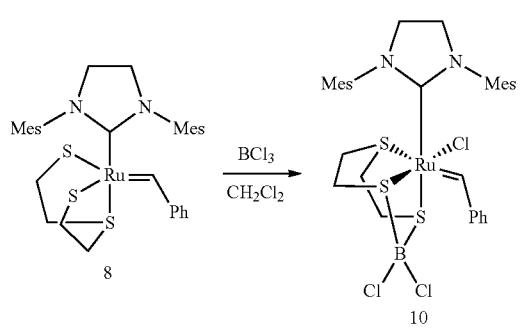

To a CH$_2$Cl$_2$ solution (1 mL) of Ru(Mes$_2$Im)(=CHPh)[S(CH$_2$CH$_2$S)$_2$] (8) (0.020 g, 0.031 mmol) was added BCl$_3$ in hexanes (1 M, 31 µL, 0.031 mmol). The brown solution immediately turned dark green. All volatiles were removed, and the resulting dark solid was washed with CH$_3$CN (2 mL) and dried to yield a blue-green solid. (0.022 g, 93%). X-Ray quality crystals were grown from a CH$_2$Cl$_2$/CH$_3$CN solution.

$^{11}$B NMR (CD$_2$Cl$_2$): 11.46.

I.11 Synthesis of Ru(PCy$_3$)(=CHPh)[PhP(CH$_2$CH$_2$S)$_2$] (11)

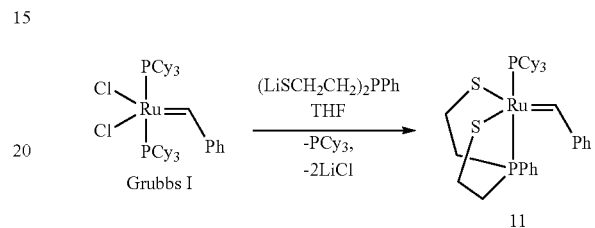

A THF solution (5 mL) of (LiSCH$_2$CH$_2$)$_2$PPh (0.032 g, 0.134 mmol) was added to a THF solution (5 mL) of Grubbs 1 (0.100 g, 0.122 mmol) and stirred overnight. All volatiles were removed from the dark brown solution. The dark brown solid was taken up in CH$_2$Cl$_2$ (5 mL) and filtered through a celite packed pipette. Upon concentration to dryness, the resulting dark brown solid was washed with hexane (2×20 mL) and dried to yield a dark red solid (0.076 g, 89%).

$^1$H NMR (CD$_2$Cl$_2$): 13.31 (dd, $^3J_{PH}$=23.2 Hz, $^3J_{PH}$=1.8 Hz, 1H, Ru=CH), 7.04 (m, 5H, PPh), 6.94 (d, 2H, Ph), 6.71 (m, 3H, Ph), 3.07 (m, 2H, CH$_2$), 2.93 (m, 2H, CH$_2$), 2.47 (m, 5H, CH$_2$, P(C$_6$H$_{11}$)$_3$), 2.15 (m, 2H, CH$_2$), 2.20, 1.86, 1.72, 1.33 (all m, P(C$_6$H$_{11}$)$_3$.

$^{13}$C{$^1$H} NMR (CD$_2$Cl$_2$): 235.90 (appt, $^2J_{PC}$=12.57 Hz, Ru=CH), 155.7 (dd, $^3J_{PC}$=10.50 Hz, 3.85 Hz, ipso-C, Ph), 130.74 (d, $^2J_{PC}$=9.27 Hz, 2×CH, PPh), 128.56 (CH, PPh), 128.55 (d, $^1J_{PC}$=267.1 Hz, CH, PPh), 127.65 (d, $^3J_{PC}$=9.25 Hz, 2×CH, PPh), 127.09 (2×CH, Ph), 126.03 (2×CH, Ph), 124.99 (CH, Ph), 34.16 (m, 2×CH$_2$), 31.49 (m, 2×CH$_2$), 29.53 (m-C of P(C$_6$H$_{11}$)$_3$), 28.04 (d, $^1J_{PC}$=9.02 Hz, ipso-C of P(C$_6$H$_{11}$)$_3$), 27.70 (d, $^2J_{PC}$=9.02 Hz, o-C of P(C$_6$H$_{11}$)$_3$), 26.56 (p-C of P(C$_6$H$_{11}$)$_3$).

$^{31}$P{$^1$H} NMR (CD$_2$Cl$_2$): 114.7 (d, $^2J_{PP}$=330.6 Hz), 28.9 (d, $^2J_{PP}$=331.8 Hz).

I.12 Synthesis of Ru(PCy$_3$)(=CHPh)Cl[PhP(CH$_2$CH$_2$S)$_2$BCl$_2$] (12)

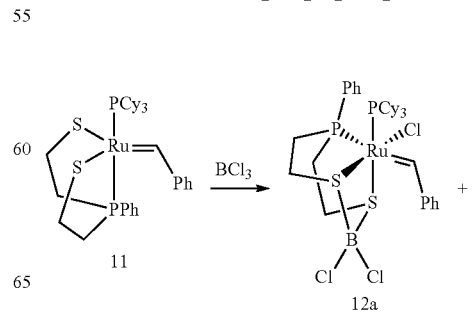

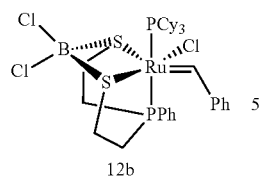

To a CH$_2$Cl$_2$ solution (1 mL) of Ru(PCy$_3$)(=CHPh)[PhP(CH$_2$CH$_2$S)$_2$] (11) (0.020 g, 0.029 mmol) was added BCl$_3$ in hexanes (1 M, 29 µL, 0.029 mmol). The brown solution immediately turned dark green.

All volatiles were removed, and the resulting dark solid was washed with CH$_3$CN (2 mL) and dried to yield a dark green solid. (0.022 g, 93%). The compound exists as a mixture of isomers (12a, 12b). With the addition of one more equivalent of BCl$_3$ the compound becomes an active olefin metathesis catalyst.

$^1$H NMR (CD$_2$Cl$_2$): 18.06 (d, $^3J_{PH}$=6.78 Hz, Ru=CH, 12b), 17.32 (dd, $^3J_{PH}$=17.4 Hz, $^3J_{PH}$=10.6 Hz, Ru=CH, 12a), all other peaks correspond to isomeric mixture.

$^{11}$B NMR (CD$_2$Cl$_2$): 10.67.

$^{31}$P{$^1$H} NMR (CD$_2$Cl$_2$): 81.54 (d, $^2J_{PP}$=255.2 Hz, PPh, 12b), 75.76 (d, $^2J_{PP}$=25.8 Hz, PPh, 12a), 29.64 (d, $^2J_{PP}$=25.9 Hz, PCy$_3$, 12a), 26.87 (d, $^2J_{PP}$=256.6 Hz, PCy$_3$, 12b).

I.13 Synthesis of Ru(PCy$_3$)(=CHPh)[O(C$_6$H$_4$S)$_2$] (13)

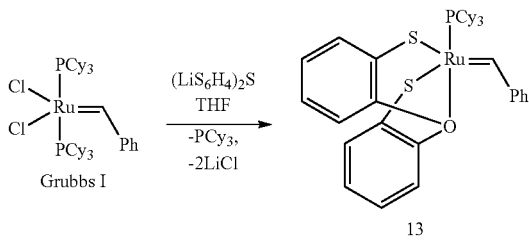

A THF solution (5 mL) of (LiSC$_6$H$_4$)$_2$O (0.033 g, 0.134 mmol) was added to a THF solution (5 mL) of Grubbs 1 (0.100 g, 0.122 mmol) and stirred overnight. All volatiles were removed from the dark brown solution. The dark brown solid was taken up in CH$_2$Cl$_2$ (5 mL) and filtered through a celite packed pipette. Upon concentration to dryness, the resulting dark brown solid was washed with hexane (2×20 mL) and dried to yield a red solid (0.068 g, 97%). X-ray quality crystals were grown from a CH$_2$Cl$_2$ solution.

$^1$H NMR (CD$_2$Cl$_2$): 14.69 (d, $^3J_{PH}$=14.7 Hz, 1H, Ru=CH) 7.48 (d, $^3J_{HH}$=7.6 Hz, 2H, Ph), 7.48 (m, 3H, Ph), 6.90 (m, 4H, Ph), 6.82 (t, $^3J_{HH}$=7.3 Hz, 2H, Ph), 6.72 (m, 2H, Ph), 2.15, 2.02, 1.77, 1.55, 1.19 (all m, P(C$_6$H$_{11}$)$_3$.

$^{13}$C{$^1$H} NMR (CD$_2$Cl$_2$): 192.20 (Ru=CH), 154.03 (2×ipso-C, Ph), 152.23 (ipso-C, Ph), 139.08 (2×ipso-C, Ph), 132.14 (2×CH, Ph), 130.14 (2×CH, Ph), 127.94 (2×CH, Ph), 126.31 (CH, Ph), 125.27 (2×CH, Ph), 123.97 (2×CH, Ph), 122.70 (2×CH, Ph), 115.86 (2×CH, Ph), 35.95 (d, $^1J_{PC}$=25.05 Hz, ipso-C of P(C$_6$H$_{11}$)$_3$), 31.62 (m-C of P(C$_6$H$_{11}$)$_3$), 30.09 (p-C of P(C$_6$H$_{11}$)$_3$), 28.19 (d, $^2J_{PC}$=10.24 Hz, o-C of P(C$_6$H$_{11}$)$_3$).

$^{31}$P{$^1$H} NMR (CD$_2$Cl$_2$): 68.60.

I.14 Synthesis of Ru(Mes$_2$Im)(=CHPh)[O(C$_6$H$_4$S)$_2$] (14)

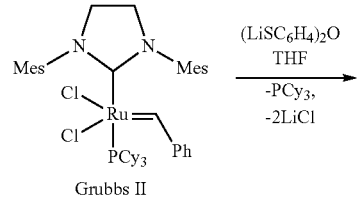

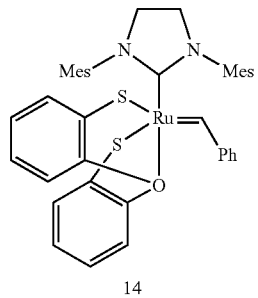

A THF solution (5 mL) of (LiSC$_6$H$_4$)$_2$O (0.038 g, 0.153 mmol) was added to a THF solution (5 mL) of Grubbs II (0.100 g, 0.118 mmol) and stirred overnight. All volatiles were removed from the dark brown solution. The dark brown solid was taken up in CH$_2$Cl$_2$ (5 mL) and filtered through a celite packed pipette. Upon concentration to dryness, the resulting dark brown solid was washed with hexane (2×20 mL) and dried to yield a red solid (0.074 g, 86%).

$^1$H NMR (CD$_2$Cl$_2$): 15.60 (s, 1H, Ru=CH), 7.41 (d, 2H, Ph), 6.91 (m, 8H, Ph, Mes), 6.79 (m, 5H, Ph), 6.64 (m, 2H, Ph), 4.08 (s, 4H, 2×CH$_2$, Im), 2.51 (s, 12H, 4×CH$_3$, Mes), 2.22 (s, 6H, 2×CH$_3$, Mes).

$^{13}$C{$^1$H} NMR (CD$_2$Cl$_2$): 209.13 (Ru=CH), 153.13 (ipso-C, Ph), 151.45 (ipso-C, Ph) 139.53 (ipso-C, NCN), 137.97 (ipso-C, Mes), 137.17 (ipso-C, Mes), 131.26 (2×CH, Ph), 129.18 (2×CH, Ph), 128.90 (2×CH, Ph), 128.14 (2×CH, Ph), 126.10 (4×CH, Mes), 127.42 (2×CH, Ph), 125.22 (CH, p-C, Ph), 122.90 (CH, Ph), 121.54 (2×CH, Ph), 114.78 (2×CH, Ph), 51.84 (2×CH$_2$, Im), 20.71 (2×CH$_3$, Mes), 18.99 (4×CH$_3$, Mes).

I.15 Synthesis of Ru(PCy$_3$)(=CHPh)Cl [O(C$_6$H$_4$S)$_2$BCl$_2$] (15)

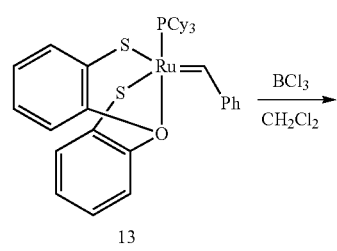

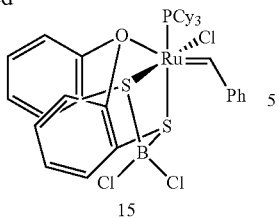

To a CH$_2$Cl$_2$ solution (1 mL) of Ru(PCy$_3$)(=CHPh)[O(C$_6$H$_4$S)$_2$] (13) (0.020 g, 0.028 mmol) was added BCl$_3$ in hexanes (1 M, 28 μL, 0.028 mmol). The red solution immediately turned green and a blue-green precipitate began to form. All volatiles were removed, and the resulting dark solid was washed with CH$_3$CN (2 mL) and dried to yield a blue-green solid. (0.020 g, 87%).

$^1$H NMR (CD$_2$Cl$_2$): 18.85 (d, $^3J_{PH}$=11.6 Hz, 1H, Ru=CH), 8.54 (d, $^3J_{HH}$=7.9 Hz, 2H, Ph), 7.74 (m, 3H, Ph), 7.57-7.37 (m, 6H, Ph), 7.20 (m, 2H, Ph), 2.40, 2.07, 1.80, 1.62, 1.43 (all m, P(C$_6$H$_{11}$)$_3$.

$^{31}$P{$^1$H} NMR (CD$_2$Cl$_2$): 36.51.

$^{11}$B NMR (CD$_2$Cl$_2$): 12.11.

I.16 Synthesis of Ru(SIMes)(=CHPh)Cl [O(C$_6$H$_4$S)$_2$BCl$_2$] (16)

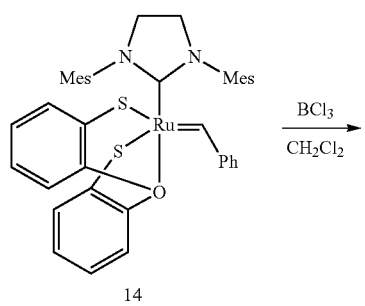

To a CH$_2$Cl$_2$ solution (1 mL) of Ru(SIMes)(=CHPh)[O(C$_6$H$_4$S)$_2$] (15) (0.020 g, 0.027 mmol) was added BCl$_3$ in hexanes (1 M, 27 μL, 0.027 mmol). The red solution immediately turned green and a blue-green precipitate began to form. All volatiles were removed, and the resulting dark solid was washed with CH$_3$CN (2 mL) and dried to yield a green solid. (0.019 g, 83%).

I.17 Synthesis of [Ru(PCy$_3$)(=CHPh)[O(C$_6$H$_4$S)$_2$BCl$_2$]CH$_3$CN]BCl$_4$ (17)

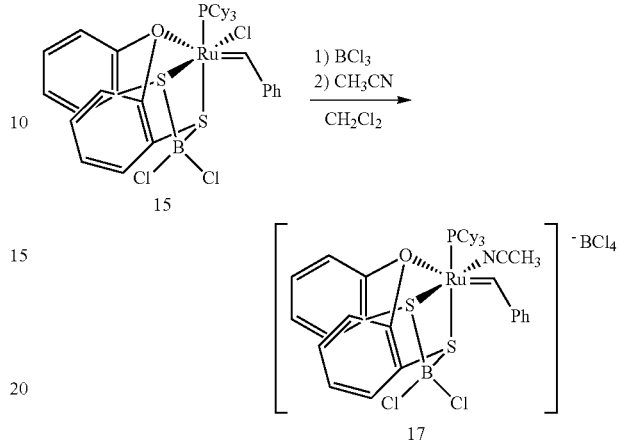

To a CH$_2$Cl$_2$ solution (1 mL) of 15 (0.020 g, 0.024 mmol) was added BCl$_3$ in hexanes (1 M, 24 μL, 0.024 mmol). The green-blue solution immediately turned darker green. To this, CH$_3$CN (0.100 mL) was added and the solution turned red. All volatiles were removed and the red solid was dissolved in CH$_2$Cl$_2$ (1 mL) and filtered. Pentane (5 mL) was added and a red precipitate formed. The solid was collected, washed with pentane (2×2 mL) and dried in vacuo to yield a red solid. (0.019 g, 81%).

I.18 Synthesis of [Ru(SIMes)(=CHPh)[O(C$_6$H$_4$S)$_2$BCl$_2$]CH$_3$CN]BCl$_4$ (18)

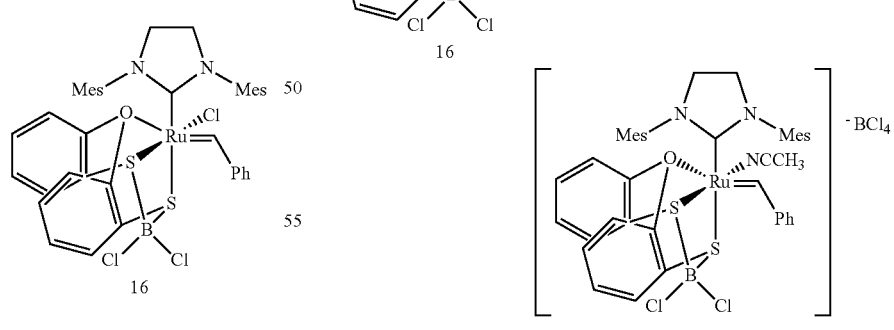

To a CH$_2$Cl$_2$ solution (1 mL) of 15 (0.020 g, 0.024 mmol) was added BCl$_3$ in hexanes (1 M, 24 μL, 0.024 mmol). The green-blue solution immediately turned darker green. To this, CH$_3$CN (0.100 mL) was added and the solution turned red. All volatiles were removed and the red solid was dissolved in CH$_2$Cl$_2$ (1 mL) and filtered. Pentane (5 mL) was added and a red precipitate formed. The solid was collected, washed with pentane (2×2 mL) and dried in vacuo to yield a red solid. (0.021 g, 88%).

I.19 Synthesis of Ru(PCy$_3$)(=CHPh)[O(CH$_2$CH$_2$O)$_2$] (19)

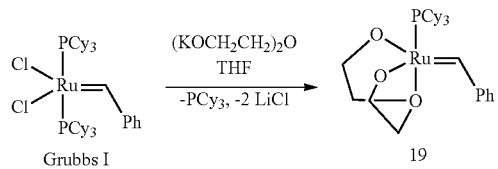

A THF solution (5 mL) of (KOCH$_2$CH$_2$)$_2$O (0.025 g, 0.137 mmol) was added to a THF solution (5 mL) of Grubbs 1 (0.100 g, 0.126 mmol) and stirred overnight. All volatiles were removed from the dark brown solution. The dark brown solid was taken up in toluene (5 mL) and filtered through a celite packed pipette. Upon concentration to dryness, the resulting red solid was washed with hexane (2×20 mL) and dried to yield a red solid (0.068 g, 90%).

$^1$H NMR (CD$_2$Cl$_2$): 15.72 (d, $^3J_{PH}$=14.8 Hz, 1H, Ru=CH), 7.91 (d, $^3J_{HH}$=8.02 Hz 2H, Ph), 7.31 (m, 3H, Ph), 4.19 (m, 2H, CH$_2$), 3.96 (m, 2H, CH$_2$), 3.39 (m, 2H, CH$_2$), 2.96 (m, 2H, CH$_2$), 2.44, 2.22, 1.87, 1.67, 1.65 (all m, P(C$_6$H$_{11}$)$_3$.
$^{31}$P{$^1$H} NMR (CD$_2$Cl$_2$): 64.76.

I.20 Synthesis of Ru(Mes$_2$Im)(=CHPh)[O(CH$_2$CH$_2$O)$_2$] (20)

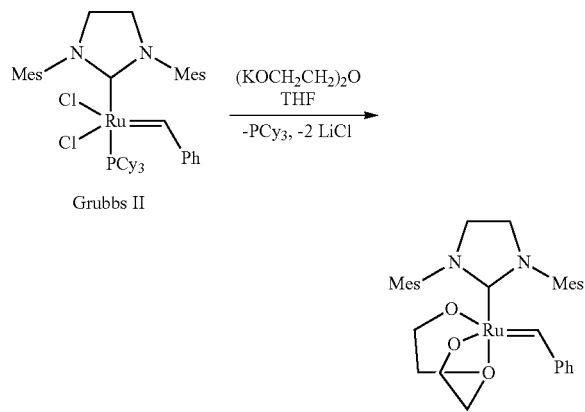

Grubbs 2 (0.100 g, 0.118 mmol) in THF (5 mL) was added to (KOCH$_2$CH$_2$)$_2$O (0.028 g, 0.153 mmol) in THF (10 mL) and stirred for 16 h. All volatiles were removed from the dark brown solution.

Toluene (5 mL) was added to give a dark brown solution which was filtered through celite. Upon concentration to dryness, the resulting dark brown solid was washed with hexane (2×20 mL) and dried to yield a dark red solid. (0.63 g, 90%).

$^1$H NMR (CD$_2$Cl$_2$): 16.23 (s, 1H, Ru=CH), 7.58 (d, 2H, Ph), 7.18 (m, 3H, Ph), 6.87 (s, 4H, 4×CH, Mes), 3.78 (m, 4H, 2×CH$_2$), 3.44 (s, 4H, 2×CH$_2$, Im), 3.18 (m, 4H, 2×CH$_2$), 2.57 (s, 12H, 4×CH$_3$, Mes), 2.19 (s, 6H, 2×CH$_3$, Mes).

I.21 Synthesis of Ru(PCy$_3$)(=CHPh)Cl[O(CH$_2$CH$_2$O)$_2$BCl$_2$] (21)

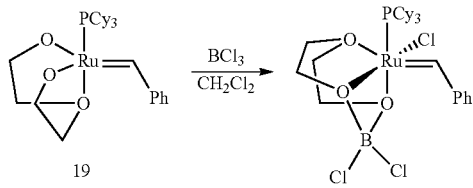

To a CH$_2$Cl$_2$ solution (1 mL) of 19 (0.020 g, 0.035 mmol) was added BCl$_3$ in hexanes (1 M, 35 μL, 0.035 mmol). The red solution immediately turned green. All volatiles were removed, and the resulting dark solid was washed with CH$_3$CN (2 mL) and dried to yield a green solid. (0.019 g, 85%).

I.22 Synthesis of Ru(PCy$_3$)(=CHPh)Cl[O(CH$_2$CH$_2$O)$_2$BCl$_2$] (22)

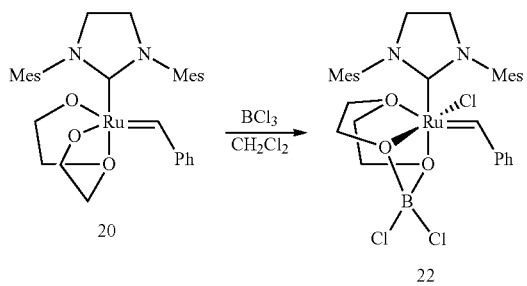

To a CH$_2$Cl$_2$ solution (1 mL) of 20 (0.020 g, 0.033 mmol) was added BCl$_3$ in hexanes (1 M, 33 μL, 0.033 mmol). The brown solution immediately turned dark green. All volatiles were removed, and the resulting dark solid was washed with CH$_3$CN (2 mL) and dried to yield a green solid. (0.022 g, 92%).

I.23 Synthesis of [Ru(PCy$_3$)(=CHPh)[O(CH$_2$CH$_2$O)$_2$BCl$_2$]CH$_3$CN]BCl$_4$ (23)

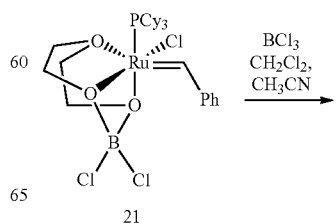

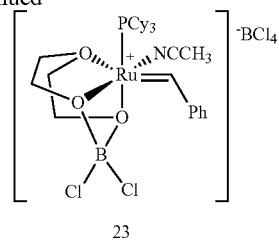

23

To a CH$_2$Cl$_2$ solution (1 mL) of 3 (0.020 g, 0.031 mmol) was added BCl$_3$ in hexanes (1 M, 31 μL, 0.031 mmol). The green solution immediately turned darker green. To this, CH$_3$CN (0.300 mL) was added and the solution turned dark red. All volatiles were removed and the dark red solid was dissolved in CH$_2$Cl$_2$ (1 mL) and filtered. Pentane (5 mL) was added and a dark red precipitate formed. The solid was collected, washed with pentane (2×2 mL) and dried in vacuo to yield a dark red solid. (0.022 g, 85%).

I.24 Synthesis of [Ru(Mes$_2$Im)(=CHPh)[O(CH$_2$CH$_2$O)$_2$BCl$_2$]CH$_3$CN]BCl$_4$ (24)

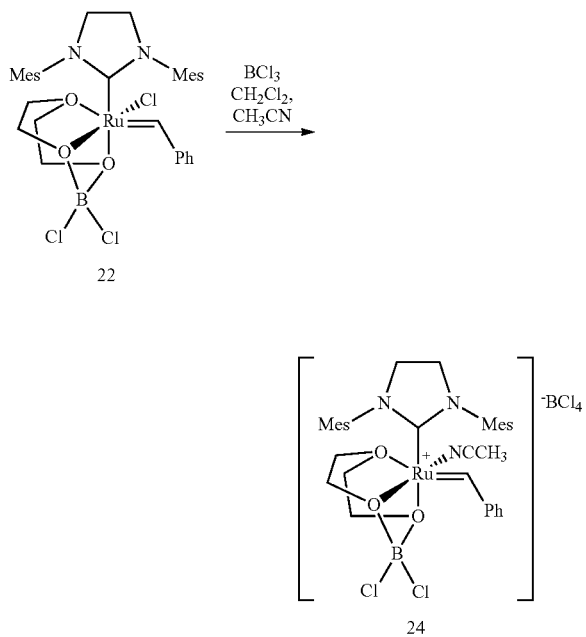

To a CH$_2$Cl$_2$ solution (1 mL) of 4 (0.030 g, 0.042 mmol) was added BCl$_3$ in hexanes (1 M, 42 μL, 0.042 mmol). The green-blue solution immediately turned darker green. To this, CH$_3$CN (0.100 mL) was added and the solution turned red. All volatiles were removed and the red solid was dissolved in CH$_2$Cl$_2$ (1 mL) and filtered. Pentane (5 mL) was added and a red precipitate formed. The solid was collected, washed with pentane (2×2 mL) and dried in vacuo to yield a red solid. (0.032 g, 84%).

I.25 Synthesis of Ru(PCy$_3$)(=CHPh)Cl[O(CH$_2$CH$_2$S)$_2$B(C$_6$F$_5$)$_2$] (25)

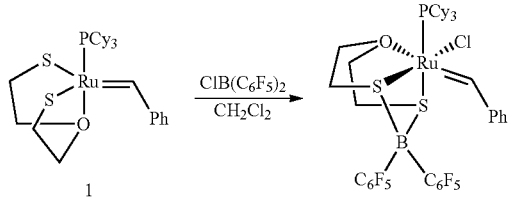

To a CH$_2$Cl$_2$ solution (0.5 mL) of 1 (0.020 g, 0.033 mmol) was added CH$_2$Cl$_2$ solution (0.5 mL) of ClB(C$_6$F$_5$)$_2$ (0.013 g, 0.033 mmol). The red solution immediately turned green. All volatiles were removed, and the resulting dark solid was washed with CH$_3$CN (2 mL) and dried to yield a green solid. (0.024 g, 75%).

$^1$H NMR (CD$_2$Cl$_2$): 18.47 (d, $^3J_{PH}$=13.9 Hz, 1H, Ru=CH), 8.18 (br, 2H, o-H of C$_6$H$_5$), 7.53 (t, $^3J_{HH}$=7.18 Hz, 1H, p-H of C$_6$H$_5$), 7.24 (t, $^3J_{HH}$=7.18 Hz, 2H, m-H of C$_6$H$_5$), 5.05, 4.78, (m, 2×1H, CH$_2$), 4.28 (m, 2H, CH$_2$), 2.93, 2.64, 2.52, 2.39 (all m, 1H, CH$_2$), 1.88, 1.65, 1.45-1.33, 1.14 (all m, P(C$_6$H$_{11}$)$_3$). $^{11}$B NMR (CD$_2$Cl$_2$): 5.20 (s). $^{19}$F NMR (CD$_2$Cl$_2$): −155.7, −157.1, −164.0.

I.26 Synthesis of Ru(PCy$_3$)(=CHPh)Cl[O(CH$_2$CH$_2$S)$_2$B(C$_6$F$_5$)$_2$] (26)

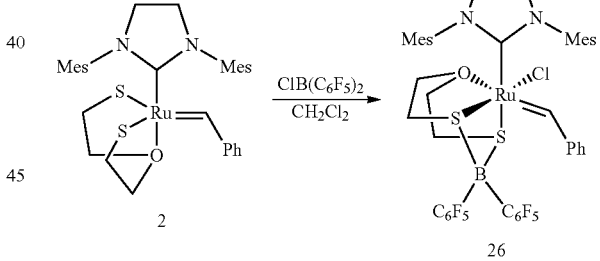

To a CH$_2$Cl$_2$ solution (1 mL) of 2 (0.020 g, 0.032 mmol) was added CH$_2$Cl$_2$ solution (0.5 mL) of ClB(C$_6$F$_5$)$_2$ (0.012 g, 0.032 mmol). The brown solution immediately turned dark green. All volatiles were removed, and the resulting dark solid was washed with CH$_3$CN (2 mL) and dried to yield a blue-green solid. (0.028 g, 87%).

$^1$H NMR (CD$_2$Cl$_2$): 17.75 (s, 1H, Ru=CH), 7.65 (br, 2H, o-H of C$_6$H$_5$) 7.43 (t, $^3J_{HH}$=7.31 Hz, 1H, p-H, Ph), 7.07 (t, $^3J_{HH}$=7.31 Hz, 2H, m-H of C$_6$H$_5$), 7.05 (s, 2H, 2×CH, Mes), 6.60 (s, 2H, 2×CH, Mes), 4.95 (m, 1H, CH$_2$), 3.81 (m, 4H, CH$_2$, Im, 2×CH$_2$), 3.64 (m, 2H, CH$_2$, Im), 2.79, 2.69, 2.62 (all m, 1H, CH$_2$), 2.56 (s, 6H, 2×CH$_3$, Mes), 2.49 (m, 1H, CH$_2$), 2.26 (s, 6H, 2×CH$_3$, Mes), 2.19 (s, 6H, 2×CH$_3$, Mes), 2.00 (m, 1H, CH$_2$).

$^{11}$B NMR (CD$_2$Cl$_2$): 8.86.

I.27 Synthesis of [Ru(Mes₂Im)(=CHPh)[O(CH₂CH₂S)₂BCl₂]]BCl₄ (4+BCl₃)

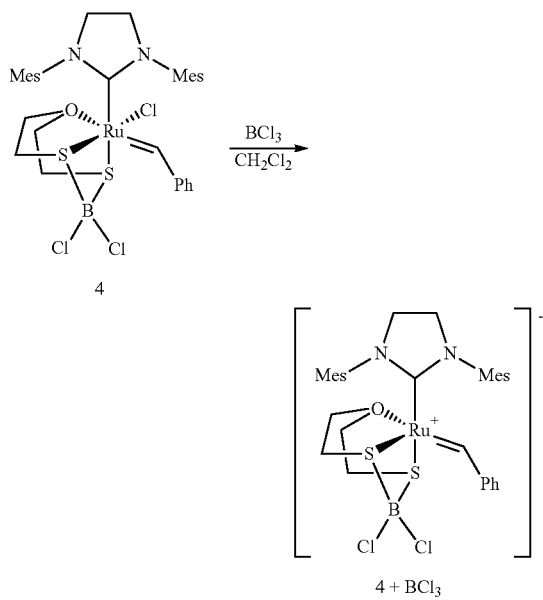

To a CH₂Cl₂ solution (1 mL) of 4 (0.030 g, 0.040 mmol) was added BCl₃ in hexanes (1 M, 40 μL, 0.040 mmol). The green-blue solution immediately turned darker green. This solution of 4+BCl₃ can be used for catalysis.

I.28 Synthesis of [Ru(PCy₃)(=CHPh)[O(CH₂CH₂O)₂BCl₂]]BCl₄ (22+BCl₃)

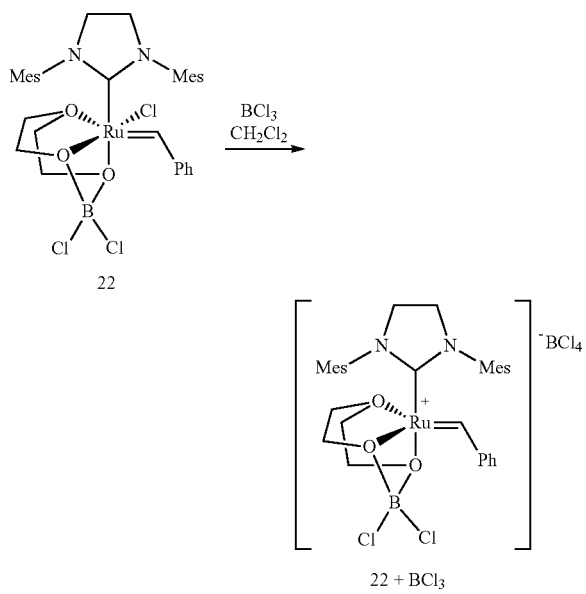

To a CH₂Cl₂ solution (1 mL) of 4 (0.030 g, 0.042 mmol) was added BCl₃ in hexanes (1 M, 42 μL, 0.042 mmol). The green-blue solution immediately turned darker green. This solution of 22+BCl₃ can be used for catalysis.

I.29 Synthesis of [Ru(SIMes)(=CHPh)[O(C₆H₄S)₂BCl₂]]BCl₄ (16+BCl₃)

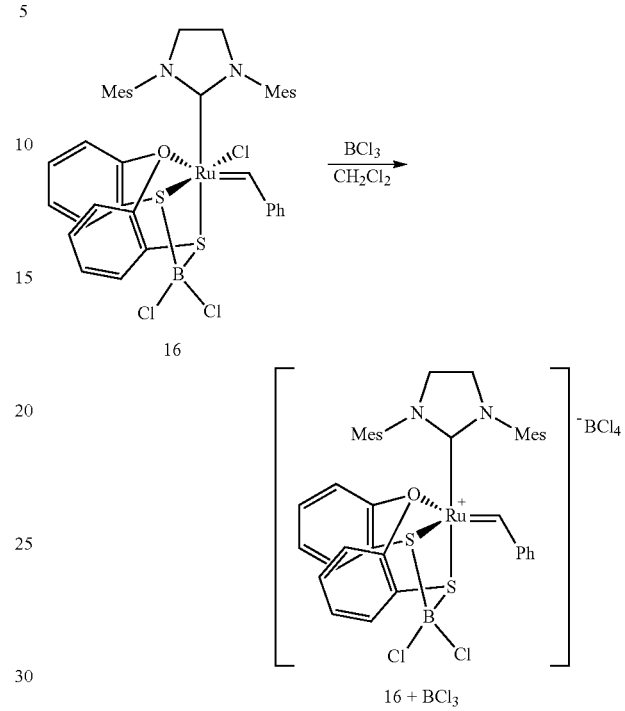

To a CH₂Cl₂ solution (1 mL) of 15 (0.020 g, 0.024 mmol) was added BCl₃ in hexanes (1 M, 24 μL, 0.024 mmol). The green-blue solution immediately turned darker green. This solution of 16+BCl₃ can be used for catalysis.

II Synthesis of Transition Metal Complexes Via Route A

In the following synthesis route A is described to prepare compounds of general formula (I) in accordance with the present invention using thioacetals as one starting material.

All thioacetals were prepared modifying a procedure disclosed in J. Chem. Soc., *Perkin Trans.* 1, 1994, 707-715 (Hu Xianming, Richard M. Kellogg, Fre van Bolhuis) as outlined in the following:

II.1 Synthesis of Thioacetals

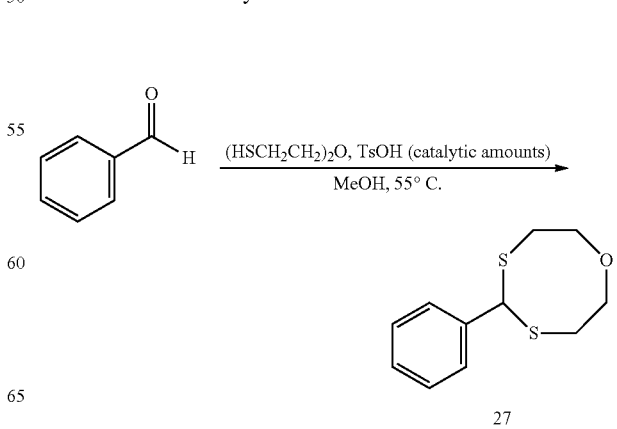

A solution of p-toluenesulfonic acid (5 mg) ("TsOH") in 200 mL of MeOH was heated to 55° C. in a 3-neck round bottom flask fitted with a condenser, addition funnel and septum. A solution of 2-Mercaptoethyl ether (1.065 g, 7.7 mmol) and benzaldehyde (0.817 g, 7.7 mmol) in 150 mL MeOH was added drop wise from the addition funnel over 4 hours. The mixture was left at 55° C. overnight. All volatiles were removed and the white solid was dissolved in 10 mL of toluene. The solution was ran through an alumina plug and all volatiles were removed from the filtrate. The thioacetal (27) was crystallized from $CH_2Cl_2$ and obtained as colorless needles. (1.65 g, 95%).

$^1$H NMR ($C_6D_6$): 7.22 (s, 2H, Ph), 6.84 (t, 2H, Ph), 6.75 (t, 1H, Ph), 5.80 (s, 1H, CH), 3.50 (m, 2H, $CH_2$), 2.90 (m, 2H, $CH_2$), 2.50 (m, 2H, $CH_2$), 2.05 (m, 2H, $CH_2$).

A similar procedure was used for the synthesis of all thioacetals like e.g.

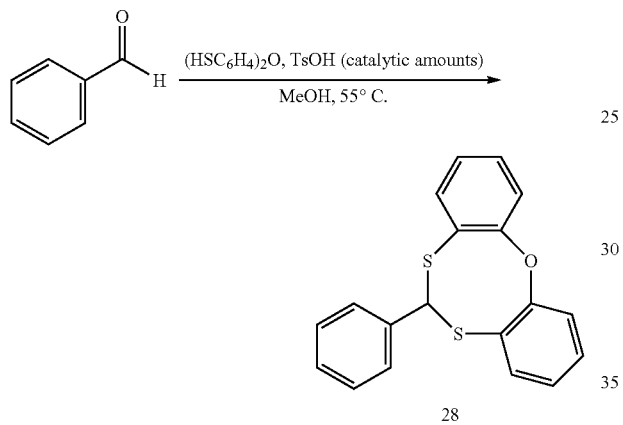

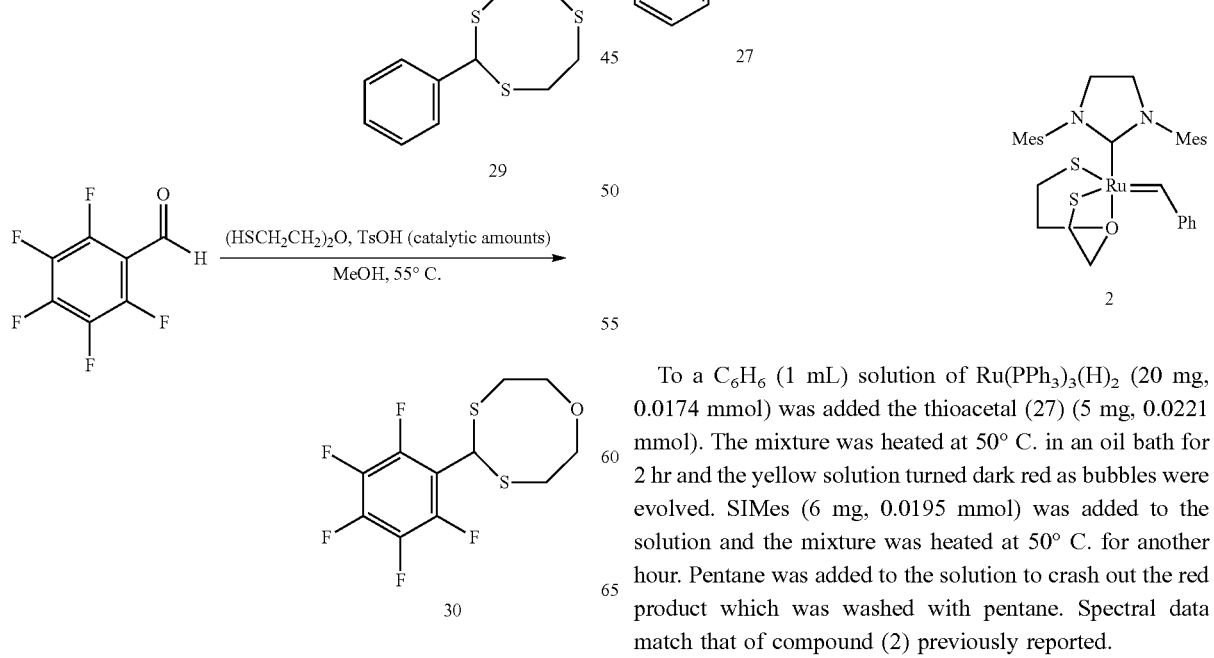

II.2 Synthesis of Compound (1)

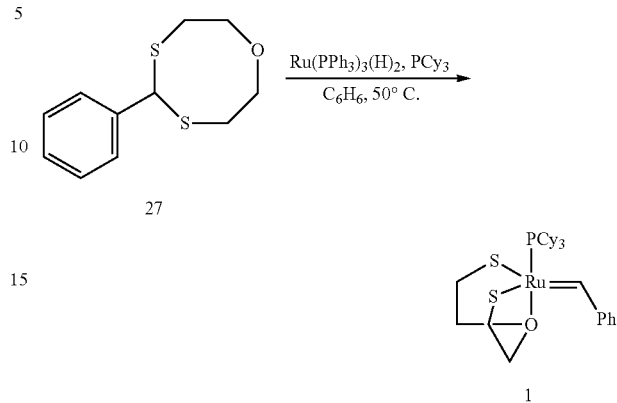

To a $C_6H_6$ (1 mL) solution of Ru(PPh$_3$)$_3$(H)$_2$ (20 mg, 0.0174 mmol) was added PCy$_3$ (6 mg, 0.0214 mmol) and the thioacetal (27) (5 mg, 0.0221 mmol). The mixture was heated at 50° C. in an oil bath for 2 hr and the yellow solution turned dark red as bubbles were evolved. Pentane was added to the solution to crash out the red product which was washed with pentane. Spectral data match that of compound (1) previously reported.

II.3 Synthesis of Compound (2)

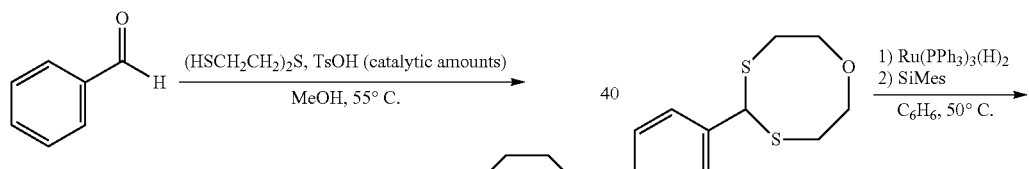

To a $C_6H_6$ (1 mL) solution of Ru(PPh$_3$)$_3$(H)$_2$ (20 mg, 0.0174 mmol) was added the thioacetal (27) (5 mg, 0.0221 mmol). The mixture was heated at 50° C. in an oil bath for 2 hr and the yellow solution turned dark red as bubbles were evolved. SIMes (6 mg, 0.0195 mmol) was added to the solution and the mixture was heated at 50° C. for another hour. Pentane was added to the solution to crash out the red product which was washed with pentane. Spectral data match that of compound (2) previously reported.

II.3a Synthesis of Compound (2)

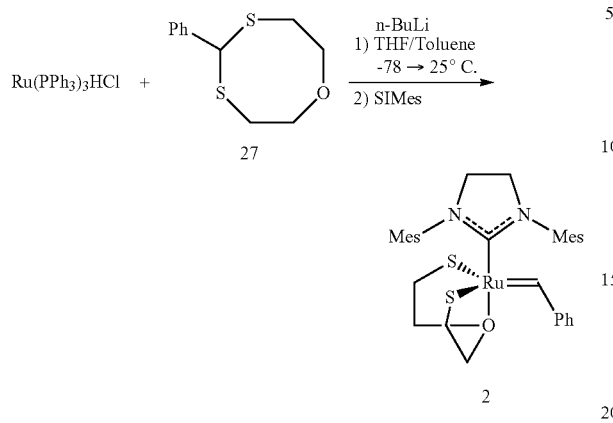

Ru(PPh$_3$)$_3$HCl (0.100 g, 0.108 mmol), thioacetal 27 (0.030 g, 0.130 mmol) and were dissolved in THF (5 mL) and toluene (5 mL) under N$_2$. The solution was cooled to −78° C. and n-BuLi (0.068 mL, 1.6 M in hexanes) was added dropwise. The reaction mixture was stirred at −78° C. for 2 h and then allowed to warm to room temperature. After stirring at room temperature for another 2 h SIMes (0.050 g, 0.162 mmol) was added to the reaction mixture. The solution was then heated to 60° C. for 3 h. The solvent was removed and the resulting brown solid was dissolved in toluene (10 mL) and filtered through a plug of celite. The filtrate was concentrated and hexanes (20 mL) was added to precipitate 2 which was collected by filtration and washed with hexanes (3×5 mL) to give a red solid. All spectral data matched that of compound (2).

II.3b Synthesis of Compound (2)

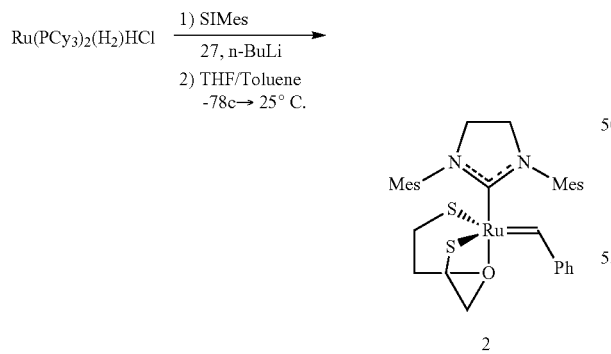

SIMes was stirred with Ru(PCy$_3$)$_2$(H$_2$)HCl in toluene for 2 h. The solution was cooled to −78° C. and n-BuLi was added dropwise. The mixture was stirred for 2 h and allowed to warm to room temperature and stirred for 2 h more. Compound (2) was isolated in an identical fashion to the procedure described in II.3a.

II.4 Synthesis of Compound (8)

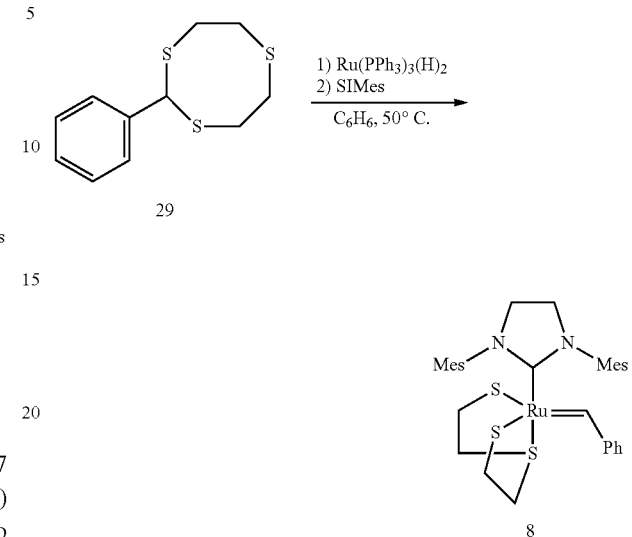

An identical synthetic procedure as the synthesis of compound (2) from Ru(PPh$_3$)$_3$H$_2$ was used to give compound (8).

II.5 Synthesis of Compound (14)

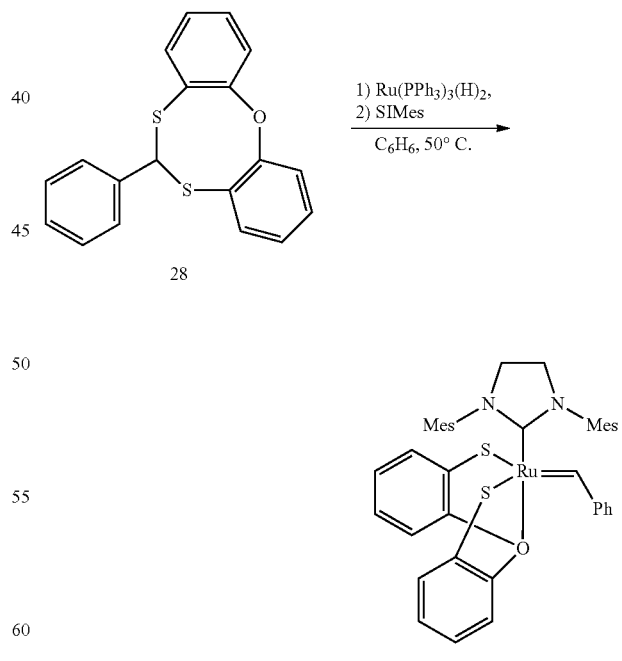

An identical synthetic procedure as used for the synthesis of complex (2) from Ru(PPh$_3$)$_3$H$_2$ was used to give compound (14).

II.6 Synthesis of Compound (1)

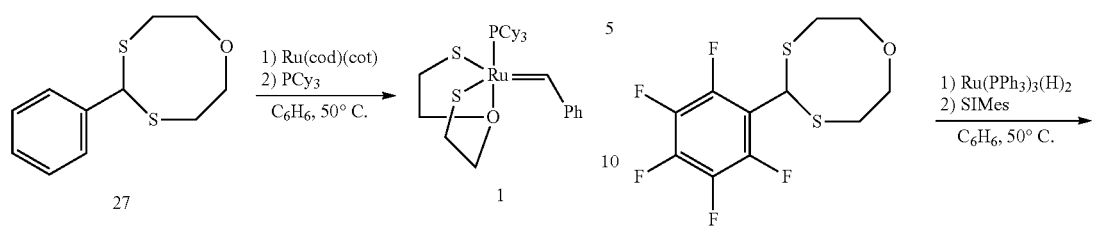

Ru(cod)(cot) (20 mg, 0.063 mmol), PCy$_3$ (20 g, 0.070 mmol) and thioacetal 27 (14 g, 0.063 mmol) were mixed and heated in C$_6$H$_6$ at 50° C. for 2 hr. The solution was cooled to room temperature and the solvent was removed in vacu. The resulting solid was washed with hexanes and dried in vacu to give 1 as a red solid.

II.6a Synthesis of Compound (1)

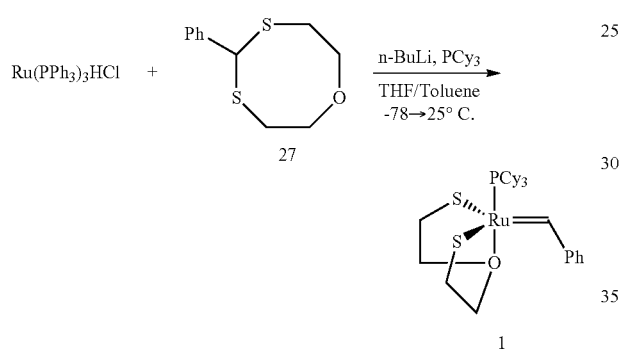

Ru(PPh$_3$)$_3$HCl (0.100 g, 0.108 mmol), thioacetal 27 (0.030 g, 0.130 mmol) and PCy$_3$ (0.045 g, 0.162 mmol) were dissolved in THF (5 mL) and toluene (5 mL) under N$_2$. The solution was cooled to −78° C. and n-BuLi (0.068 mL, 1.6 M in hexanes) was added dropwise. The reaction mixture was stirred at −78° C. for 2 h and then allowed to warm to room temperature. After stirring at room temperature for another 2 h the solvent was pumped off. The resulting brown solid was dissolved in toluene (10 mL) and filtered through a plug of celite. The filtrate was concentrated and hexanes (20 mL) was added to precipitate 1 which was collected by filtration and washed with hexanes (3×5 mL) to give a red solid. All spectral data matched that of compound 1.

II.6b Synthesis of Compound (1)

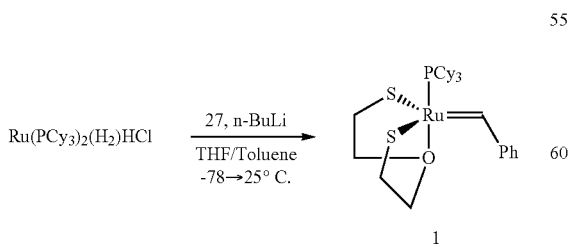

Analog to the process described in II.6a, Ru(PCy$_3$)$_2$(H$_2$)HCl can be used as the metal source without the addition of PCy$_3$.

II.7 Synthesis of Compound 31

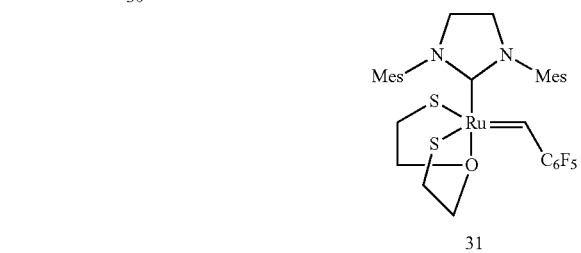

An identical synthetic procedure as the synthesis of Compound (2) from Ru(PPh$_3$)$_3$H$_2$ was used to give compound (31).

III Catalysis Experiments

III.1 Metathesis Reactions Using Compounds (2), (4), and (4)+BCl$_3$

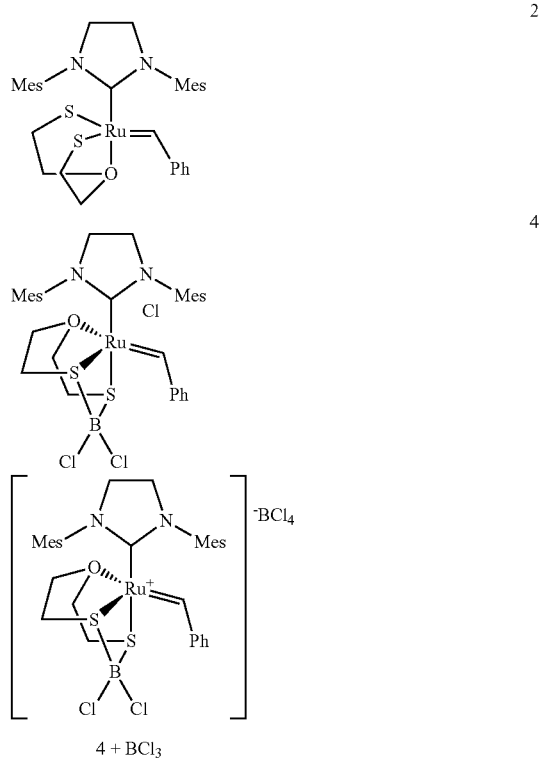

III.1.1 Ring Closing Metathesis of Diethyl Diallyl Malonate

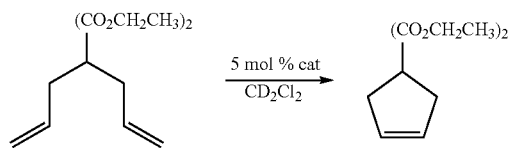

A standard procedure for the ring closing metathesis of diethyl diallyl malonate is as follows. The required amount of catalyst (5 mol %) was weighed out and dissolved in $CD_2Cl_2$. For the tests involving 4 with the addition of another equivalent of $BCl_3$ the required volume was added and the mixture allowed to stand for 5 min. The solutions were placed in an NMR tube equipped with a septa. Diethyl allyl malonate (40 μL, 0.165 mmol) was added via the septum and solution was mixed. Reaction progress was monitored by $^1H$ NMR every 2 min. Reaction progress was determined by integration of the olefinic peaks of the starting material versus the product. The results as listed in Table 1 are graphically shown in FIG. 1.

TABLE 1

Ring Closing Metathesis of diethyl diallyl malonate

| NMR | Time (min) | Conv (%) |
|---|---|---|
| Compound (2) | | |
| 1 | 5 | 0 |
| 2 | 7 | 0 |
| 3 | 9 | 0 |
| 4 | 11 | 0.1 |
| 5 | 13 | 0.1 |
| 6 | 15 | 0.1 |
| 7 | 17 | 0.2 |
| 8 | 19 | 0.2 |
| 9 | 21 | 0.2 |
| 10 | 23 | 0.3 |
| 11 | 25 | 0.3 |
| 12 | 27 | 0.3 |
| 13 | 29 | 0.4 |
| 14 | 31 | 0.4 |
| 15 | 33 | 0.4 |
| 16 | 35 | 0.5 |
| 17 | 37 | 0.5 |
| 18 | 39 | 0.6 |
| 19 | 41 | 0.7 |
| 20 | 43 | 0.7 |
| Compound (4) | | |
| 1 | 5 | 0 |
| 2 | 7 | 0 |
| 3 | 9 | 0 |
| 4 | 11 | 0 |
| 5 | 13 | 0.3 |
| 6 | 15 | 0.4 |
| 7 | 17 | 0.5 |
| 8 | 19 | 0.6 |
| 9 | 21 | 0.6 |
| 10 | 23 | 0.7 |
| 11 | 25 | 0.7 |
| 12 | 27 | 0.8 |
| 13 | 29 | 0.9 |
| 14 | 31 | 0.9 |
| 15 | 33 | 1 |
| 16 | 35 | 1.1 |
| 17 | 37 | 1.2 |
| 18 | 39 | 1.3 |
| 19 | 41 | 1.4 |
| 20 | 43 | 1.4 |

TABLE 1-continued

Ring Closing Metathesis of diethyl diallyl malonate

| NMR | Time (min) | Conv (%) |
|---|---|---|
| Compound (4) + $BCl_3$ | | |
| 1 | 5 | 55.8 |
| 2 | 7 | 67.5 |
| 3 | 9 | 75.4 |
| 4 | 11 | 81.1 |
| 5 | 13 | 85.1 |
| 6 | 15 | 88.2 |
| 7 | 17 | 90.7 |
| 8 | 19 | 92.4 |
| 9 | 21 | 93.7 |
| 10 | 23 | 94.8 |
| 11 | 25 | 95.9 |
| 12 | 27 | 96.4 |
| 13 | 29 | 97 |
| 14 | 31 | 97.4 |
| 15 | 33 | 97.8 |
| 16 | 35 | 98.1 |
| 17 | 37 | 98.2 |
| 18 | 39 | 98.4 |
| 19 | 41 | 98.6 |
| 20 | 43 | 98.6 |

III.1.2 Ring Opening Polymerization of 1,5-cyclooctadiene

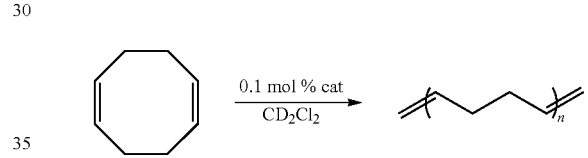

A standard procedure for the ring opening polymerization of 1,5-cyclooctadiene is as follows. Standard solutions in $CD_2Cl_2$ were prepared and the appropriate volumes (0.1 mol %) were diluted for the tests. For tests involving 4 with the addition of another equivalent of $BCl_3$ the required volume was added and the mixture allowed to stand for 5 min. The solutions were placed in an NMR tube equipped with a septa. 1,5-cyclooctadiene (50 μL, 0.40 mmol) was added via the septum and solution was mixed. Reaction progress was monitored by $^1H$ NMR every 2 min. Reaction progress was determined by integration of the peaks of the starting material versus the product. The results as listed in Table 2 are graphically shown in FIG. 2.

TABLE 2

Ring Opening Polymerization of 1,5-cyclooctadiene

| NMR | Time (min) | Conv (%) |
|---|---|---|
| Compound 2 | | |
| 1 | 2 | 1.1 |
| 2 | 4 | 2.4 |
| 3 | 6 | 3.5 |
| 4 | 8 | 4.6 |
| 5 | 10 | 5.7 |
| 6 | 12 | 6.8 |
| 7 | 14 | 7.9 |
| 8 | 16 | 8.9 |
| 9 | 18 | 10 |
| 10 | 20 | 11.4 |

TABLE 2-continued

Ring Opening Polymerization of 1,5-cyclooctadiene

| NMR | Time (min) | Conv (%) |
|---|---|---|
| 11 | 22 | 12.4 |
| 12 | 24 | 13.6 |
| 13 | 26 | 14.8 |
| 14 | 28 | 16.1 |
| 15 | 30 | 17.3 |
| 16 | 32 | 18.5 |
| 17 | 34 | 19.7 |
| 18 | 36 | 21 |
| 19 | 38 | 22.1 |
| 20 | 40 | 23.5 |
| 21 | 42 | 24.7 |
| 22 | 44 | 25.9 |
| Compound 4 | | |
| 1 | 2 | 1.1 |
| 2 | 4 | 1.6 |
| 3 | 6 | 2 |
| 4 | 8 | 2.3 |
| 5 | 10 | 2.5 |
| 6 | 12 | 2.7 |
| 7 | 14 | 2.9 |
| 8 | 16 | 3.1 |
| 9 | 18 | 3.2 |
| 10 | 20 | 3.3 |
| 11 | 22 | 3.6 |
| 12 | 24 | 3.8 |
| 13 | 26 | 3.8 |
| 14 | 28 | 3.9 |
| 15 | 30 | 4.1 |
| 16 | 32 | 4.2 |
| 17 | 34 | 4.4 |
| 18 | 36 | 4.5 |
| 19 | 38 | 4.6 |
| 20 | 40 | 4.7 |
| 21 | 42 | 4.8 |
| 22 | 44 | 4.8 |
| Compound 4 + $BCl_3$ | | |
| 1 | 2 | 17.3 |
| 2 | 4 | 30.9 |
| 3 | 6 | 36.5 |
| 4 | 8 | 39.8 |
| 5 | 10 | 41.7 |
| 6 | 12 | 43.4 |
| 7 | 14 | 44.7 |
| 8 | 16 | 45.7 |
| 9 | 18 | 46.7 |
| 10 | 20 | 47.4 |
| 11 | 22 | 48.2 |
| 12 | 24 | 48.9 |
| 13 | 26 | 49.4 |
| 14 | 28 | 49.9 |
| 15 | 30 | 50.4 |
| 16 | 32 | 50.8 |
| 17 | 34 | 51.1 |
| 18 | 36 | 51.5 |
| 19 | 38 | 52 |
| 20 | 40 | 52.3 |
| 21 | 42 | 52.8 |
| 22 | 44 | 53.1 |

III.1.3 Cross Metathesis of 5-hexenyl acetate and methyl methacrylate

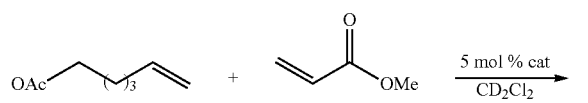

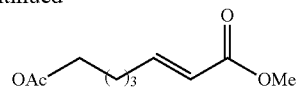

A standard procedure for cross metathesis of 5-hexenyl acetate and methyl methacrylate is as follows. The required amount of catalyst (5 mol %) was weighed out and dissolved in $CD_2Cl_2$. For the tests involving 4 with the addition of another equivalent of $BCl_3$ the required volume was added and the mixture allowed to stand for 5 min. The solutions were placed in an NMR tube equipped with a septa. A mixture of 5-hexenyl acetate (20 μL, 0.12 mmol) and methyl methacrylate (10 μL, 0.11 mmol) was added via the septum and solution was mixed. Reaction progress was monitored by $^1H$ NMR every 2 min. Reaction progress was determined by integration of the olefinic peaks of the starting material versus the product. The results as listed in Table 3 are graphically shown in FIG. 3.

TABLE 3

Cross Metathesis of 5-hexenyl acetate and methyl methacrylate

| NMR | Time (min) | Conv (%) |
|---|---|---|
| Compound (2) | | |
| 1 | 2 | 0 |
| 2 | 4 | 0 |
| 3 | 6 | 0 |
| 4 | 8 | 0 |
| 5 | 10 | 0 |
| 6 | 12 | 0 |
| 7 | 14 | 0 |
| 8 | 16 | 0 |
| 9 | 18 | 0 |
| 10 | 20 | 0 |
| 11 | 22 | 0 |
| 12 | 24 | 0 |
| 13 | 26 | 0 |
| 14 | 28 | 0 |
| 15 | 30 | 0 |
| 16 | 32 | 0 |
| 17 | 34 | 0 |
| 18 | 36 | 0 |
| 19 | 38 | 0 |
| 20 | 40 | 0 |
| 30 | 60 | 0 |
| 40 | 80 | 0 |
| 50 | 100 | 0 |
| 60 | 120 | 0 |
| 70 | 140 | 0 |
| 80 | 160 | 0 |
| 90 | 180 | 0 |
| Compound (4) | | |
| 1 | 2 | 0 |
| 2 | 4 | 0 |
| 3 | 6 | 0 |
| 4 | 8 | 0 |
| 5 | 10 | 0 |
| 6 | 12 | 0 |
| 7 | 14 | 0 |
| 8 | 16 | 0 |
| 9 | 18 | 0 |
| 10 | 20 | 0 |
| 11 | 22 | 0 |
| 12 | 24 | 0 |
| 13 | 26 | 0 |
| 14 | 28 | 0 |
| 15 | 30 | 0 |
| 16 | 32 | 0 |
| 17 | 34 | 0 |
| 18 | 36 | 0 |

TABLE 3-continued

Cross Metathesis of 5-hexenyl acetate and methyl methacrylate

| NMR | Time (min) | Conv (%) |
|---|---|---|
| 19 | 38 | 0 |
| 20 | 40 | 0 |
| 30 | 60 | 0 |
| 40 | 80 | 0 |
| 50 | 100 | 0 |
| 60 | 120 | 0 |
| 70 | 140 | 0 |
| 80 | 160 | 0 |
| 90 | 180 | 0 |
| Compound (4) + BCl₃ | | |
| 1 | 2 | 30.9 |
| 2 | 4 | 40.4 |
| 3 | 6 | 45.6 |
| 4 | 8 | 48.2 |
| 5 | 10 | 50.2 |
| 6 | 12 | 51.9 |
| 7 | 14 | 52.4 |
| 8 | 16 | 53.7 |
| 9 | 18 | 53.7 |
| 10 | 20 | 54.2 |
| 11 | 22 | 54.9 |
| 12 | 24 | 55.2 |
| 13 | 26 | 55.6 |
| 14 | 28 | 56.7 |
| 15 | 30 | 56.8 |
| 16 | 32 | 57.4 |
| 17 | 34 | 57.5 |
| 18 | 36 | 57.8 |
| 19 | 38 | 57.9 |
| 20 | 40 | 58.1 |
| 30 | 60 | 59.2 |
| 40 | 80 | 60.4 |
| 50 | 100 | 60.7 |
| 60 | 120 | 60.9 |
| 70 | 140 | 61.7 |
| 80 | 160 | 62 |
| 90 | 180 | 62.3 |

III.2 Standard Metathesis Reactions with Compound (22)+BCl₃

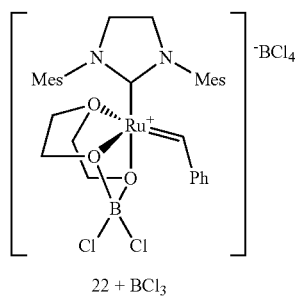

22 + BCl₃

III.2.1 Ring Closing Metathesis of Diethyl Diallyl Malonate

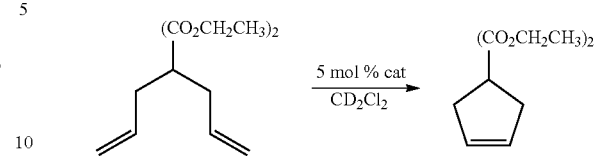

The results as listed in the following Table 4 are graphically shown in FIG. 4.

TABLE 4

Use of catalyst compound (22) + BCl₃ in ring closing metathesis of diethyl diallyl malonate with either 5 mol % of catalyst (Trial A) or 1 mol % catalyst (Trial B)

| Time (min) | Trial A Conversion (%) | Trial B Conversion (%) |
|---|---|---|
| 2 | 24 | 3.7 |
| 4 | 67 | 10.3 |
| 6 | 93 | 15.7 |
| 8 | 100 | 20.3 |
| 10 | | 24.1 |
| 12 | | 28.0 |
| 14 | | 31.2 |
| 16 | | 34.1 |
| 18 | | 36.8 |
| 20 | | 39.4 |
| 22 | | 41.8 |
| 24 | | 43.8 |
| 26 | | 45.7 |
| 28 | | 47.4 |
| 30 | | 49.1 |
| 32 | | 50.5 |
| 34 | | 52.2 |
| 36 | | 53.5 |
| 38 | | 55.0 |
| 40 | | 55.9 |

III.2.2 Ring Opening Polymerization of 1,5-cyclooctadiene

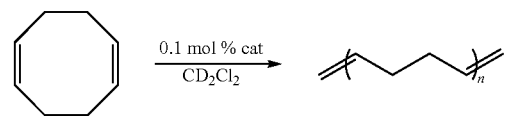

The results as listed in the following Table 5 are graphically shown in FIG. 5.

TABLE 5

Use of catalyst compound (22) + BCl₃ in ring opening polymerization of 1,5-cyclooctadiene

| Time (min) | Conv (%) |
|---|---|
| 2 | 11.5 |
| 4 | 56.5 |
| 6 | 74.3 |
| 8 | 82.1 |
| 10 | 86.2 |
| 12 | 87.6 |

TABLE 5-continued

Use of catalyst compound (22) + BCl₃ in ring opening polymerization of 1,5-cyclooctadiene

| Time (min) | Conv (%) |
|---|---|
| 14 | 88.9 |
| 16 | 90.5 |
| 18 | 91.1 |
| 20 | 92.9 |
| 22 | 93.5 |
| 24 | 94.1 |
| 26 | 94.9 |
| 28 | 95.3 |
| 30 | 95.6 |
| 32 | 95.8 |

III.2.3 Cross Metathesis of 5-hexenyl acetate and methyl methacrylate

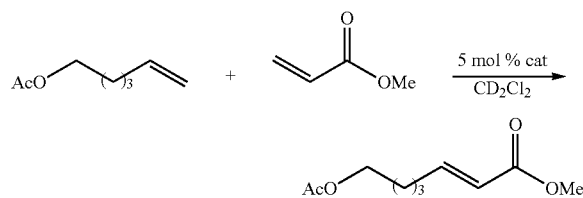

The results as listed in the following Table 6 are graphically shown in FIG. 6.

TABLE 6

Use of catalyst compound 22 + BCl₃ in cross metathesis of 5-hexenyl acetate and methyl methacrylate

| Time (min) | Conv (%) |
|---|---|
| 10 | 19.2 |
| 20 | 22.2 |
| 30 | 26.1 |
| 40 | 27.4 |
| 60 | 28.6 |
| 80 | 29.4 |
| 100 | 30.5 |
| 120 | 30.8 |
| 140 | 31 |
| 160 | 31.3 |
| 180 | 31.5 |

III.3 Standard Metathesis Reactions with Compound (16)+BCl₃

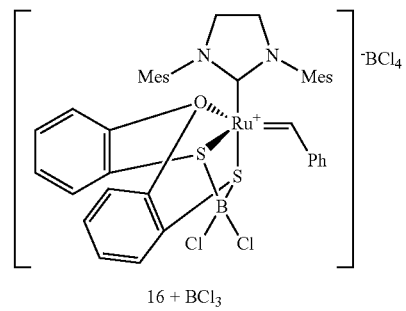

16 + BCl₃

III.3.1 Ring Closing Metathesis of Diethyl Diallyl Malonate

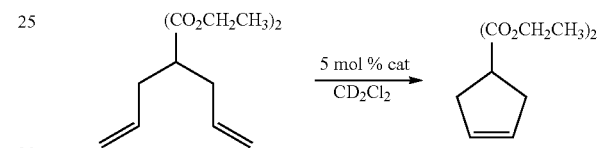

The results as listed in the following Table 7 are graphically shown in FIG. 7.

TABLE 7

Ring Closing Metathesis of diethyl diallyl malonate

| 16 + BCl3 Time (min) | Conv (%) |
|---|---|
| 2 | 5.7 |
| 4 | 12.6 |
| 6 | 15.3 |
| 8 | 17.5 |
| 10 | 19.7 |
| 12 | 21.2 |
| 14 | 23.4 |
| 16 | 25.3 |
| 18 | 26.7 |
| 20 | 27.5 |
| 22 | 29.3 |
| 24 | 30.4 |
| 26 | 31.3 |
| 28 | 32.2 |
| 30 | 32.8 |
| 32 | 33.6 |
| 34 | 33.8 |
| 36 | 34.6 |
| 38 | 35.2 |
| 40 | 35.9 |

III.4 Cross Metathesis of Nitrile Butadiene Rubber (NBR) and 1-hexene

A standard procedure for the cross metathesis of nitrile butadiene rubber (NBR) and 1-hexene is as follows. 75 g of NBR was placed in 325 g of chlorobenzene and placed on a shaker for 48 hr to give a 15 wt % NBR solution. 1-hexene (4 g) was added to the solution and shaken for 1 hr. The catalysts were prepared by dissolving the required mass of compound (4) in $CH_2Cl_2$ (5 mL) in a glove box and 1 equivalent of $BCl_3$ was added. The solutions were stirred for 5 min before being taken out of the glove box and added to the NBR solutions. Samples were taken at 1, 2, 3, 4, and 24 hr. All volatiles were removed from the samples and the Mn, Mw, and PDI were determined by GPC using a polystyrene calibration curve.

All molecular weights Mw (weight average molecular weight) and Mn (number average molecular weight) are hereinafter given in g/mol. "PDI" means polydispersity index.

TABLE 8

| NBR before metathesis | |
|---|---|
| NBR | |
| Mw | 270,500 |
| Mn | 95,500 |
| PDI | 2.83 |

III.4.1 Cross Metathesis Using Compound (4)+$BCl_3$

The cross-metathesis using compound (4)+$BCl_3$ in the amounts mentioned in Table 9 or in comparison Grubbs II catalyst was performed according to the above mentioned standard procedure. The results as listed in the following Table 9.

TABLE 9

Cross metathesis of nitrile butadiene rubber (NBR) and 1-hexene using compound (4) + $BCl_3$ (inventive) and Grubbs II catalyst (comparison)

| Catalyst loading | Inventive example 37.5 mg compound (4) + $BCl_3$ | Inventive example 75 mg compound (4) + $BCl_3$ | Comparison Example 5 mg Grubbs II catalyst |
|---|---|---|---|
| | Reaction time: 24 hr | | |
| Mw | 154,500 | 97,000 | 164,000 |
| Mn | 67,350 | 47,850 | 69,200 |
| PDI | 2.29 | 2.03 | 2.37 |

III.4.2 Cross Metathesis Using Compound (6)

The cross-metathesis using compound (6) with a catalyst loading of 37.5 mg was performed according to the above mentioned standard procedure. The results as listed in the following Table 10.

TABLE 10

Cross metathesis of nitrile butadiene rubber (NBR) and 1-hexene using compound (6) (inventive)

| | Reaction time | | | |
|---|---|---|---|---|
| | 1 hr | 2 hr | 3 hr | 24 hr |
| Mw | 225,000 | 243,000 | 255,500 | 199,500 |
| Mn | 86,000 | 88,800 | 94,500 | 81,000 |
| PDI | 2.62 | 2.74 | 2.70 | 2.46 |

III.4.3 Cross Metathesis Using Compound (22)+$BCl_3$

The cross-metathesis using compound (22)+$BCl_3$ with a catalyst loading of 37.5 mg was performed according to the above mentioned standard procedure. The results as listed in the following Table 11.

TABLE 11

Cross metathesis of nitrile butadiene rubber (NBR) and 1-hexene using compound (22) + $BCl_3$ (inventive) and Grubbs II catalyst (comparison)

| Catalyst loading | Inventive example 37.5 mg compound 4 + $BCl_3$ | Comparison Example 5 mg Grubbs 11 catalyst |
|---|---|---|
| | Reaction time: 0.25 hr | |
| Mw | 156500 | |
| Mn | 63500 | |
| PDI | 2.464567 | |
| | Reaction time: 24 hr | |
| Mw | 160,000 | 164,000 |
| Mn | 63,400 | 69,200 |
| PDI | 2.52 | 2.37 |

III.5 Hydrogenation of NBR

A standard procedure for the hydrogenation of NBR is as follows. A 5 mol % solution of NBR in chlorobenzene was prepared. In a glovebox 2 mL of the NBR solution was place in a vial with a stirbar. The catalyst solution was added to the NBR and the vials were placed in a high pressure Parr reactor. The reactor was purged with $H_2$ and charged to the required pressure. The reactor was heated to the required temperature and the reaction was left for 20 hr. The degree of hydrogenation was determined by IR spectroscopy.

TABLE 11

Hydrogenation of NBR with compounds (2), (20), (22), and (22) + $BCl_3$

| Catalyst | Loading (µmol) | Pressure (bar) | Degree of Hydrogenation |
|---|---|---|---|
| 2 (comparison) | 10 | 50 | 82.4* |
| | 5 | 82 | 71.3* |
| 20 (comparison) | 10 | 50 | Crosslinking |
| | 5 | 82 | Crosslinking |
| 22 (inventive) | 10 | 50 | 73.7 |
| | 10 | 82 | 99 |
| 22 + $BCl_3$ (inventive) | 10 | 50 | 36.4 |
| | 10 | 82 | 98 |

*with Crosslinking

The invention claimed is:

1. A complex having general formula (I)

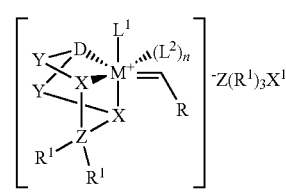

wherein
M means Ru, Os or Fe;
X means O or S;

D means S, O, PR$^2$, or NR$^2$ with R$^2$ meaning straight chain or branched C$_1$-C$_{14}$ alkyl, C$_3$-C$_8$ cycloalkyl, or C$_6$-C$_{24}$ aryl;

Y means a divalent moiety or an unsubstituted or substituted C$_6$-C$_{10}$ arylene group;

R means unsubstituted or substituted C$_6$-C$_{14}$ aryl;

L$^1$ means a ligand;

Z means B, Al, Ga, or In;

R$^1$ are identical or different and represent F, Cl, Br, I, unsubstituted or substituted, straight chain or branched C$_1$-C$_{14}$ alkyl, C$_3$-C$_8$ cycloalkyl, or unsubstituted or substituted C$_6$-C$_{24}$ aryl;

X$^1$ means F, Cl, Br, or I

L$^2$ is a two electron donor ligand; and n Is either 0 or 1.

2. The complex according to claim 1, wherein in general formula (I)

M means Ru

X means O or S;

D means S, O, PR$^2$, or NR$^2$ with R$^2$ meaning straight chain or branched C$_1$-C$_6$ alkyl, C$_5$-C$_6$ cycloakyl, or C$_6$-C$_{14}$ aryl Y means a divalent moiety or an unsubstituted or substituted C$_6$-C$_{10}$ arylene group;

R means unsubstituted or substituted C$_6$-C$_{14}$ aryl;

L$^1$ means either

P(R$^2$)$_3$ wherein R$^2$ are identical or different and mean straight chain or branched C$_1$-C$_8$ alkyl, C$_6$-C$_{14}$ aryl, or C$_3$-C$_{10}$ cycloalkyl, wherein each of the aforementioned groups may be substituted by one or more substituents selected from the group consisting of halogen, SO$_3$Na, C$_1$-C$_8$-alkyl, the latter either unsubstituted or substituted by one or more F, Cl, Br or I, C$_6$-C$_{14}$ aryl, and C$_1$-C$_5$-alkoxy; or an N-heterocyclic carbene ligand of general formulae (IM-a) or (IM-b)

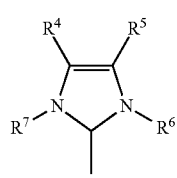
(IM-a)

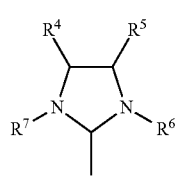
(IM-b)

wherein
R$^4$, R$^5$, R$^6$, R$^7$ are identical or different and are each hydrogen, straight-chain or branched C$_1$-C$_{30}$-alkyl, C$_3$-C$_{20}$-cycloakyl, C$_2$-C$_{20}$-alkenyl, C$_2$-C$_{20}$-alkynyl, C$_6$-C$_4$-aryl, C$_1$-C$_{20}$-carboxylate, C$_1$-C$_{20}$-alkoxy, C$_2$-C$_{20}$-alkenyloxy, C$_2$-C$_{20}$-alkynyloxy, C$_6$-C$_{20}$-aryloxy, C$_2$-C$_{20}$-alkoxycarbonyl, C$_1$-C$_{20}$-alkylthio, C$_6$-C$_{20}$-arylthio, C$_1$-C$_{20}$-alkylsulphonyl, C$_1$-C$_{20}$-alkylsulphonate, C$_6$-C$_{20}$-arylsulphonate or C$_1$-C$_{20}$-alkylsulphinyl;

or in the alternative

R$^6$ and R$^7$ have the above mentioned meanings and at the same time R$^4$ and R$^5$ jointly form a C$_6$-C$_{10}$ cyclic structure together with the two adjacent carbon atoms in the imidazoline or imidazolidine ring;

Z means B, Al, Ga, or In;

R$^1$ are identical or different and represent F, Cl, Br, I, unsubstituted or substituted, straight chain or branched C$_1$-C$_{14}$ alkyl, C$_3$-C$_8$ cycloalkyl, or unsubstituted or substituted C$_6$-C$_{24}$ aryl;

X$^1$ means F, Cl, Br, or I

L$^2$ is a two electron donor ligand; and n is either 0 or 1.

3. The complex according to claim 1, wherein in general formula (I)

M means Ru;

X means O or S;

D means S, O, PR$^2$, or NR$^2$ with R$^2$ meaning straight chain or branched C$_1$-C$_6$ alkyl, C$_5$-C$_6$ cycloalkyl, or C$_6$-C$_{14}$ aryl Y means 1,2-ethylene or 1,2-phenylene;

R means phenyl with none, 1, 2, 3, 4, or 5 substituents selected from the group consisting of F, Cl, Br, and I;

L$^1$ is selected from the group consisting of PPh$_3$, P(p-Tol)$_3$, P(o-Tol)$_3$, PPh(CH$_3$)$_2$, P(CF$_3$)$_3$, P(p-FC$_6$H$_4$)$_3$, P(p-CF$_3$C$_6$H$_4$)$_3$, P(C$_6$H$_4$—SO$_3$Na)$_3$, P(CH$_2$C$_6$H$_4$—SO$_3$Na)$_3$, P(isopropyl)$_3$, P(CH(CH$_3$)CH$_2$CH$_3$)$_3$, P(cyclopentyl)$_3$, P(cyclohexyl)$_3$, P(neopentyl)$_3$, P(neophyl)$_3$, and an N-heterocyclic carbene ligand of general formulae (IM-a) or (IM-b), wherein R$^5$ and R$^7$ are identical or different and represent i-propyl, neopentyl, adamantyl, mesityl or 2,6-diisopropylphenyl, and R$^4$ and R$^5$ are identical or different and represent hydrogen, C$_6$-C$_{24}$-aryl, straight-chain or branched C$_1$-C$_{10}$-alkyl, or together with the carbon atoms to which they are bound form a C$_6$-C$_{10}$ cycloalkyl or C$_6$-C$_{10}$ aryl substituent;

Z means B, Al, Ga, or In;

R$^1$ are identical or different and represent F, Cl, Br, or I;

X$^1$ means F, Cl, Br, or I;

L represents CH$_3$CN, pyrdine or tetrahydrofuran; and n is either 0 or 1.

4. The complex according to claim 1, wherein in formula (I)

M means Ru

X means O or S;

D means S, O, PR$^2$, or NR$^2$ with R$^2$ meaning straight chain or branched C$_1$-C$_6$ alkyl, C$_5$-C$_6$ cycloalkyl, or C$_5$-C$_{14}$ aryl Y means 1,2-ethylene or 1,2-phenylene;

R means phenyl with none or 5 substituents selected from the group consisting of F, Cl, Br, and I;

L$^1$ is selected from the group consisting of PPh$_3$, P(p-To)$_3$, P(o-Tol)$_3$, PPh(CH$_3$), P(CF$_3$)$_3$, P(p-FC$_6$H$_4$)$_3$, P(P—CF$_3$C$_6$H$_4$)$_3$, P(C$_6$H$_4$—SO$_3$Na)$_3$, P(CH$_2$C$_6$H$_4$—SO$_3$Na)$_3$, P(isopropyl)$_3$, P(CH(CH$_3$)CH$_2$CH$_3$)$_3$, P(cyclopentyl)$_3$, P(cyclohexyl)$_3$, P(neopentyl)$_3$, P(neophyl)$_3$, and N-heterocyclic carbene ligands of the structures (VIII-a) to (VIII-o)

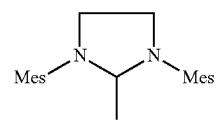
(VIII-a)

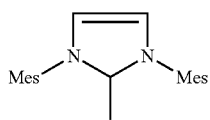
(VIII-b)

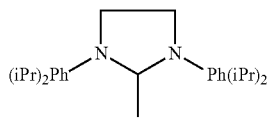
(VIII-c)

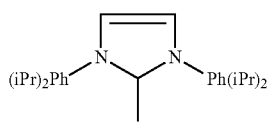
(VIII-d)

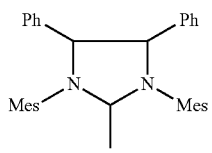
(VIII-e)

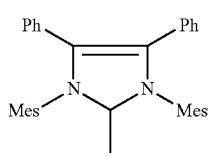
(VIII-f)

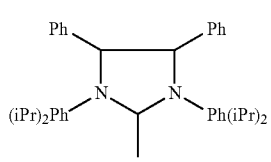
(VIII-g)

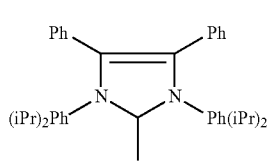
(VIII-h)

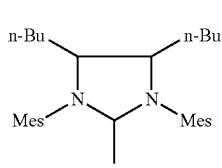
(VIII-k)

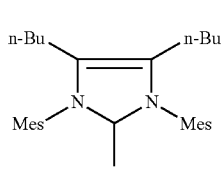
(VIII-m)

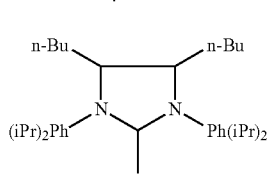
(VIII-n)

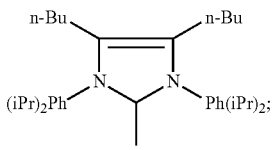
(VIII-o)

Z means B;
R$^1$ are identical and represent Cl;
X$^1$ means Cl;
L$^2$ represents CH$_3$CN, pyridine or tetrahydrofuran; and
n is either 0 or 1.

5. A process for preparing the complex according to claim 1, the process comprising:
(1) reacting a complex of general formula (II)

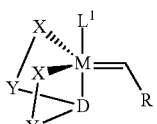
(II)

wherein
M means Ru, Os or Fe;
X means O or S;
D means S, O, PR, or NR$^2$ with R$^2$ meaning straight chain or branched C$_1$-C$_{14}$ alkyl, C$_3$-C$_8$ cycloalkyl, or C$_6$-C$_{24}$ aryl,
Y means a divalent moiety or an unsubstituted or substituted C$_6$-C$_{10}$ arylene group;
R means unsubstituted or substituted C$_6$-C$_{14}$ aryl;
L$^1$ means a ligand;
with a compound of general formula (III)

 ZX$^1$(R$^1$)$_2$ (III)

wherein
Z means B, Al, Ga or In;
X$^1$ means F, Cl, Br, or I; and
R$^1$ are identical or different and represent F, Cl, Br, I, unsubstituted or substituted, straight chain or branched C$_1$-C$_{14}$-alkyl, C$_3$-C$_8$ cycloalkyl, or unsubstituted or substituted C$_6$-C$_{24}$ aryl;
resulting in a complex according to general formula (IV)

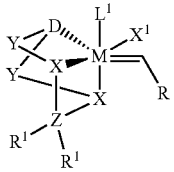
(IV)

and
(2) reacting the compound of general formula (IV) with a compound of general formula (V)

 Z(R$^1$)$_3$ (V)

to obtain the complex catalyst according to general formula (I).

6. The process according to claim 5, further including, to obtain complex catalyst according to general formula (I)

with n being 1, adding the ligand $L^2$ simultaneously with or after addition of the compound of general formula (V) in step 2.

7. The process according to claim 5, wherein:

M means Ru, Os or Fe;

X means O or S;

D means S, O, $PR^2$, or $NR^2$ with $R^2$ meaning straight chain or branched $C_1$-$C_6$ alkyl, $C_5$-$C_6$ cycloalkyl, or phenylene;

Y means 1,2-ethylene, 1,3-propylene, 1,4-butylene, 1,2-phenylene, or 2,3-naphthylene;

R means phenyl with none, 1, 2, 3, 4, or 5 substituents selected from the group consisting of F, Cl, Br, and I;

$L^1$ means an N-heterocyclic carbene ligand or a ligand $P(R^2)_3$ wherein $R^2$ means unsubstituted or substituted, straight chain or branched $C_1$-$C_{14}$ alkyl, unsubstituted or substituted $C_5$-$C_{24}$ aryl, or unsubstituted or substituted $C_3$-$C_{20}$ cycloalkyl;

Z means B;

$X^1$ means Cl; and $R^1$ are identical or different and represent Cl, unsubstituted or substituted, straight chain or branched $C_1$-$C_6$ alkyl, $C_5$-$C_6$ cycloalkyl, or unsubstituted or substituted phenyl.

8. The process according to claim 5, wherein:

M means Ru;

X means O or S;

D means S, O, $PR^2$, or $NR^2$ with $R^2$ meaning straight chain or branched $C_1$-$C_6$ alkyl, $C_5$-$C_6$ cycloalkyl, or phenyl;

Y means 1,2-ethylene or 1, 2-phenyl;

R means phenyl with none or 5 substituents selected from the group consisting of F, Cl, Br, and I;

$L^1$ is selected from the group consisting of $PPh_3$, $P(p-Tol)_3$, $P(o-Tol)_3$, $PPh(CH_3)_2$, $P(CF_3)_3$, $P(p-FC_6H_4)_3$, $P(P\!-\!CF_3C_6H_4)_3$, $P(C_6H_4\!-\!SO_3Na)_3$, $P(CH_2C_6H_4\!-\!SO_3Na)_3$, $P(isopropyl)_3$, $P(CHCH_3(CH_2CH_3))_3$, $P(cyclopentyl)_3$, $P(cyclohexyl)_3$, $P(neopentyl)_3$, $P(neophyl)_3$, and N-heterocyclic carbene ligands of the structures (VIII-a) to (VIII-o)

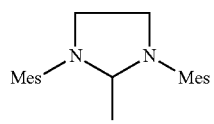
(VIII-a)

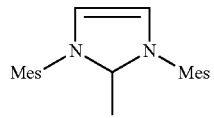
(VIII-b)

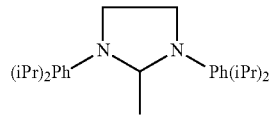
(VIII-c)

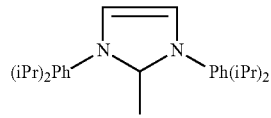
(VIII-d)

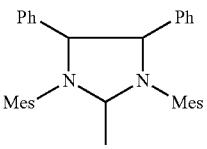
(VIII-e)

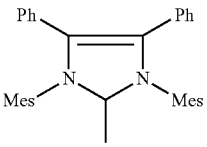
(VIII-f)

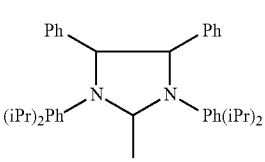
(VIII-g)

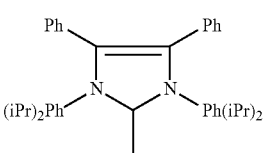
(VIII-h)

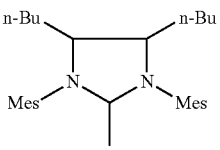
(VIII-k)

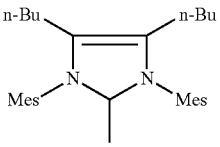
(VIII-m)

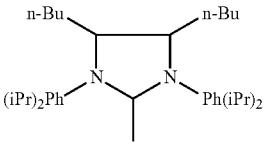
(VIII-n)

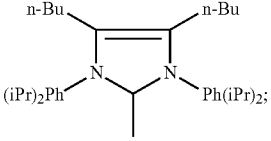
(VIII-o)

Z means B;

$X^1$ means Cl; and $R^1$ are Cl.

9. A process for preparing compounds, the process comprising subjecting a starting compound to a metathesis reaction or a hydrogenation reaction in the presence of a catalyst consisting of the complex according to claim 1.

10. The process according to claim 9, wherein the process is for preparing a nitrile rubber with a weight average molecular weight $M_w'$, the process comprising subjecting a starting nitrile rubber having a weight average molecular weight $M_w$ to a cross-metathesis reaction, wherein the weight average molecular weight of the starting nitrile rubber $M_w$ is higher than the weight average molecular weight $M_w'$ of the nitrile rubber prepared.

11. The process according to claim 9, wherein the process is for preparing a partially or fully hydrogenated nitrile rubber, the process comprising subjecting a starting nitrile rubber to a hydrogenation reaction in the presence of the catalyst to partially or fully hydrogenate the nitrile rubber.

12. The process according to claim 11, wherein the starting nitrile rubber is a copolymer containing repeating units of at least one conjugated diene and at least one α,β-unsaturated nitrile monomer, or a terpolymer containing repeating units of at least one conjugated diene, at least one α,β unsaturated nitrile monomer, and one or more further copolymerizable monomers selected from α,β-unsaturated monocarboxylic acids, their esters or amides, α,β-unsaturated dicarboxylic acids, their monoesters or diesters, or their corresponding anhydrides or amides.

13. A complex according to general formula (IV)

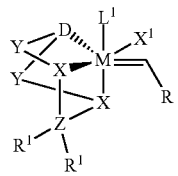

(IV)

wherein
M means Ru, Os or Fe;
X means O or S;
D means S, O, $PR^2$, or $NR^2$ with $R^2$ meaning straight chain or branched $C_1$-$C_{14}$ alkyl, $C_3$-$C_8$ cycloalkyl, preferably $C_5$- or $C_6$-$C_{24}$ aryl;
Y means a divalent moiety or an unsubstituted or substituted $C_6$-$C_{10}$ arylene group;
R means unsubstituted or substituted $C_6$-$C_{14}$ aryl;
$L^1$ means a ligand;
Z means B, Al, Ga, or In;
$R^1$ are identical or different and represent F, Cl, Br, I, unsubstituted or substituted, straight chain or branched $C_1$-$C_{14}$ alkyl, $C_3$-$C_8$ cycloalkyl, unsubstituted or substituted $C_6$-$C_{24}$ aryl; and
$X^1$ means F, Cl, Br, or I.

14. A process for preparing compounds, the process comprising subjecting a starting compound to a metathesis reaction or a hydrogenation reaction in the presence of a catalyst consisting of the complex according to claim 13.

15. A transition metal complex according to general formula (II)

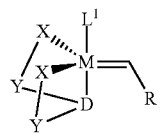

(II)

wherein
M means Ru, Os or Fe;
X means O or S;
D means S, O, $NR^2$ or $PR^2$ with $R^2$ meaning straight chain or branched $C_1$-$C_{14}$ alkyl, $C_3$-$C_8$ cycloalkyl, or $C_6$-$C_{24}$ aryl;
Y means a divalent moiety or an unsubstituted or substituted $C_6$-$C_{10}$ arylene group;
R means unsubstituted or substituted $C_6$-$C_{14}$ aryl;
$L^1$ means a ligand.

16. A process for preparing the transition metal complex (II) according to claim 15, the process comprising:
reacting a compound of general formula (VII)

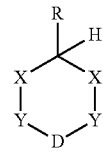

(VII)

wherein
X means O or S;
D means S, O, $PR^2$, or $NR^2$ with $R^2$ meaning straight chain or branched $C_1$-$C_{14}$ alkyl, $C_3$-$C_8$ cycloalkyl, or $C_6$-$C_{24}$ aryl;
Y means a divalent moiety or an unsubstituted or substituted $C_6$-$C_{10}$ arylene group; and
R means unsubstituted or substituted $C_6$-$C_{14}$ aryl,
with either
(i) a M-based complex containing at least one $L^1$ ligand of general formula (VIII)

$M(L^1)_3(H)_2$ (VIII)

wherein
M is Ru, Os or Fe; and
$L^1$ means a ligand; or
(ii) a $M^0$ complex of general formula (IX)

$M(L^3)_t$ (IX)

wherein
t is 2, 3, 4, 5, or 6, and
$L^3$ are identical or different and represent coordinated, straight chain or cyclic olefins and arenes, and
a ligand $L^1$ having the same meanings as given for general formula (VIII).

17. A process for preparing the transition metal complex (II) according to claim 15, the process comprising:
reacting a compound of general formula (X)

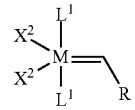

(X)

wherein
M means Ru, Os or Fe;
R means unsubstituted or substituted $C_6$-$C_{14}$ aryl;
$L^1$ are identical or different and mean a ligand; and
$X^2$ are identical or different and represent an anionic ligand
with a compound of general formula (XI)

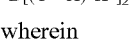

$D[(Y—X)^-K^+]_2$ (XI)

wherein
X means O or S;
D means S, O, $PR^2$, or $NR^2$ with $R^2$ meaning straight chain or branched $C_1$-$C_{14}$ alkyl, $C_3$-$C_8$ cycloalkyl, or $C_6$-$C_{24}$ aryl;
Y means a divalent moiety or an unsubstituted or substituted $C_6$-$C_{10}$ arylene group; and
$K^+$ means a mono charged cation or any equivalent thereof.

* * * * *